US012716054B2

(12) United States Patent
Whiteley et al.

(10) Patent No.: US 12,716,054 B2
(45) Date of Patent: Aug. 25, 2026

(54) OLIGODENDROCYTE PROGENITOR CELL COMPOSITIONS

(71) Applicant: Asterias Biotherapeutics, Inc., Carlsbad, CA (US)

(72) Inventors: Erik Michael Whiteley, Concord, CA (US); Uzma Shoukat-Mumtaz, Fremont, CA (US); Rashi Srivastava, Saratoga, CA (US); Nathan Charles Manley, San Jose, CA (US); Casey Christopher Case, Hillsborough, CA (US)

(73) Assignee: Asterias Biotherapeutics, Inc., Carlsbad, CA (US)

( * ) Notice: Subject to any disclaimer, the term of this patent is extended or adjusted under 35 U.S.C. 154(b) by 0 days.

(21) Appl. No.: 18/424,325

(22) Filed: Jan. 26, 2024

(65) Prior Publication Data

US 2024/0166994 A1 May 23, 2024

Related U.S. Application Data

(62) Division of application No. 16/090,590, filed as application No. PCT/US2017/024986 on Mar. 30, 2017, now Pat. No. 11,920,155.

(60) Provisional application No. 62/315,454, filed on Mar. 30, 2016.

(51) Int. Cl.
*C12N 5/079* (2010.01)
*A61K 35/30* (2015.01)

(52) U.S. Cl.
CPC ............ *C12N 5/0622* (2013.01); *A61K 35/30* (2013.01)

(58) Field of Classification Search
CPC .............................. C12N 5/0622; A61K 35/30
See application file for complete search history.

(56) References Cited

U.S. PATENT DOCUMENTS 6,280,718 B1 8/2001 Kaufman et al.
6,642,048 B2 11/2003 Xu et al.
6,800,480 B1 10/2004 Bodnar et al.
7,285,415 B2 10/2007 Keirstead et al.
7,390,659 B2 6/2008 Jessell et al.
7,524,489 B2 4/2009 Messina et al.
7,579,188 B2 8/2009 Keirstead et al.
7,928,069 B2 4/2011 Prestwich et al.
8,137,969 B2 3/2012 Reubinoff et al.
8,227,247 B2 7/2012 Zhang et al.
8,324,184 B2 12/2012 Prestwich et al.
8,911,777 B2 12/2014 Coulter
9,061,047 B2 6/2015 Davies et al.
9,238,794 B2 1/2016 Shogbon et al.
9,700,003 B1 7/2017 Faue
9,862,925 B2 1/2018 Aharonowiz et al.
9,969,974 B2 5/2018 Tesar et al.
10,137,199 B2 11/2018 Zarembinski et al.
10,138,292 B2 11/2018 Tryggvason et al.
10,286,009 B2 5/2019 Wirth, III et al.
10,301,592 B2 5/2019 Fossati et al.
10,450,546 B2 10/2019 Goldman et al.
10,676,716 B2 6/2020 Fossati et al.
11,123,374 B2 9/2021 Wirth et al.
11,603,518 B2 3/2023 Onishi et al.
11,920,155 B2 3/2024 Whiteley et al.
12,365,872 B2 7/2025 Nair et al.
2004/0009593 A1 1/2004 Keirstead et al.
2005/0031598 A1 2/2005 Levenberg et al.
2010/0015702 A1 1/2010 Rao et al.
2010/0158878 A1 6/2010 Capela et al.
2010/0159595 A1 6/2010 Zhang et al.
2010/0166720 A1 7/2010 Vanderhaeghen et al.
2010/0239541 A1 9/2010 Johe et al.

(Continued)

FOREIGN PATENT DOCUMENTS

CN 1833021 A 9/2006
CN 1852971 A 10/2006

(Continued)

OTHER PUBLICATIONS

Milosevic et al. “Cryopreservation Does Not Affect Proliferation and Multipotency of Murine Neural Precursor Cells” Stem Cells 2005;23:681-688 (Year: 2005).*

(Continued)

*Primary Examiner* — Thane Underdahl

(74) *Attorney, Agent, or Firm* — Fenwick & West LLP; Matthew Pavao; Jessica D. Cande

(57) ABSTRACT

Compositions comprising a population of oligodendrocyte progenitor cells (OPCs), as well as methods of making and using the same, are provided. In one aspect, a container comprising a composition, where the composition comprises a population of cells comprising a plurality of OPCs, and where the population of cells comprises less than 15% undesirable cell types is provided. In another aspect, the population of cells comprises less than 15% undesirable epithelial lineage cells. In yet another aspect, the population of cells comprises less than 2% K7 positive cells. In an aspect, a population of cells comprising a plurality of oligodendrocyte progenitor cells is capable of forming less than one epithelial cyst per 100,000 cells in a cyst assay is provided. An even further aspect of the present disclosure is a container comprising a composition, where the composition comprising a plurality of oligodendrocyte progenitor cells is useful in treating treat stroke, spinal cord injury, and multiple sclerosis.

10 Claims, 18 Drawing Sheets

(56) References Cited

U.S. PATENT DOCUMENTS

| | | | |
|---|---|---|---|
| 2011/0059055 | A1 | 3/2011 | Goldman et al. |
| 2011/0189135 | A1 | 8/2011 | Aharonowiz et al. |
| 2012/0100113 | A1 | 4/2012 | Tesar et al. |
| 2012/0177614 | A1 | 7/2012 | Kido |
| 2013/0004467 | A1 | 1/2013 | Goldman et al. |
| 2013/0022583 | A1 | 1/2013 | Wernig et al. |
| 2013/0143805 | A1 | 6/2013 | Whittaker et al. |
| 2013/0210109 | A1 | 8/2013 | Lebkowski et al. |
| 2013/0280219 | A1 | 10/2013 | Shiels |
| 2014/0170634 | A1 | 6/2014 | Woods |
| 2014/0186955 | A1 | 7/2014 | Vanderhaeghen et al. |
| 2014/0248696 | A1 | 9/2014 | Zhang et al. |
| 2015/0010514 | A1 | 1/2015 | Studer et al. |
| 2015/0017139 | A1 | 1/2015 | Huang et al. |
| 2015/0050667 | A1 | 2/2015 | Carson et al. |
| 2015/0224331 | A1 | 8/2015 | Marsala |
| 2015/0352154 | A1 | 12/2015 | Goldman et al. |
| 2016/0015707 | A1 | 1/2016 | Tesar et al. |
| 2016/0030490 | A1 | 2/2016 | Lanza et al. |
| 2016/0075994 | A1 | 3/2016 | Tesar et al. |
| 2016/0152950 | A1 | 6/2016 | Zhang et al. |
| 2016/0331786 | A1 | 11/2016 | Wirth et al. |
| 2017/0224740 | A1 | 8/2017 | Sing et al. |
| 2018/0236004 | A1 | 8/2018 | Wirth et al. |
| 2018/0237748 | A9 | 8/2018 | Chambers et al. |
| 2019/0262405 | A1 | 8/2019 | Wirth et al. |
| 2019/0336538 | A1 | 11/2019 | Wirth et al. |
| 2020/0087622 | A1 | 3/2020 | Nair et al. |
| 2020/0231932 | A1 | 7/2020 | Onishi et al. |
| 2021/0189335 | A1 | 6/2021 | Whiteley et al. |
| 2021/0379114 | A1 | 12/2021 | Wirth et al. |
| 2023/0139899 | A1 | 5/2023 | Onishi et al. |
| 2024/0082311 | A1 | 3/2024 | Binette et al. |
| 2024/0158745 | A1 | 5/2024 | Skaliter et al. |
| 2024/0382529 | A1 | 11/2024 | Hogge et al. |
| 2026/0002126 | A1 | 1/2026 | Nair et al. |

FOREIGN PATENT DOCUMENTS

| | | | | |
|---|---|---|---|---|
| CN | 101309682 | A | 11/2008 | |
| CN | 102160546 | A | 8/2011 | |
| CN | 102803472 | A | 11/2012 | |
| CN | 103429734 | A | 12/2013 | |
| CN | 105624116 | A | 6/2016 | |
| CN | 107109367 | A | 8/2017 | |
| JP | 2003533224 | A | 11/2003 | |
| JP | 2006517084 | A | 7/2006 | |
| JP | 2010536357 | A | 12/2010 | |
| JP | 2011514147 | A | 5/2011 | |
| JP | 2017511153 | A | 4/2017 | |
| JP | 2022501049 | A | 1/2022 | |
| KR | 20090035372 | A | 4/2009 | |
| WO | 9848001 | A1 | 10/1998 | |
| WO | 0128342 | A1 | 4/2001 | |
| WO | 0188104 | A2 | 11/2001 | |
| WO | WO 2002/044343 | A2 | 6/2002 | |
| WO | WO 2003/020920 | A1 | 3/2003 | |
| WO | WO 2003/050251 | A2 | 6/2003 | |
| WO | 2004007665 | A2 | 1/2004 | |
| WO | WO-2005007797 | A2 * | 1/2005 | ........... C12N 5/0622 |
| WO | 2009097421 | A1 | 8/2009 | |
| WO | 2010151782 | A1 | 12/2010 | |
| WO | 2012096705 | A1 | 7/2012 | |
| WO | 2014124087 | A1 | 8/2014 | |
| WO | 2015143342 | A1 | 9/2015 | |
| WO | 2015179822 | A1 | 11/2015 | |
| WO | 2016103269 | A1 | 6/2016 | |
| WO | 2017132596 | A1 | 8/2017 | |
| WO | 2017173064 | A1 | 10/2017 | |
| WO | 2018053210 | A1 | 3/2018 | |
| WO | 2020061371 | A2 | 3/2020 | |

OTHER PUBLICATIONS

Gordon et al. (Jan. 2012) "Chemokines Influence The Migration And Fate Of Neural Precursor Cells From The Young Adult And Middle-aged Rat Subventricular Zone", Experimental Neurology, 233(1):587-594.

Hatch et al. (2009) "Derivation of High-Purity Oligodendroglial Progenitors", Methods in Molecular Biology, 549:59-75.

Hu et al. (Oct. 15, 2009) "Differentiation of Human Oligodendrocytes from Pluripotent Stem Cells", Nature Protocols, 4(11):1614-1622.

Hu et al. (Jul. 16, 2009) "Hepatocyte Growth Factor Enhances the Generation Of High-Purity Oligodendrocytes From Human Embryonic Stem Cells", Differentiation, 78(2-3):177-184.

Hu et al. (May 2009) "Human Oligodendrocytes From Embryonic Stem Cells: Conserved SHH Signaling Networks and Divergent FGF Effects", Development, 136(9):1443-52.

Hu et al. (Mar. 2, 2010) "Neural Differentiation of Human Induced Pluripotent Stem Cells Follows Developmental Principles but With Variable Potency", Proc Natl Acad Sci U.S.A, 107(9):4335-4340.

Hulsebosch et al. (Jan. 29, 2009) "Rodent Model of Chronic Central Pain After Spinal Cord Contusion Injury and Effects of Gabapentin", Journal of Neurotrauma, 17(12):1205-1217.

Izrael et al. (Mar. 2007) "Human Oligodendrocytes Derived from Embryonic Stem Cells: Effect Of Noggin On Phenotypic Differentiation In Vitro And On Myelination In Vivo", Molecular and Cellular Neuroscience, 34(3):310-323.

Karimi-Abdolrezaee et al. (Mar. 29, 2006) "Delayed Transplantation of Adult Neural Precursor Cells Promotes Remyelination and Functional Neurological Recovery After Spinal Cord Injury", Journal of Neuroscience, 26(13):3377-3389.

Keirstead et al. (May 11, 2005) "Human Embryonic Stem Cell-Derived Oligodendrocyte Progenitor Cell Transplants Remyelinate and Restore Locomotion After Spinal Cord Injury", The Journal of Neuroscience, 25(19):4694-4705.

Kim et al. (Mar. 23, 2019) "Pluripotent Stem Cell-derived Cerebral Organoids Reveal Human Oligodendrogenesis With Dorsal and Ventral Origins", Stem Cell Reports, 12(5):890-905.

Kim et al. (2010) "Robust Enhancement of Neural Differentiation From Human ES and iPS Cells Regardless of Their Innate Difference in Differentiation Propensity", Stem cell reviews and reports, 6(2):270-281.

Klimaschewski et al. (Nov. 2001) "Regulation of Clusterin Expression Following Spinal Cord Injury", Cell and Tissue Research, 306(2):209-216.

Kriks et al. (Nov. 6, 2011) "Dopamine Neurons Derived from Human ES Cells Efficiently Engraft In Animal Models of Parkinson's Disease", Nature, 480(7378):547-551.

Kuespert et al. (May 1, 2016) "Something 2 Talk About—Transcriptional Regulation In Embryonic And Adult Oligodendrocyte Precursors", Brain Research, 1638:16 pages.

Li et al. (May 15, 2013) "Differentiation Of Oligodendrocyte Progenitor Cells From Human Embryonic Stem Cells On Vitronectin-Derived Synthetic Peptide Acrylate Surface", Stem Cells and Development, 22(10):1497-1505.

Li et al. (2021) "Targeting the TGF-B Signaling Pathway For Fibrosis Therapy: A Patent Review", Expert Opinion of Therapeutic Patents, 31(8):723-743.

Lu et al. (2014) "Long-Distance Axonal Growth from Human Induced Pluripotent Stem Cells After Spinal Cord Injury", Neuron, 83(4):789-796.

Lukovic et al. (2017) "Highly Efficient Neural Conversion of Human Pluripotent Stem Cells in Adherent and Animal-Free Conditions", Stem Cells Translational Medicine, 6(4):1217-1226.

Ma et al. (2009) "Oligodendrocyte Precursor Cells Differentially Expressing Noga-A but Not Mag Are More Permissive to Neurite Outgrowth Than Mature Oligodendrocytes", Experimental Neurology, 217(1):184-196.

Manley et al. (Oct. 2017) "Human Embryonic Stem Cell-Derived Oligodendrocyte Progenitor Cells: Preclinical Efficacy and Safety in Cervical Spinal Cord Injury", Stem Cells Translational Medicine, 6(10):1917-1929.

(56) References Cited

OTHER PUBLICATIONS

Medina-Rodriguez et al. (2013) "Protocol to Isolate a Large Amount of Functional Oligodendrocyte Precursor Cells from the Cerebral Cortex of Adult Mice and Humans", PLoS One 8(11):e81620 (13 Pages).
Metz et al. (2000) "Validation of the Weight-Drop Contusion Model in Rats: A Comparative Study of Human Spinal Cord Injury", Journal of Neurotrauma, 17(1):1-17.
Mitsui et al. (2005) "Transplantation of Neuronal and Glial Restricted Precursors Into Contused Spinal Cord Improves Bladder and Motor Functions, Decreases Thermal Hypersensitivity, and Modifies Intraspinal Circuitry", Journal of Neuroscience, 25(42): 9624-9636.
Munst et al. (2018) "In Vitro Segregation and Isolation of Human Pluripotent Stem Cell-Derived Neural Crest Cells", Methods, 133:65-80.
Najm et al. (2011) "Rapid and Robust Generation of Functional Oligodendrocyte Progenitor Cells From Epiblast Stem Cells", Nature Methods, 8(11):957-962.
Nakamura et al. (Jun. 20, 2005) "Transplantation of Embryonic Spinal Cord-Derived Neurospheres Support Growth of Supraspinal Projections and Functional Recovery After Spinal Cord Injury in the Neonatal Rat", Journal of Neuroscience, 81(4):457-468.
Nemati et al. (2016) "Scalable Expansion of Human Pluripotent Stem Cell-Derived Neural Progenitors in Stirred Suspension Bioreactor Under Xeno-free Condition", Methods in Molecular Biology, 1502:143-58.
Nistor et al. (Feb. 2005) "Human Embryonic Stem Cells Differentiate into Oligodendrocytes in High Purity and Myelinate After Spinal Cord Transplantation", Glia, 49(3):385-396.
Noble et al. (2011) "Precursor Cell Biology and the Development of Astrocyte Transplantation Therapies: Lessons from Spinal Cord Injury", Neurotherapeutics, 8(4):677-693.
Nothias et al. (2005) "Combined Effects of Neurotrophin Secreting Transplants, Exercise, and Serotonergic Drug Challenge Improve Function In Spinal Rats", Neurorehabilitation and Neural Repair, 19(4):296-312.
Orentas et al. (Jun. 1999) "Sonic Hedgehog Signaling is Required During the Appearance of Spinal Cord Oligodendrocyte Precursors", Development, 126(11):2419-2429.
Piao et al. (Feb. 5, 2015) "Human Embryonic Stem Cell-derived Oligodendrocyte Progenitors Remyelinate the Brain and Rescue Behavioral Deficits Following Radiation", Cell Stem Cell, 16(2):198-210.
Polisetti et al. (Jul. 11, 2017) "Laminin-511 and -521-Based Matrices for Efficient Ex Vivo-Expansion Of Human Limbal Epithelial Progenitor Cells", Scientific Reports, 5152, 7(1):15 pages.
Priest et al. (Nov. 2015) "Preclinical Safety Of Human Embryonic Stem Cell-derived Oligodendrocyte Progenitors Supporting Clinical Trials In Spinal Cord Injury", Regenerative Medicine, 10(8):939-958.
Riemens et al. (Sep. 2018) "Directing Neuronal Cell Fate in Vitro: Achievements and Challenges", Progress in Neurobiology, 168:42-68 (130 pages).
Rodrigues et al. (Jun. 6, 2017) "Defined and Scalable Differentiation of Human Oligodendrocyte Precursors From Pluripotent Stem Cells in a 3d Culture System", Stem Cell Reports, 8(6):1770-1783.
Rodriguez et al. (Nov. 2018) "The Endocannabinoid 2-arachidonoylglycerol Regulates Oligodendrocyte Progenitor Cell Migration", Biochemical Pharmacology, 157:180-188.
Roy et al. (Oct. 22, 2006) "Functional Engraftment of Human ES Cell-Derived Dopaminergic Neurons Enriched by Coculture with Telomerase-Immortalized Midbrain Astrocytes", Nature Medicine, 12(11):1259-1268.
Scheff et al. (2003) "Experimental Modeling of Spinal Cord Injury: Characterization of a Force-Defined Injury Device", Journal of Neurotrauma, 20(2):179-193.
Sharifi et al. (2011) "FABP7 Expression In Normal And Stab-Injured Brain Cortex And Its Role In Astrocyte Proliferation", Histochemistry and Cell Biology, 136:501-513.
Sharp et al. (2009) "Human Embryonic Stem Cell-Derived Oligodendrocyte Progenitor Cell Transplants Improve Recovery after Cervical Spinal Cord Injury", Stem Cells, 28(1):152-163.
Shin et al. (Sep. 17, 2021) "Sensitive Timing of Undifferentiation in Oligodendrocyte Progenitor Cells and Their Enhanced Maturation in Primary Visual Cortex of Binocularly Enucleated Mice", PLoS One, 16(9):e0257395 (26 pages).
Singh, Juhi (2018) "Role of PDGF-A Activated Intracellular Signalling in Oligodendrocyte Progenitor Migration", PhD Thesis, 153 pages.
Sokol, Sergeiy (Oct. 2011) "Maintaining Embryonic Stem Cell Pluripotency with WNT Signaling", Development, 138(20):4341-4350.
Sundberg et al. (2010) "Production and Isolation of NG2+ Oligodendrocyte Precursors from Human Embryonic Stem Cells in Defined Serum-Free Medium", Stem Cell Research, 5(2):91-103.
Tailor et al. (2013) "Stem Cells Expanded from the Human Embryonic Hindbrain Stably Retain Regional Specification and High Neurogenic Potency", The Journal of Neuroscience 33(30):12407-12422.
Tanaka et al. (2010) "Plasticity in the White Matter and its Relevance to Neuropsychiatric Disorders", Experimental Medicine, 28(5):830-835.
Tang et al. (2014) "Redirection of Doublecortin-Positive Cell Migration by OverExpression of the Chemokines MCP-1, MIP-1 a and Gro-a in the Adult Rat Brain", Neuroscience, 260:240-248.
Totiou et al. (2005) "Spinal Cord Injury Is Accompanied by Chronic Progressive Demyelination", The journal of comparative neurology, 486:373-383.
(Nov. 26, 2014) "Dose Escalation Study of AST-OPC1 in Spinal Cord Injury", NCT02302157, Lineage Cell Therapeutics, Inc., Retrieved from <https://clinicaltrials.gov/study/NCT02302157>, 9 pages.
(2018) "Enhanced Proliferation of Primary Nscs and Sustained Differentiation Into Precursors Using Heat-stable bFGF", Gibco, 3 pages.
European Search Report issued in European Application Application No. 17851575.5, mailed on Mar. 24, 2020, 6 pages.
Extended European Search Report for Application No. EP 19862819.0, mailed on Jun. 10, 2022, 11 pages.
Extended European search report for EP Application No. 20745781.3, mailed on Oct. 26, 2022, 8 Pages.
Extended European Search Report received for European Application No. 17776639.1, mailed on Sep. 26, 2019, 8 pages.
(2016) "History of Changes for Study: NCT02302157", Retrieved from https://clinicaltrials.gov/ct2/history/NCT02302157?v_17=View#StudyPageTop, 5 pages.
International Preliminary Report on Patentability for International Application No. PCT/US2017/051677, mailed on Mar. 28, 2019, 10 pages.
International Preliminary Report on Patentability for PCT Application No. PCT/US2017/24986, mailed on Oct. 11, 2018, 8 pages.
International Preliminary Report on Patentability received for PCT Application No. PCT/US20/014834, mailed on Aug. 5, 2021, 10 pages.
International Preliminary Report on Patentability received for PCT Application No. PCT/US2019/52015, mailed on Apr. 1, 2021, 16 pages.
International Preliminary Report on Patentability received for PCT Application No. PCT/US2022/014373, mailed on Aug. 10, 2023, 8 pages.
International Preliminary Report on Patentability received for PCT Application No. PCT/US2022/019847, mailed on Sep. 21, 2023, 9 pages.
International Search Report and Written Opinion for International Application No. PCT/US2023/061506, mailed on Jul. 3, 2023, 13 pages.
International Search Report and Written Opinion for PCT Application No. PCT/US2017/24986, mailed on Aug. 22, 2017, 11 pages.
International Search Report and Written Opinion issued in International Application No. PCT/US20/014834, mailed on Apr. 23, 2020, 11 Pages.

(56) References Cited

OTHER PUBLICATIONS

International Search Report and Written Opinion issued in International Application No. PCT/US2017/051677, Mailed on Dec. 4, 2017, 11 pages.
International Search Report and Written Opinion received for International Application No. PCT/US19/52015, mailed on Apr. 14, 2020, 20 pages.
International Search Report and Written Opinion received for PCT Patent International Application No. PCT/US2022/014373, mailed on Jun. 30, 2022, 11 pages.
International Search Report and Written Opinion received for PCT Patent International Application No. PCT/US22/19847, Mailed on Jun. 27, 2022, 10 pages.
Abbasalizadeh et al. (2012) "Bioprocess Development For Mass Production Of Size-Controlled Human Pluripotent Stem Cell Aggregates In Stirred Suspension Bioreactor", Tissue Engineering: Part C Methods, 18(11):831-851.
Abecasis et al. (2017) "Expansion of 3D human induced pluripotent stem cell aggregates in bioreactors: Bioprocess intensification and scaling-up approaches", Journal of Biotechnology, 246:81-93.
Almad et al. (2011) "Oligodendrocyte Fate after Spinal Cord Injury", Journal of the American Society for Experimental Neuro Therapeutics, 8(2):262-273.
Alsanie et al. (2013) "Human Embryonic Stem Cell-Derived Oligodendrocytes: Protocols and Perspectives", Stem Cells and Development, 22(18):2459-2472.
Anderson et al. (Nov. 25, 2008) "Acceptable benefits and risks associated with surgically improving arm function in individuals living with cervical spinal cord injury", Spinal Cord, 47(4):334-338.
Bain et al. (Apr. 1995) "Embryonic Stem Cells Express Neuronal Properties in Vitro", Developmental Biology, 168:342-357.
Bardy et al. (Feb. 1, 2013) "Microcarrier Suspension Cultures for High-Density Expansion and Differentiation of Human Pluripotent Stem Cells to Neural Progenitor Cells", Tissue Engineering. Part C, Methods, 19(2):166-180.
Baroti et al. (Jan. 2016) "Transcription Factors Sox5 and Sox6 Exert Direct and Indirect Influences On Oligodendroglial Migration In Spinal Cord And Forebrain", Glia, 64(1):122-138.
Behrmann et al. (1992) "Spinal Cord Injury Produced by Consistent Mechanical Displacement of the Cord in Rats: Behavioral and Histologic Analysis", Journal of Neurotrauma, 9(3):197-217.
Bergles et al. (2016) "Oligodendrocyte Development and Plasticity", Cold Spring Harbor Perspectives in Biology, 8(2):a020453 (29 Pages).
Bian et al. (May 18, 2016) "Sequential Differentiation of Embryonic Stem Cells into Neural Epithelial-like Stem Cells and Oligodendrocyte Progenitor Cells", Plos One, 11(5):e0155227 (15 pages).
Cai et al. (Jan. 6, 2005) "Generation of Oligodendrocyte Precursor Cells from Mouse Dorsal Spinal Cord Independent of Nkx6 Regulation and Shh Signaling", Neuron, 45(1):41-53.
Cao et al. (Jan. 2001) "Pluripotent Stem Cells Engrated into the Normal or Lesioned Adult Rat Spinal Cord Are Restricted to a Glial Lineage", Experimental Neurology, 167(1):48-58.
Chapman et al. (Sep. 2012) "Evaluating the first-in-human clinical trial of a human embryonic stem cell-based therapy", Kennedy Institute of Ethics Journal, 22(3):243-261.
Chew et al. (2014) "Finding Degrees of Separation: Experimental Approaches for Astroglial and Oligodendroglial Cell Isolation and Genetic Targeting", Journal of Neuroscience Methods, 236:125-147.
Clausi et al. (2017) "Delayed ALK5 Inhibition Improves Functional Recovery in Neonatal Brain Injury", Journal of Cerebral Blood Flow and Metabolism, 37(3):787-800.
Davies et al. (Mar. 2, 2011) "Transplantation of Specific Human Astrocytes Promotes Functional Recovery after Spinal Cord Injury", Plos One, 6(3):e17328 (13 pages).
Doi et al. (Feb. 10, 2012) "Prolonged Maturation Culture Favors a Reduction in the Tumorigenicity and the Dopaminergic Function of Human ESC-Derived Neural Cells in a Primate Model of Parkinson's Disease", Stem cells, 30(5):935-945.
Douvaras et al. (Aug. 12, 2014) "Efficient Generation of Myelinating Oligodendrocytes from Primary Progressive Multiple Sclerosis Patients by Induced Pluripotent Stem Cells", Stem Cell Reports, 3(2):250-259.
Douvaras et al. (Jul. 2, 2015) "Generation and Isolation of Oligodendrocyte Progenitor Cells From Human Pluripotent Stem Cells", Nature Protocols, 10:143-1154.
Du et al. (2014) "Mechanism of SB431542 in Inhibiting Mouse Embryonic Stem Cell Differentiation", Cellular Signalling, 26(10):2107-2116.
Du et al. (Jun. 15, 2002) "Oligodendrocytes As Providers Of Growth Factors", Journal of Neuroscience Research, 68(6):647-654.
Ebrahimi-Barough et al. (Oct. 2013) "Differentiation of Human Endometrial Stromal Cells into Oligodendrocyte Progenitor Cells (OPCs)", Journal of Molecular Neuroscience, 51(2):265-273.
Eze et al. ( 2021) "Single-cell Atlas of Early Human Brain Development Highlights Heterogeneity of Human Neuroepithelial Cells and Early Radial Glia" Nature Neuroscience, 24(4):584-594.
Faulkner et al. (Dec. 2005) "Human Embryonic Stem Cell-Derived Oligodendrocyte Progenitors for the Treatment of Spinal Cord Injury", Transplant Immunology, 15(2):131-142.
Fuhrmann et al. (Jan. 1, 2016) "Injectable Hydrogel Promotes Early Survival of Induced Pluripotent Stem Cell-Derived Oligodendrocytes and Attenuates Longterm Teratoma Formation in a Spinal Cord Injury Model", Biomaterials, 83:23-36.
Gallo et al. (1995) "Developmental and Growth Factor-induced Regulation of Nestin in Oligodendrocyte Lineage Cells", Journal of Molecular Neuroscience, 15(1):394-406.
Gallo et al. (Apr. 15, 1996) "Oligodendrocyte Progenitor Cell Proliferation and Lineage Progression Are Regulated By Glutamate Receptor-Mediated K+ Channel Block", The Journal of Neuroscience, 16(8):2659-2670.
Goldman, Steven A. (Jul. 2005) "Stem and Progenitor Cell-based Therapy of the Human Central Nervous System", Nature Biotechnology, 23(7):862-871.
Gomez-Puerto et al. (2019) "Bone Morphogenetic Protein Receptor Signal Transduction In Human Disease", The journal of pathology, 247(1):9-20.
Abiraman et al. (Feb. 25, 2015) "Anti-Muscarinic Adjunct Therapy Accelerates Functional Human Oligodendrocyte Repair", The Journal of Neuroscience, 35(8):3676-3688.
Fischer et al. (Jul. 2020) "Transplanting Neural Progenitor Cells To Restore Connectivity After Spinal Cord Injury", Nature Reviews Neuroscience, 21(7):366-383.
Liu et al. (Jun. 15, 2013) "Microfibrous Carriers for Integrated Expansion and Neural Differentiation of Embryonic Stem Cells in Suspension Bioreactor", Biochemical Engineering Journal, 75: 55-63.
Xue et al. (May 21, 2018) "Mechanics-Guided Embryonic Patterning of Neuroectoderm Tissue from Human Pluripotent Stem Cells", Nature Materials, 17(7): 633-641.
Xue et al. (2008) "Proliferation, Multipotency and Neuronal Differentiation of Cryopreserved Neural Progenitor Cells Derived from the Olfactory Neuroepithelium of The Adult Rat", Cell Biology International, 32: 950-958.
Yu et al. (Jan. 5, 2018) "ERK Inhibition Promotes Neuroectodermal Precursor Commitment by Blocking Self-Renewal and Primitive Streak Formation of the Epiblast", Stem Cell Research & Therapy, 9(2):1-13.
Zhou et al. (Apr. 2, 2014) "GSK3β Promotes the Differentiation of Oligodendrocyte Precursor Cells via β-Catenin-Mediated Transcriptional Regulation", Molecular Neurobiology, 50:507-519.
Vadivelu et al. (2015) "Ng2+ Progenitors Derived from Embryonic Stem Cells Penetrate Glial Scar and Promote Axonal Outgrowth Into White Matter After Spinal Cord Injury", Stem Cells Translational Medicine, 4(4):401-411.
Vigil et al. (Apr. 2008) "Efficacy of Tacrolimus In Inhibiting Inflammation Caused By Carrageenan In A Murine Model of Air Pouch", Transplant Immunology, 19(1):25-29.
Wang et al. (2014) "ApoE Mimetic Ameliorates Motor Deficit and Tissue Damage in Rat Spinal Cord Injury", Journal of Neuroscience Research, 92(7):884-892.

(56) References Cited

OTHER PUBLICATIONS

Wang et al. (2013) "Human Ipsc-derived Oligodendrocyte Progenitor Cells Can Myelinate and Rescue a Mouse Model of Congenital Hypomyelination", Cell Stem Cell, 12(2):252-264.
Wilkins et al. (Aug. 14, 2001) "A Role for Oligodendrocyte-Derived IGF-1 In Trophic Support of Cortical Neurons", Glia, 36(1):48-57.
Wirth, E (May 16, 2014) "Phase I Clinical Trial of Human Embryonic Stem Cell-Derived Oligodendrocyte Progenitors in Subjects with Neurologically Complete Thoracic Spinal Cord Injury: Results and Next Steps", American Spinal Injury Association (ASIA) 2014 Meeting, San Antonio, Texas, (Oral Presentation), 7 pages.
Wright et al. (2014) "Novel Roles for Osteopontin and Clusterin in Peripheral Motor and Sensory Axon Regeneration", Journal of Neuroscience, 34(5):1689-1700.
Yamashita et al. (Feb. 13, 2017) "Differentiation of Oligodendrocyte Progenitor Cells From Dissociated Monolayer and Feederfree Cultured Pluripotent Stem Cells", PLOS One, 12(2):e0171947(16 pages).
Zhang et al. (2018) "Highly Efficient Methods to Obtain Homogeneous Dorsal Neural Progenitor Cells From Human and Mouse Embryonic Stem Cells and Induced Pluripotent Stem Cells", Stem Cell Research and Therapy, 9(67):13 pages.
Zhang et al. (2006) "Oligodendrocyte Progenitor Cells Derived from Human Embryonic Stem Cells Express Neurotrophic Factors", Stem Cells and Development, 15(6): 943-952.
Zhang et al. (2010) "Pax6 Is a Human Neuroectoderm Cell Fate Determinant", Cell Stem Cell 7(1):90-100.
Zhang et al. (Apr. 2011) "Role of Matrix Metalloproteinases and Therapeutic Benefits of Their Inhibition in Spinal Cord Injury", Neurotherapeutics, 8(2):206-220.
Zhu et al. (Nov. 2011) "Dorsally-derived Oligodendrocytes in the Spinal Cord Contribute to Axonal Myelination During Development and Remyelination Following Focal Demyelination", Glia, 59(11):1612-1621.
Dhara et al. (Oct. 15, 2008) "Neural Differentiation of Human Embryonic Stem Cells", Journal of Cellular Biochemistry, 105(3): 633-640.
U.S. Appl. No. 19/235,019, filed Jun. 11, 2025, Inventor Rekha R. Nair et al.
Ahmed et al., "Decorin blocks scarring and cystic cavitation in acute and induces scar dissolution in chronic spinal cord wounds", Neurobiology of Disease 64 (2014) pp. 163-176.
Alsanie et al., "Human Embryonic Stem Cell-Derived Oligodendrocytes: Protocols and Perspectives", Stem Cells and Development, 2013, 22(18):pp. 2459-2476.
Anderson et al., "Small-molecule dissection of BMP signaling" Nature Chemical Biology, Jan. 2008, 4(1): pp. 15-16.
Armstrong et al., "Type 1 Astrocytes and Oligodendrocyte-type 2 Astrocyte Glial Progenitors Migrate Toward Distinct Molecules", Journal of Neuroscience Research, Nov. 1990, 27(3):pp. 400-407.
Backe et al., "Post-traumatic spinal cord cysts evaluated by magnetic resonance imaging", Paraplegia, 1991 29(9), pp. 607-612.
Bell et al., "Ossification of the lumbosacral dura and arachnoid following spinal cord trauma, Case report" Paraplegia. Sep. 1995; 33(9): pp. 543-546.
Biering-Sørensen et al., "International Spinal Cord Injury Data Sets", Spinal Cord, 2006; 44(9): pp. 530-534.
Bond et al., "The Dynamic Role of Bone Morphogenetic Proteins in Neural Stem Cell Fate and Maturation," Dev Neurobiol. Jul. 2012;72(7): pp. 1068-1084, 25 pages provided.
Bradbury et al., "Moving beyond the glial scar for spinal cord repair", Nature Communications, Aug. 28, 2019, 10(1): 3879, 15 pages provided.
Briscoe et al., "A Hedgehog-insensitive Form of Patched Provides Evidence for Direct Long-range Morphogen Activity of Sonic Hedgehog in the Neural Tube", Molecular Cell, Jun. 2001, 7(6):pp. 1279-1291.
Brodbelt et al., "Post-traumatic syringomyelia: A review", Journal of Clinical Neuroscience, 2003, 10(4), pp. 401-408.
Bunge et al., "Observations on the pathology of human spinal cord injury. A review and classification of 22 new cases with details from a case of chronic cord compression with extensive focal demyelination", Adv Neurol 1993; 59: pp. 75-89.
Burks et al., "Imaging characteristics of chronic spinal cord injury identified during screening for a cell transplantation clinical trial", Neurosurgical Focus, 2019, 46(3), E8, pp. 1-6.
Cao et al., "Transplantation of Ciliary Neurotrophic Factor-Expressing Adult Oligodendrocyte Precursor Cells Promotes Remyelination and Functional Recovery after Spinal Cord Injury", Journal of Neuroscience, Feb. 24, 2010, 30(8):pp. 2989-3001.
Chambers et al., "Highly efficient neural conversion of human ES and iPS cells by dual inhibition of SMAD signaling", Nature Biotechnology, vol. 27, No. 3, 1 (Mar. 1, 2009), pp. 275-280.
Crompton et al., "Stepwise, Non-Adherent Differentiation of Human Pluripotent Stem Cells to Generate Basal Forebrain Cholinergic Neurons Via Hedgehog Signaling", Stem Cell Research, Aug. 9, 2013, 11(3):pp. 1206-1221.
Curt et al., "Recovery from a spinal cord injury: significance of compensation, neural plasticity, and repair", J Neurotrauma. Jun. 2008; 25(6): pp. 677-685.
Curtis et al., "A First-in-Human, Phase 1 Study of Neural Stem Cell Transplantation for Chronic Spinal Cord Injury", Cell Stem Cell. 2018, 22: pp. 941-950.
Dai et al., "The Trophic Role of Oligodendrocytes in the Basal Forebrain", Journal of Neuroscience Jul. 2, 2003, 23(13): pp. 5846-5853.
Davies et al., "Decorin Promotes Plasminogen/Plasmin Expression Within Acute Spinal Cord Injuries and by Adult Microglia in Vitro", Journal of Neurotrauma, 23, 2006, (3-4): pp. 397-408.
Devivo et al., "International Spinal Cord Injury Core Data Set", Spinal Cord. 2006; 44(9): pp. 535-540.
Devivo, "Sir Ludwig Guttmann Lecture: trends in spinal cord injury rehabilitation outcomes from model systems in the United States: 1973-2006", Spinal Cord. Nov. 2007;45(11): pp. 713-721.
Dreau et al., "Dorsal-ventral Patterning of the Neural Tube: a Tale of Three Signals", Developmental Neurobiology, Dec. 2012, 72(12):pp. 1471-1481.
Drukker et al., "Isolation Of Primitive Endoderm, Mesoderm, Vascular Endothelial And Trophoblast Progenitors From Human Pluripotent Stem Cells", Nat Biotechnol, Jun. 2012, 30(6):pp. 531-542, 24 pages provided.
Duester Gregg, "Retinoic Acid Synthesis and Signaling during Early Organogenesis", Cell, Sep. 19, 2008, 134(6): pp. 921-931, 23 pages provided.
Dunn et al., "Cyclosporin: An Updated Review Of The Pharmacokinetic Properties, Clinical Efficacy and Tolerability of a Microemulsion-Based Formulation (Neoral)1 in Organ Transplantation", Drugs, 2001, 61(13): 2 pages.
Ericson et al., "Two Critical Periods of Sonic Hedgehog Signaling Required for the Specification of Motor Neuron Identity", Cell, Nov. 15, 1996, 87(4): pp. 661-673.
Esmaeili et al., "Decorin treatment of spinal cord injury", Neural Regeneration Research, Sep. 15, 2014, 9(18):pp. 1653-1656.
Fehlings et al., "The optimal radiologic method for assessing spinal canal compromise and cord compression in patients with cervical spinal cord injury. Part II: Results of a multicenter study", Spine, 1999, 24(6), pp. 605-613.
Fitzgerald et al., "Characterization of Neogenin-expressing Neural Progenitor Populations and Migrating Neuroblasts in the Embryonic Mouse Forebrain", Neuroscience, 142(3): pp. 703-716.
Flanders et al., "Forecasting motor recovery after cervical spinal cord injury: Value of MR imaging", Radiology, 1996, 201(3), pp. 649-655.
Flanders et al., "The relationship between the functional abilities of patients with cervical spinal cord injury and the severity of damage revealed by MR imaging" AJNR Am J Neuroradiol. May 1999; 20(5): pp. 926-934.
Franz et al., "Motor levels in high cervical spinal cord injuries: Implications for the International Standards for Neurological Classification of Spinal Cord Injury", The Journal of Spinal Cord Medicine, 2016, 39(5), pp. 513-517.
Genbacev et al., "Serum-Free Derivation of Human Embryonic Stem Cell Lines on Human Placental Fibroblast Feeders", Fertility and Sterility, May 2005, 83(5): pp. 1517-1529.

(56) References Cited

OTHER PUBLICATIONS

Gubbiotti et al., "Decorin interacting network: A comprehensive analysis of decorin-binding partners and their versatile functions", Matrix Biol. Sep. 2016; 55: pp. 7-21.
Hill et al., "Sustained Release of Decorin to the Surface of the Eye Enables Scarless Corneal Regeneration", 2018, NPJ Regen Med, 3: 23, pp. 1-12.
Hinman et al., "Remodeling Of The Axon Initial Segment After Focal Cortical And White Matter Stroke", Stroke, Jan. 2013, 44(1): 182-189, 8 pages provided.
Hodgetts et al., "A comparison of the behavioral and anatomical outcomes in sub-acute and chronic spinal cord injury models following treatment with human mesenchymal precursor cell transplantation and recombinant Decorin", Experimental Neurology 248 (2013), pp. 343-359.
Huang et al., "Functions of EpCAM in physiological processes and diseases (Review)", Int J Mol Med, Oct. 2018; 42(4):pp. 1771-1785.
Ilic, "Latest Developments in the Field of Stem Cell Research and Regenerative Medicines, Regenerative Medicine", 9(6), Published online: Nov. 28, 2014, pp. 713-719.
Janesick et al., "Retinoic Acid Signaling and Neuronal Differentiation", Cell Mol Life Sci, Apr. 2015, 72(8):pp. 1559-1576.
Kakulas, "A review of the neuropathology of human spinal cord injury with emphasis on special features", J Spinal Cord Med. 1999 Summer; 22(2): pp. 119-124.
Kakulas, "The applied neuropathology of human spinal cord injury", Spinal Cord, Jan. 29, 1999, 37(2): pp. 79-88.
Kantor et al., "Semaphorin SA Is a Bifunctional Axon Guidance Cue Regulated by Heparan and Chondroitin Sulfate Proteoglycans", 2004 Neuron, vol. 44, pp. 961-975.
Kim et al., "Differential and cooperative actions of Olig1 and Olig2 transcription factors on immature proliferating cells after contusive spinal cord injury", Glia, 2011, 59(7): pp. 1094-1106.
Kim et al., "Highly Pure and Expandable PSA-NCAM-Positive Neural Precursors from Human ESC and iPSC-Derived Neural Rosettes", PLoS One, 2012, e39715, 7(7): 12 pages.
Kimura et al., "Ultrasonographic quantification of spinal cord and dural pulsations during cervical laminoplasty in patients with compressive myelopathy", Eur Spine J, 2012, 21, pp. 2450-2455.
Kious et al., "Identification and Characterization of a Calcium Channel γ Subunit Expressed in Differentiating Neurons and Myoblasts", Developmental Biology, 243, 2002, pp. 249-259.
Kirkeby et al., "Generation of Regionally Specified Neural Progenitors And Functional Neurons From Human Embryonic Stem Cells Under Defined Conditions", Cell Reports, Jun. 28, 2012, 1(6): pp. 703-714.
Kirshblum et al., "International standards for neurological classification of spinal cord injury (Revised 2011)", The Journal of Spinal Cord Medicine, Nov. 2011, 34(6): pp. 535-546.
Krebsbach et al., "The Role of Integrin a6 (CD49f) in Stem Cells: More than a Conserved Bio marker", Stem Cells and Development, Aug. 1, 2017, 26(15): pp. 1090-1099.
Kudoh et al., "Distinct Roles for Fgf, Wnt and Retinoic Acid in Posteriorizing the Neural Ectoderm", Development, Sep. 2002, 129(18): pp. 4335-4346.
Kumar et al., "Deconstructing Transcriptional Heterogeneity In Pluripotent Stem Cells", Nature, Dec. 4, 2014, 516(7529): 56-61, 26 pages.
Kurek et al., "Endogenous WNT Signals Mediate BMP-Induced and Spontaneous Differentiation of Epiblast Stem Cells and Human Embryonic Stem Cells", Stem Cell Reports, Jan. 13, 2015, 4(1): pp. 114-128.
Kutejova et al., "Neural Progenitors Adopt Specific identities by Directly Repressing All Alternative Progenitor Transcriptional Programs", Developmental Cell, Mar. 21, 2016, 36(6):pp. 639-653.
Lee et al., "Establishment and Maintenance of Human Embryonic Stem Cell Lines on Human Feeder Cells Derived From Uterine Endometrium Under Serum-Free Condition", Biology of Reproduction, Jan. 2005, 72(1): pp. 42-49.
Lee et al., "The Specification of Dorsal Cell Fates in the Vertebrate Central Nervous System", Annual Review of Neuroscience, 1999, 22:pp. 261-294.
Li et al., "BMP4 Regulation of Human Trophoblast Development", Int J Dev Biol, 2014, 58(2-4): pp. 239-246, 17 pages provided.
Lineage Cell Therapeutics, Inc., NCT01217008: Safety Study of GRNOPC1 in Spinal Cord Injury, Record History—Study details, NIH Clinical Trials, 2014, 10 Pages. <URL: clinicaltrials.gov/study/NCT01217008>.
Lin et al., "Bioinformatic Analysis Reveals Potential Properties of Human Claudin-6 Regulation and Functions", Oncology Report, Aug. 2017, 38(2):pp. 875-885.
Lippmann et al., "Deterministic HOX Patterning in Human Pluripotent Stem Cell-Derived Neuroectoderm", Stem Cell Reports, Apr. 14, 2015, 4:pp. 632-644.
Magu et al., "Evaluation of Traumatic Spine by Magnetic Resonance Imaging and Correlation with Neurological Recovery", Asian Spine Journal, 2015, 9(5), pp. 748-756.
Marklund et al., "Detailed Expression Analysis of Regulatory Genes in the Early Developing Human Neural Tube", Stem Cells and Development, 2014, 23(1):pp. 5-15.
Maynard et al., "International Standards for Neurological and Functional Classification of Spinal Cord Injury", Spinal Cord, 1997, 35(5), pp. 266-274.
Menon et al., "A short review on a complication of lumbar spine surgery: CSF leak", Clin Neurol Neurosurg. Dec. 2015; 139: pp. 248-251.
Milhorat et al., "Pathological basis of spinal cord cavitation in syringomyelia: Analysis of 105 autopsy cases", Journal of Neurosurgery, 1995, 82(5), pp. 802-812.
Milner et al., "Contrasting Effects of Mitogenic Growth Factors on Oligodendrocyte Precursor Cell Migration". Glia, Jan. 1997, 19(1):pp. 85-90.
Minor et al., "Decorin Promotes Robust Axon Growth on Inhibitory CSPGS and Myelin via a Direct Effect on Neurons", Neurobiol Dis, Jun. 26, 2008, 32(1):pp. 88-95.
National Spinal Cord Injury Statistical Center, "Spinal cord injury facts and figures at a glance", J Spinal Cord Med. Jan. 2013; 36(1): pp. 1-2.
Norenberg et al., "The Pathology of Human Spinal Cord Injury: Defining the Problems", 2004, Journal of Neurotrauma 21 (4): pp. 429-440.
Okamura et al., "Immunological properties of human embryonic stem cell-derived oligodendrocyte progenitor cells", J Neuroimmunol 2007; 192(12): pp. 134-144.
O'Shea et al., "Cell biology of spinal cord injury and repair", The Journal of Clinical Investigation, 2017, 127(9), pp. 3259-3270.
Ota et al., "BMP and FGF-2 Regulate Neurogenin-2 Expression and the Differentiation of Sensory Neurons and Glia", Developmental Dynamics, Mar. 2006, 235(3):pp. 646-655.
Patterson et al., "Defining the Nature of Human Pluripotent Stem Cell Progeny", Cell Research, Jan. 2012, 22(1):pp. 178-193.
Patthey et al., "Signaling Pathways Regulating Ectodermal Cell Fate Choices", Experimental Cell Research, Aug. 9, 2013, 321(1):pp. 11-16.
Pauly et al., "Adherent vs. Free-Floating Neural Induction by Dual SMAD Inhibition for Neurosphere Cultures Derived from Human Induced Pluripotent Stem Cells", Frontiers in Cell and Developmental Biology, Feb. 6, 2018, 6(3):8 pages.
Perrouin-Verbe et al., "Post-traumatic syringomyelia and post-traumatic spinal canal stenosis: A direct relationship: Review of 75 patients with a spinal cord injury", Spinal Cord, 1998, 36(2), pp. 137-143.
Petit et al., "Adult Spinal Cord Radial Glia Display a Unique Progenitor Phenotype". PloSONE, Sep. 2011, 6(9):e24538 (15 pages).
Ravanelli et al., "Motor Neurons and Oligodendrocytes Arise From Distinct Cell lineages by Progenitor Recruitment", Genes & Development, 2015, 29(23): pp. 2504-2515.
Reiprich et al., "From CNS stem cells to neurons and glia: Sox for everyone", Cell Tissue Res, 2015, 359: pp. 111-124.

(56) References Cited

OTHER PUBLICATIONS

Richards et al., "Human Feeders Support Prolonged Undifferentiated Growth of Human Inner Cell Masses and Embryonic Stem Cells", Nature Biotechnology, Sep. 2002, 20(9): pp. 933-936.
Rosler et al., "Long-Term Culture of Human Embryonic Stem Cells In Feeder-Free Conditions", Developmental Dynamics, Feb. 2004, 229(2): pp. 259-274.
Rowitch, "Glial Specification in the Vertebrate Neural Tube". Nature Reviews Neuroscience, May 2004, 5(5):pp. 409-419.
Sezer et al., "Chronic complications of spinal cord injury", World J Orthop. Jan. 18, 2015; 6(1): pp. 24-33.
Sharifi et al., "Differential expression and regulatory roles of FABP5 and FABP7 in oligodendrocyte lineage cells", Cell Tissue Res, 2013, 354: pp. 683-695.
Shira et al., "The Axon-glia Unit White Matter Stroke: Mechanisms of Damage and Recovery", Brain Research, Oct. 14, 2015, 1623: 123-134, 22 pages.
Shultz et al., "Humanized Mice In Translational Biomedical Research", Nature Review Immunology, Feb. 2007, 7:pp. 118-130.
Singh, et al., "Allogeneic Stem Cell Transplantation: A Historical and Scientific Overview", Cancer Res, Nov. 15, 2016, 76(22): pp. 6445-6451.
Sozmen et al., "A White Matter Stroke Model in the Mouse; Axonal Damage, Progenitor Response and MRI Correlates", J Neurosci Methods, 2009, 180(2):pp. 261-272, 24 pages provided.
Stacpoole et al., "High Yields of Oligodendrocyte Lineage Cells From Human Embryonic Stem Cells at Physiological Oxygen Tensions for Evaluation of Translational Biology", Stem Cell Reports, 2013, 1(5):pp. 437-450.
Steeves et al., "Extent of spontaneous motor recovery after traumatic cervical sensorimotor complete spinal cord injury", Spinal Cord, Feb. 2011, 49(2): pp. 257-265.
Steeves et al., "Outcome Measures for Acute/Subacute Cervical Sensorimotor Complete (AIS-A) Spinal Cord Injury During a Phase 2 Clinical Trial", Topics in Spinal Cord Injury Rehabilitation: Winter, 2012, 18(1): pp. 1-14.
Stolt et al., "SoxD Proteins Influence Multiple Stages of Oligodendrocyte Development and Modulate SoxE Protein Function, Developmental Cell", Nov. 11, 2006, pp. 697-709.
Stosic-Grujicic et al., "Induction Of Experimental Autoimmune Encephalomyelitis In Dark Agouti Rats Without Adjuvant", Clinical and Experimental Immunology, Jan. 16, 2004, 136:pp. 49-55.
Stylianou et al., "Novel cryoprotectant significantly improves the post-thaw recovery and quality of HSC from CB", Cytotherapy, 2006, 8(1), pp. 57-61.
Sui et al., "Signaling Pathways During Maintenance and Definitive Endoderm Differentiation of Embryonic Stem Cells", Int J Dev Biol, 2013, 57(1):pp. 1-12.
Thomson et al., "Embryonic Stem Cell Lines Derived from Human Blastocysts", Science, 282 (1998): pp. 1145-1147.
Tripathi et al., "NG2 glia generate new oligodendrocytes but few astrocytes in a murine experimental autoimmune encephalomyelitis model of demyelinating disease" J Neurosci. 2010 30(48): pp. 16383-16390.
Vallstedt et al., "Multiple Dorsoventral Origins of Oligodendrocyte Generation in the Spinal Cord and Hindbrain", Neuron, Jan. 6, 2005, 45(1):pp. 55-67.
Wang et al., "A clinical magnetic resonance imaging study of the traumatised spinal cord more than 20 years following injury", Paraplegia 1996, 34(2), pp. 65-81.
Wang et al., "ApoE Mimetic Ameliorates Motor Deficit and Tissue Damage in Rat Spinal Cord Injury", Journal of Neuroscience Research, 2014, 92(7): pp. 884-892.
Watabe et al., "Roles of TGF-beta Family Signaling in Stem Cell Renewal and Differentiation", Cell Res, 2009, 19(1):pp. 103-115.
Wheeler et al., "Extracellular cues influencing oligodendrocyte differentiation and (re)myelination," Exp Neurol, 2016. 283(Pt B): pp. 512-530, 49 pages provided.
Wiles, "Embryonic Stem Cell Differentiation In Vitro", Methods in Enzymology, 1993, 225: pp. 900-918.
Wilkins et al., "Oligodendrocytes Promote Neuronal Survival and Axonal Length by Distinct Intracellular Mechanisms: A Novel Role for Oligodendrocyte-Derived Glial Cell Line-Derived Neurotrophic Factor", J Neurosci. Jun. 15, 2003;23(12): pp. 4967-4974.
Williams, "Pathogenesis of post-traumatic syringomyelia", British Journal of Neurosurgery, 1992, vol. 6: 517-520.
Wirth, "Dynamic assessment of intraspinal neural graft survival using magnetic resonance imaging", Exp Neurol. Nov. 1995;136(1): pp. 64-72.
Wirth et al. "Feasibility and safety of neural tissue transplantation in patients with syringomyelia", J Neurotrauma. Sep. 2001; 18(9): pp. 911-929.
Wirth et al. "In vivo magnetic resonance imaging of fetal cat neural tissue transplants in the adult cat spinal cord", J Neurosurg. Feb. 1992;76(2): pp. 261-274.
Woo et al., "Notch Signaling Is Required for Maintaining Stem-Cell Features of Neuroprogenitor Cells Derived From Human Embryonic Stem Cells", BMC Neuroscience, Aug. 17, 2009, 10(97):12 pages.
Wu et al., "Combined Transplantation of Gdas(Bmp) and Hr-decorin in Spinal Cord Contusion Repair", Neural Regeneration Research, Aug. 2013, 8(24):pp. 2236-2248.
Xu et al., "Basic Fibroblast Growth Factor Supports Undifferentiated Human Embryonic Stem Cell Growth Without Conditioned Medium", Stem Cells, Mar. 2005, 23(3): pp. 315-323.
Xu et al., "Feeder-Free Growth of Undifferentiated Human Embryonic Stem Cells", Nature Biotechnology, Oct. 1, 2001, 19: pp. 971-974.
Zhang et al., "An RNA-Sequencing Transcriptome and Splicing Database Of Glia, Neurons, And Vascular Cells of The Cerebral Cortex", The Journal of Neuroscience, Sep. 3, 2014, 34(36):pp. 11929-11947.
Zheng et al., "Differentiation of glial cells From hiPSCs: Potential Applications in Neurological Diseases and Cell Replacement Therapy", Frontiers in Cellular Neuroscience, Aug. 2018, 12:239, 21 pages.
Zohrabian et al., "Imaging of trauma of the spine" 2016, Handbook of Clinical Neurology, vol. 136, pp. 747-767, 21 pages.
U.S. Appl. No. 19/464,885, filed Jan. 30, 2026 Inventor Kento Onishi et al.
Ben-David et al. "Immunologic and chemical targeting of the tight-junction protein Claudin-6 eliminates tumorigenic human pluripotent stem cells" Nat Commun 4, 1992 (2013), 8 pages.
Firstword Pharma "Geron Presents Data from GRNOPC1 Trial at International Conferences on Spinal Cord Medicine and Rehabilitation" FirstWord Pharma, 2011, 4 Pages. Accessed Feb. 11, 2026).
Lu et al. "Epithelial cell adhesion molecule regulation is associated with the maintenance of the undifferentiated phenotype of human embryonic stem cells" J Biol Chem. Mar. 19, 2010; 285(12): pp. 8719-8732.
Olmer et al. "Suspension culture of human pluripotent stem cells in controlled, stirred bioreactors" Tissue Engineering Part C: Methods May 22, 2012, 18(10): pp. 772-784.
Yocum et al. "Safety of tacrolimus in patients with rheumatoid arthritis: long-term experience" Rheumatology, 2004, 43: pp. 992-999.
Yu et al. "CD49f enhances multipotency and maintains sternness through the direct regulation of OCT4 and SOX2" Stem Cells, 2012, 30: pp. 876-887.

* cited by examiner

Dorsomorphin

CHIR99021

*FIG. 3*

Purmorphamine

OLIGODENDROCYTE PROGENITOR CELL COMPOSITIONS

CROSS REFERENCE TO RELATED APPLICATIONS

This application is a divisional of U.S. patent application Ser. No. 16/090,590, filed Oct. 1, 2018, now U.S. Pat. No. 11,920,155, which is a U.S. National Phase application, filed under U.S.C. § 371, of International Application No. PCT/US2017/024986, filed Mar. 30, 2017, which claims priority to, and the benefit of, U.S. Provisional Patent Application Ser. No. 62/315,454, filed Mar. 30, 2016, entitled "Oligodendrocyte Progenitor Cell Compositions," the contents of each of which are incorporated herein by reference in their entireties.

FIELD

The present disclosure relates to the field of cell biology of oligodendrocyte progenitor cells. More specifically, the disclosure relates to compositions comprising oligodendrocyte progenitor cells, and methods of making and using the same.

BACKGROUND

When pluripotent cells, including human embryonic stem cells (hESCs) are cultured, varying levels of spontaneous differentiation can occur during their expansion. Such spontaneous differentiation can subsequently impair the hESCs' capacity to undergo directed differentiation into a particular cell type, including oligodendrocyte progenitor cells (OPC). For example, the H1 line of hESCs has previously been shown to undergo spontaneous differentiation when grown under conventional culture conditions, with a propensity for trophectoderm lineage differentiation (Drukker M, Tang C, Ardehali R, Rinkevich Y, Scita J, Lec A S, Mosley A R, Weissman I L, Soen Y. Isolation of primitive endoderm, mesoderm, vascular endothelial and trophoblast progenitors from human pluripotent stem cells. Nat Biotechnol. 2012 May 27; 30(6):531-42; Wang Z, Oron E, Nelson B, Razis S, Ivanova N. Distinct lineage specification roles for NANOG, OCT4, and SOX2 in human embryonic stem cells. Cell Stem Cell. 2012 Apr. 6; 10(4):440-54). This spontaneous differentiation is regulated in part by endogenous WNT signaling within the hESCs (Kumar R M, Cahan P, Shalek A K, Satija R, DaleyKeyser A J, Li H, Zhang J, Pardee K, Gennert D, Trombetta J J, Ferrante T C, Regev A, Daley G Q, Collins J J. Deconstructing transcriptional heterogeneity in pluripotent stem cells. Nature. 2014 Dec. 4; 516(7529):56-61). However, the field is in disagreement regarding whether activation or inhibition of the WNT pathway would be beneficial for controlling differentiation. Namely, Kurek et al. suggests that inhibition of the WNT pathway would reduce spontaneous differentiation (Kurek D, Neagu A, Tastemel M, Tüysüz N, Lehmann J, van de Werken H J, Philipsen S, van der Linden R, Maas A, van IJcken W F, Drukker M, ten Berge D. Endogenous WNT signals mediate BMP-induced and spontaneous differentiation of epiblast stem cells and human embryonic stem cells. Stem Cell Reports. 2015 Jan. 13; 4(1):114-28).

When H1 hESCs are expanded and then subjected to directed differentiation into OPCs, the differentiating cells exhibit increased expression of trophectoderm-associated genes, including transcription factors. This indicates that cell types outside of the neuroectoderm lineage are able to persist during differentiation. In turn, this persistence of non-neuroectoderm lineage markers during differentiation correlates with undesirable cell types in the final OPC population, including, for example, epithelial cells, chondrocyte progenitor cells, and retinal pigment epithelial cells.

Several markers have been used to quantify the levels of undesirable cells in an OPC population. Namely, detection of these markers may be achieved by cell phenotyping methods such as flow cytometry and gene expression profiling. For example, flow cytometry analysis may be used to detect varying levels of epithelial cells based on the presence of markers associated with epithelial cells, including, for example, EpCAM, CD49f/ITGA6, E-Cadherin, Cytokeratin 7 (K7), Pan-cytokeratin (PCK), CA125/MUC16, Endorepellin/Perlecan, as well as others listed in TABLE 1. In addition, gene expression profiling by quantitative polymerase chain reaction (qPCR) may be used to indicate varying levels of chondrocyte progenitor cells and retinal pigment epithelial cells based on expression of OLR1 and RPE65, respectively.

Although efforts have been made to produce a population of OPCs with a low level of undesirable cell types, strategies such as cell sorting and antibody depletion are complex and frequently require generating customized reagents that are expensive and not scalable.

SUMMARY

An aspect of the disclosure includes compositions comprising a plurality of oligodendrocyte progenitor cells (OPCs), as well as methods of making and using the same for improving one or more neurological functions in a subject in need of treatment. The present disclosure comprises, in one aspect thereof, a composition comprising a population of cells comprising a plurality of OPCs and less than 15% undesirable cell types. The present disclosure further comprises, in one aspect thereof, a method of achieving a population of cells comprising a plurality of OPCs and less than 15% undesirable cell types. The present disclosure also comprises, in one aspect thereof, a method of characterizing a population of cells comprising a plurality of OPCs and less than 15% undesirable cell types. In addition, the present disclosure also comprises, in one aspect thereof, a method of using a population of cells comprising a plurality of OPCs and less than 15% undesirable cell types. The present disclosure further comprises, in one aspect thereof, a method of generating a population of cells comprising a plurality of OPCs and less than 15% undesirable cell types.

More particularly, the present disclosure includes, in an aspect, a container comprising a composition, where the composition comprises a population of cells comprising a plurality of oligodendrocyte progenitor cells, and where the population of cells comprises less than 15% undesirable cell types. In certain aspects, the population of cells comprises less than 15% epithelial lineage cells. In certain aspects, the population of cells comprises less than 2% K7 positive cells. In certain aspects, the population of cells comprises less than 5% PCK positive cells.

An aspect of the present disclosure is a container comprising a composition, where the composition comprises a population of cells comprising a plurality of oligodendrocyte progenitor cells (OPCs), and where the plurality of OPCs comprises the in vitro derived progeny of one or more stem cell sources selected from the group consisting of human embryonic stem cells, primate pluripotent stem cells, and induced pluripotent stem cells.

A further aspect of the present disclosure is a container comprising a composition, where the composition comprises a population of cells comprising a plurality of oligodendrocyte progenitor cells, and where the population of cells is capable of forming less than or equal to one epithelial cyst per 100,000 cells in a cyst assay. In yet another aspect, the population of cells is capable of producing an ectopic tissue in less than 2% of subjects upon implantation of up to $20\times10^6$ cells into a central nervous system injury site.

An even further aspect of the present disclosure is a container comprising a composition, where the composition comprises a population of cells comprising a plurality of oligodendrocyte progenitor cells, and where the population of cells is useful in treating stroke, spinal cord injury, and/or multiple sclerosis.

BRIEF DESCRIPTION OF THE DRAWINGS

FIG. 1 shows the chemical structure of SB431542 in accordance with the present disclosure;

FIG. 2 shows the chemical structure of Dorsomorphin in accordance with the present disclosure;

Figure 3:
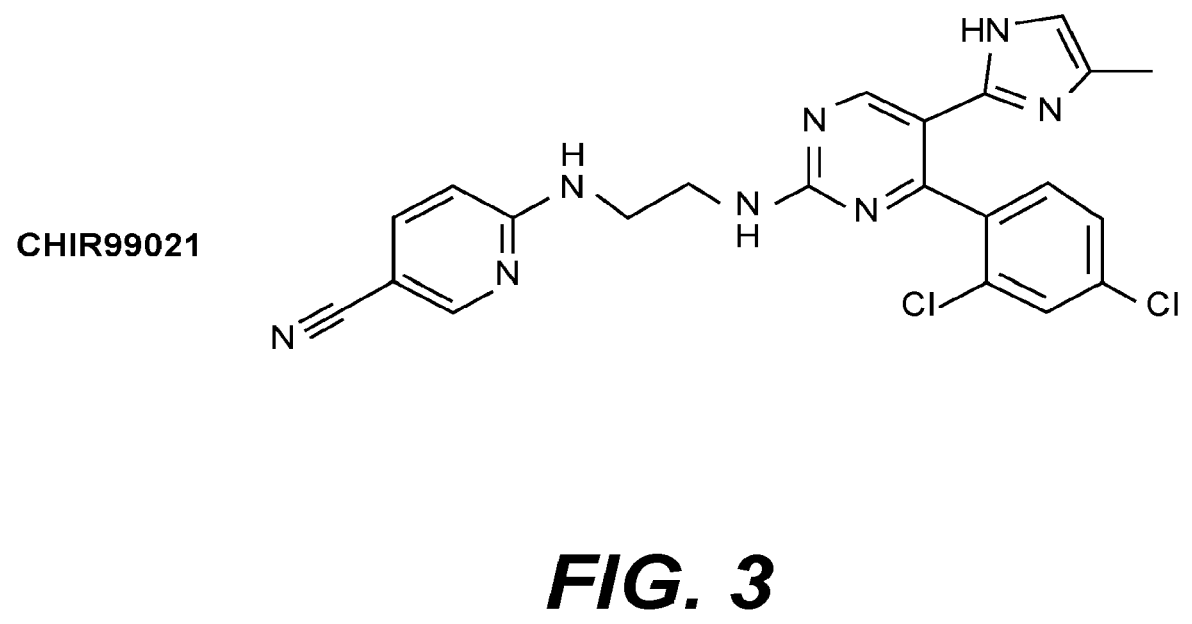

FIG. 3 shows the chemical structure of CHIR99021 in accordance with the present disclosure;

Figure 4:
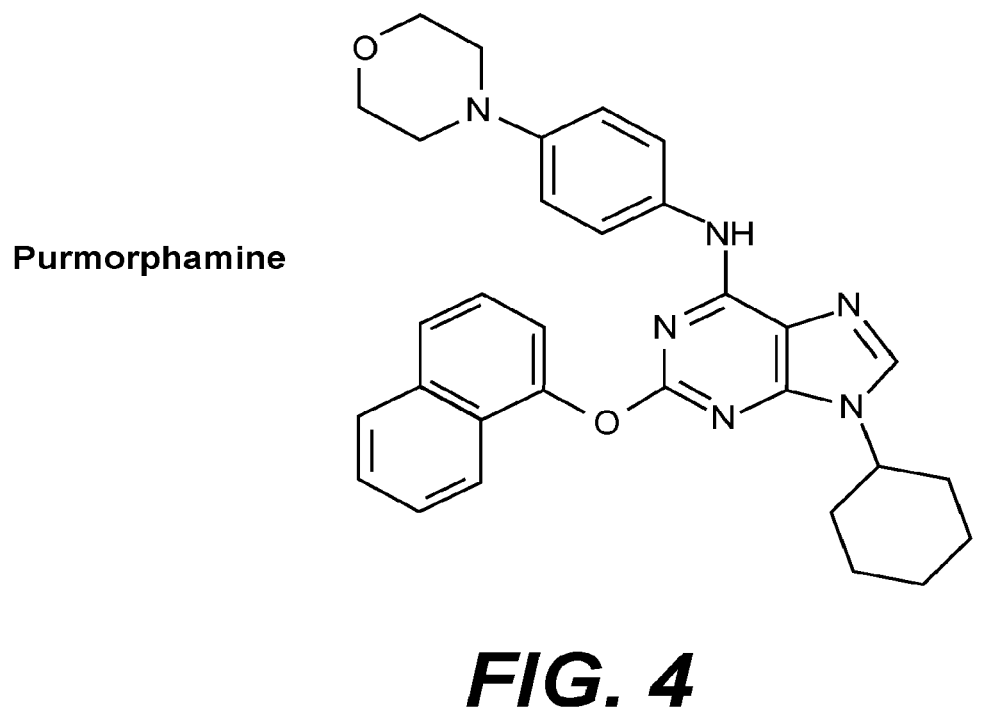

FIG. 4 shows the chemical structure of Purmorphamine in accordance with the present disclosure;

FIG. 6A, right panel is a representative pictograph of H1 hESC-derived OPCs generated by a method comprising pretreating undifferentiated cells in accordance with the present disclosure, showing no cyst formations in an in vitro cyst assay according to the present disclosure;

DETAILED DESCRIPTION

Figure 5:
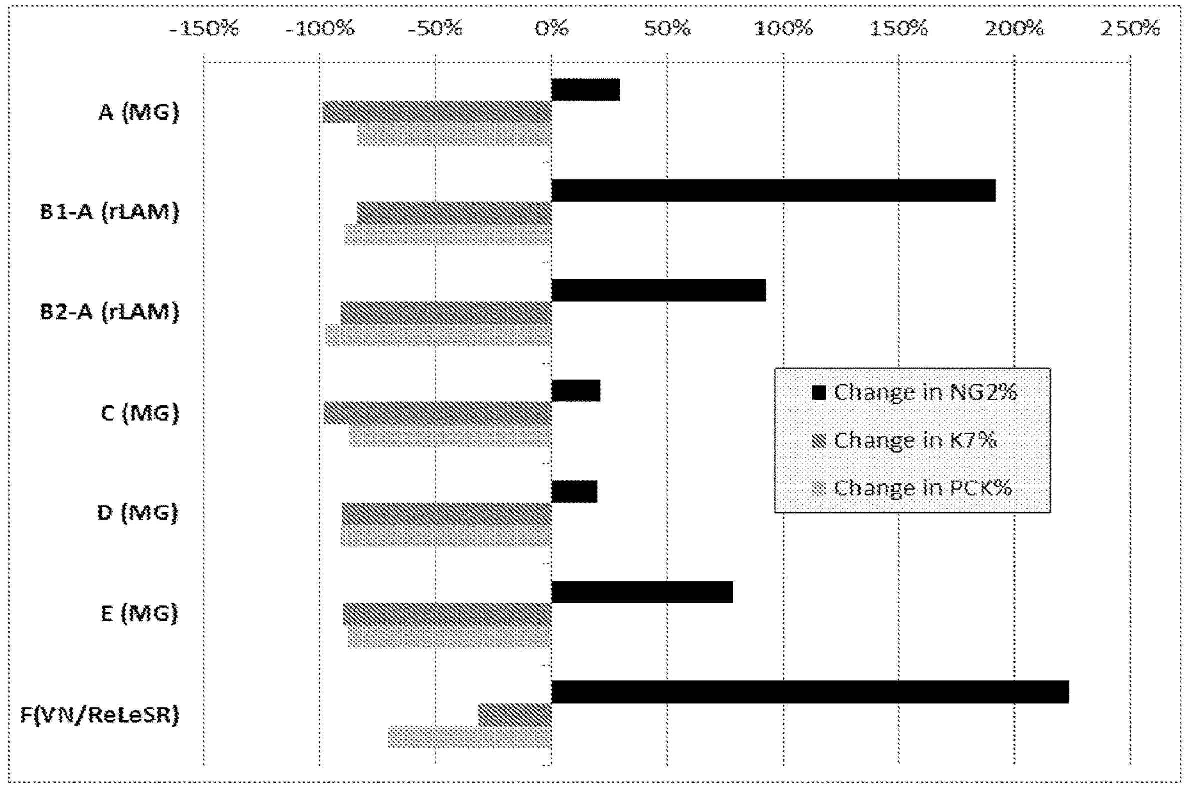
FIG. 5 shows representative comparisons of changes in NG2, K7, and PCK marker levels expressed in OPCs generated by a method in accordance with embodiments of the present disclosure as compared to matched controls generated by a method without pretreating undifferentiated cells.

This description is not intended to be a detailed catalog of all the different ways in which the disclosure may be implemented, or all the features that may be added to the instant disclosure. For example, features illustrated with respect to one aspect may be incorporated into other aspects, and features illustrated with respect to a particular aspect may be deleted from that aspect. Thus, the disclosure contemplates that in some aspects of the disclosure, any feature or combination of features set forth herein can be excluded or omitted. In addition, numerous variations and additions to the various aspects suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular aspects of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects only and is not intended to be limiting of the disclosure.

All publications, patent applications, patents and other references cited herein are incorporated by reference in their entireties.

Unless the context indicates otherwise, it is specifically intended that the various features of the disclosure described herein can be used in any combination. Moreover, the present disclosure also contemplates that in some aspects of the disclosure, any feature or combination of features set forth herein can be excluded or omitted.

Methods disclosed herein can comprise one or more steps or actions for achieving the described method. The method steps and/or actions may be interchanged with one another without departing from the scope of the present invention. In other words, unless a specific order of steps or actions is required for proper operation of the aspect, the order and/or use of specific steps and/or actions may be modified without departing from the scope of the present invention.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a percentages, density, volume and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, "oligodendrocyte progenitor cells" (OPCs) refer to cells of a neuroectoderm/glial lineage having the characteristics of a cell type found in the central nervous system, capable of differentiating into oligodendrocytes. These cells typically express the characteristic markers Nestin, NG2, and PDGF-Rα.

As used herein, the phrase "ectopic tissue" refers to tissue with unwanted or unexpected characteristics. When used in the context of defining a composition comprising OPCs, "ectopic tissue" refers to tissue not derived from the neuroectoderm lineage. More specifically, "ectopic tissue" is tissue resembling epithelium, epithelial cysts, mesothelial-derived tissue, cartilage, bone, or other tissues not typically found in the central nervous system.

As used herein, the term "undesirable cell types" refers to cells outside of the neuroectoderm lineage that result in the formation of ectopic tissues upon implantation, or that result in the formation of one or more cysts in a cyst assay, as described herein. More specifically, "undesirable cell types" include cells expressing the K7 and/or PCK markers. In an aspect, "undesirable cells types" can include epithelial lineage cells. In an aspect, "undesirable cell types" can include cells expressing markers that are characteristic of a trophoblastic lineage, such as Hand1.

The terms "K7," "Keratin 7" and "Cytokeratin 7" are used interchangeably herein and refer to a protein that is encoded by the KRT7 gene, or any variant thereof.

The terms "PCK" and "Pan-Cytokeratin" are used interchangeably herein and broadly refer to any member of the family of cytokeratin proteins, including but not limited to, acidic and basic (type I and type II) subfamilies of cytokeratin, as well as variants thereof. Non-limiting examples of PCK proteins include those proteins that are bound by the AE1/AE3 monoclonal antibody cocktail (Millipore Cat. no. MAB3412).

As used herein, "epithelial lineage cells" refer to cells derived from developmental precursors that are ectodermal, but have diverged from the neuroectoderm/glial lineage. In an aspect, "epithelial lineage cells" can be identified by one or more markers listed in TABLE 1. These cells include developmental progeny that have undergone an epithelial-mensenchymal transition (EMT) and epithelial-like cells derived from trophoblasts.

TABLE 1

Epithelial cellular markers.

| Cell Surface and Extracellular Markers | Intracellular Markers |
|---|---|
| A33 | Claudin-1 |
| ACE/CD143 | Claudin-3 |
| ALCAM/CD166 | Claudin-4 |
| Aminopeptidase B/RNPEP | Claudin-6 |
| Aminopeptidase Inhibitors | Claudin-10a |
| Aminopeptidase N/CD13 | Claudin-10b |
| Amnionless | Claudin-12 |
| B7-H1/PD-L1 | Claudin-17 |
| B7-H2 | Claudin-19 |
| B7-H3 | Cornulin |
| ClqTNE5 | Cytokeratin 7 |
| CA125/MUC16 | Cytokeratin 8 |
| CA15-3/MUC-1 | Cytokeratin 14 |
| CDH1/E-Cadherin | Cytokeratin 18 |
| CD1a | Cytokeratin 19 |
| CD1d | FoxJ1 |
| CD1d1 | FoxN1 |
| CD46 | KLF4 |
| CD74 | KLFS |
| CEACAM-1/CD66a | KLF10 |
| CEACAM-3/CD66d | Pan-cytokeratin |
| CEACAM-4 | TCF7L1/TCF3 |
| CEACAM-5/CD66e | |
| CEACAM-6/CD66c | |
| CEACAM-7 | |
| Collagen I | |
| Cubilin | |
| DDR1 | |
| beta-Defensin 2 | |
| beta-Defensin 3 | |
| alpha-Defensin 1 | |
| Endorepellin/Perlecan | |
| EpCAM/TROP1 | |
| Fas Ligand/TNFSF6 | |
| Gastrokine 1 | |
| HIN-1/SCGB3A1 | |
| Hyaluronan | |
| IGSF4C/SynCAM4 | |
| Integrin alpha 4/CD49d | |
| Integrin alpha 4 beta 1 | |
| Integrin alpha 4 beta 7/LPAM-1 | |
| Integrin alpha 6/CD49f | |
| JAM-A | |
| JAM-B/VE-JAM | |
| JAM-C | |
| L1CAM | |
| Laminin-1 | |
| MFG-E8 | |
| MSP R/Ron | |
| MUC-1 | |
| MUC-19 | |
| MUC-4 | |
| Nectin-1 | |
| Nectin-2/CD112 | |
| Nectin-3 | |
| Nectin-4 | |
| Nidogen-1/Entactin | |

TABLE 1-continued

| Epithelial cellular markers. | |
|---|---|
| Cell Surface and Extracellular Markers | Intracellular Markers |
| Occludin | |
| PLET-1 | |
| P1GF | |
| Prostasin/Prss8 | |
| TfR (Transferrin R) | |
| UGRP1/SCGB3A2 | |

As used herein, the phrase "cell enrichment" refers to the purification of desired cell types, in this instance OPCs, away from undesired cell types. Purification can be a positive selection (targeting OPCs) or a negative selection (targeting undesirable cell types).

Antibodies may be used to bind and physically remove the targeted cell types. Antibodies may be coupled to solid surfaces to effect the physical separation. The solid surfaces are typically magnetic beads, columns, or flasks.

As used herein, "implantation" or "transplantation" refers to the administration of a cell population into a target tissue using a suitable delivery technique, (e.g., using an injection device).

As used herein, a "subject" refers to an animal or a human.

As used herein, a "subject in need thereof" refers to an animal or a human having damaged tissue in the central nervous system. In an aspect, an animal or a human is experiencing a loss of motor function.

The terms "central nervous system" and "CNS" as used interchangeably herein refer to the complex of nerve tissues that control one or more activities of the body, which include but are not limited to, the brain and the spinal cord in vertebrates.

As used herein, "treatment" or "treating," with respect to a condition or a disease, is an approach for obtaining beneficial or desired results including preferably clinical results after a condition or a disease manifests in a patient. Beneficial or desired results with respect to a disease include, but are not limited to, one or more of the following: improving a condition associated with a disease, curing a disease, lessening severity of a disease, delaying progression of a disease, alleviating one or more symptoms associated with a disease, increasing the quality of life of one suffering from a disease, prolonging survival, and any combination thereof. Likewise, for purposes of this disclosure, beneficial or desired results with respect to a condition include, but are not limited to, one or more of the following: improving a condition, curing a condition, lessening severity of a condition, delaying progression of a condition, alleviating one or more symptoms associated with a condition, increasing the quality of life of one suffering from a condition, prolonging survival, and any combination thereof.

Methods of Differentiating Pluripotent Stem Cells

An aspect of the disclosure includes a method of differentiating pluripotent stem cells. In an aspect, a method of producing a population of cells that comprises a plurality of neural cells is provided. In an aspect, a method of producing populations of cells that comprise a plurality of OPCs is provided. In an aspect, a method of producing populations of cells that comprise a plurality of OPCs that are the in vitro differentiated progeny of human embryonic stem cells is provided. In an aspect, a method of producing populations of cells that comprise a plurality of OPCs that are the in vitro differentiated progeny of primate pluripotent stem cells is provided. In an aspect, a method of producing populations of cells that comprise a plurality of OPCs that are the in vitro differentiated progeny of induced pluripotent stem cells is provided. In an aspect, a method of differentiating pluripotent stem cells comprises one or more steps directed to pretreating a plurality of undifferentiated stem cells. In an aspect, a method comprising one or more pretreatment steps is capable of producing a population of cells that comprises a reduced level of undesirable cell types. In an aspect, a method comprising one or more pretreatment steps is capable of producing a population of cells comprising a plurality of OPCs having less than about 15% undesirable cell types. In an aspect, a method comprising one or more pretreatment steps is capable of producing a population of cells that comprises a plurality of OPCs, wherein the population of cells is capable of forming less than or equal to one epithelial cyst per 100,000 cells in a cyst assay in accordance to the present disclosure.

Propagation and Culture of Undifferentiated Pluripotent Stem Cells

In an aspect, a method can be carried out on a pluripotent stem cell line. In another aspect, a method can be carried out on an embryonic stem cell line. In an aspect, a method can be carried out on a plurality of undifferentiated stem cells that are derived from an H1, H7, H9, H13, or H14 cell line. In another aspect, undifferentiated stem cells can be derived from an induced pluripotent stem cell (iPS) line. In an aspect, a method can be carried out on a primate pluripotent stem (pPS) cell line. In yet another aspect, undifferentiated stem cells can be derived from parthenotes, which are embryos stimulated to produce hESCs without fertilization.

Methods of propagation and culture of undifferentiated pluripotent stem cells have been previously described. With respect to tissue and cell culture of pluripotent stem cells, the reader may wish to refer to any of numerous publications available in the art, e.g., *Teratocarcinomas and Embryonic Stem cells: A Practical Approach* (E. J. Robertson, Ed., IRL Press Ltd. 1987); *Guide to Techniques in Mouse Development* (P. M. Wasserman et al., Eds., Academic Press 1993); *Embryonic Stem Cell Differentiation in Vitro* (M. V. Wiles, Meth. Enzymol. 225:900, 1993); *Properties and Uses of Embryonic Stem Cells: Prospects for Application to Human Biology and Gene Therapy* (P. D. Rathjen et al., Reprod. Fertil. Dev. 10:31, 1998; and R. I. Freshney, Culture of Animal Cells, Wiley-Liss, New York, 2000).

In one aspect, undifferentiated pluripotent stem cells can be maintained in an undifferentiated state without added feeder cells (see, e.g., (2004) Rosler et al., *Dev. Dynam.* 229:259). Feeder-free cultures are typically supported by a nutrient medium containing factors that promote proliferation of the cells without differentiation (see, e.g., U.S. Pat. No. 6,800,480). In one aspect, conditioned media containing such factors can be used. Conditioned media can be obtained by culturing the media with cells secreting such factors. Suitable cells include, but are not limited to, irradiated (~4,000 Rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium, such as knock-out DMEM supplemented with 20% serum replacement and 4 ng/mL bFGF. Medium that has been conditioned for 1-2 days can be supplemented with further bFGF, and used to support pPS cell culture for 1-2 days (see. e.g., WO 01/51616; Xu et al., (2001) *Nat. Biotechnol.* 19:971).

Alternatively, fresh or non-conditioned medium can be used, which has been supplemented with added factors (like a fibroblast growth factor or forskolin) that promote proliferation of the cells in an undifferentiated form. Non-limiting examples include a base medium like X-VIVO™ 10 (Lonza, Walkersville, Md.) or QBSF™-60 (Quality Biological Inc. Gaithersburg, Md.), supplemented with bFGF at 40-80 ng/mL, and optionally containing SCF (15 ng/ml), or Flt3 ligand (75 ng/ml) (see, e.g., Xu et al., (2005) *Stem Cells* 23(3):315). These media formulations have the advantage of supporting cell growth at 2-3 times the rate in other systems (see, e.g., WO 03/020920). In one aspect, undifferentiated pluripotent cells such as hES cells, can be cultured in a media comprising bFGF and TGFβ. Non-limiting example concentrations of bFGF include about 80 ng/ml. Non-limiting example concentrations of TGFβ include about 0.5 ng/ml.

In one aspect, undifferentiated pluripotent cells can be cultured on a layer of feeder cells, typically fibroblasts derived from embryonic or fetal tissue (Thomson et al. (1998) *Science* 282:1145). In one aspect, feeder cells can be derived from a human or a murine source. Human feeder cells can be isolated from various human tissues, or can be derived via differentiation of human embryonic stem cells into fibroblast cells (see, e.g., WO 01/51616). In one aspect, human feeder cells that can be used include, but are not limited to, placental fibroblasts (see, e.g., Genbacev et al. (2005) *Fertil. Steril.* 83(5): 1517), fallopian tube epithelial cells (see, e.g., Richards et al. (2002) *Nat. Biotechnol.,* 20:933), foreskin fibroblasts (see, e.g., Amit et al. (2003) *Biol. Reprod.* 68:2150), and uterine endometrial cells (see, e.g., Lec et al. (2005) *Biol. Reprod.* 72(1):42).

Various solid surfaces can be used in the culturing of undifferentiated pluripotent cells. Those solid surfaces include, but are not limited to, standard commercially available cell culture plates, such as 6-well, 24-well, 96-well, or 144-well plates. Other solid surfaces include, but are not limited to, microcarriers and disks. Solid surfaces suitable for growing undifferentiated pluripotent cells can be made of a variety of substances including, but not limited to, glass or plastic such as polystyrene, polyvinylchloride, polycarbonate, polytetrafluorethylene, melinex, thermanox, or combinations thereof. In one aspect, suitable surfaces can comprise one or more polymers, such as, e.g., one or more acrylates. In one aspect, a solid surface can be three-dimensional in shape. Non-limiting examples of three-dimensional solid surfaces are described, e.g., in U.S. Patent Pub. No. 2005/0031598.

In an aspect, undifferentiated stem cells can be grown under feeder-free conditions on a growth substrate. In an aspect, a growth substrate can be a Matrigel® matrix (e.g., Matrigel®, Matrigel® GFR), recombinant Laminin, or Vitronectin. In an aspect, undifferentiated stem cells can be subcultured using various methods such as using collagenase, or such as manual scraping. In another aspect, undifferentiated stem cells can be subcultured using non-enzymatic means, such as 0.5 mM EDTA in PBS, or such as using ReLeSR™. In an aspect, a plurality of undifferentiated stem cells are seeded or subcultured at a seeding density that allows the cells to reach confluence in about three to about ten days. In an aspect, the seeding density can range from about $6.0\times10^3$ cells/cm$^2$ to about $5.0\times10^5$ cells/cm$^2$, such as about $1.0\times10^4$ cells/cm$^2$, such as about $5.0\times10^4$ cells/cm$^2$, such as about $1.0\times10^5$ cells/cm$^2$, or such as about $3.0\times10^5$ cells/cm$^2$ of growth surface. In another aspect, the seeding density can range from about $6.0\times10^3$ cells/cm$^2$ to about $1.0\times10^4$ cells/cm$^2$ of growth surface, such as about $6.0\times10^3$ cells/cm$^2$ to about $9.0\times10^3$ cells/cm$^2$, such as about $7.0\times10^3$ cells/cm$^2$ to about $1.0\times10^4$ cells/cm$^2$, such as about $7.0\times10^3$ cells/cm$^2$ to about $9.0\times10^3$ cells/cm$^2$, or such as about $7.0\times10^3$ cells/cm$^2$ to about $8.0\times10^3$ cells/cm$^2$ of growth surface. In yet another aspect, the seeding density can range from about $1.0\times10^4$ cells/cm$^2$ to about $1.0\times10^5$ cells/cm$^2$ of growth surface, such as about $2.0\times10^4$ cells/cm$^2$ to about $9.0\times10^4$ cells/cm$^2$, such as about $3.0\times10^4$ cells/cm$^2$ to about $8.0\times10^4$ cells/cm$^2$, such as about $4.0\times10^4$ cells/cm$^2$ to about $7.0\times10^4$ cells/cm$^2$, or such as about $5.0\times10^4$ cells/cm$^2$ to about $6.0\times10^4$ cells/cm$^2$ of growth surface. In an aspect, the seeding density can range from about $1.0\times10^5$ cells/cm$^2$ to about $5.0\times10^5$ cells/cm$^2$ of growth surface, such as about $1.0\times10^5$ cells/cm$^2$ to about $4.5\times10^5$ cells/cm$^2$, such as about $1.5\times10^5$ cells/cm$^2$ to about $4.0\times10^5$ cells/cm$^2$, such as about $2.0\times10^5$ cells/cm$^2$ to about $3.5\times10^5$ cells/cm$^2$, or such as about $2.5\times10^5$ cells/cm$^2$ to about $3.0\times10^5$ cells/cm$^2$ of growth surface.

Any of a variety of suitable cell culture and sub-culturing techniques can be used to culture cells in accordance with an aspect of a subject method. For example, in an aspect, a culture medium can be exchanged at a suitable time interval. In one aspect, a culture medium can be completely exchanged daily, initiating about 2 days after sub-culturing of the cells. In an aspect, when a culture reaches about 90% colony coverage, a surrogate flask can be sacrificed and enumerated using one or more suitable reagents, such as, e.g., Collagenase IV and 0.05% Trypsin-EDTA in series to achieve a single cell suspension for quantification. In an aspect, a plurality undifferentiated stem cells can then be sub-cultured before seeding the cells on a suitable growth substrate (e.g., a Matrigel® matrix) at a seeding density that allows the cells to reach confluence over a suitable period of time, such as, e.g., in about three to ten days. In one aspect, undifferentiated stem cells can be subcultured using Collagenase IV and expanded on a recombinant laminin matrix. In one aspect, undifferentiated stem cells can be subcultured using Collagenase IV and expanded on a Matrigel® matrix. In one aspect, undifferentiated stem cells can be subcultured using ReLeSR™ and expanded on a Vitronectin matrix.

In an aspect, the seeding density can range from about $6.0\times10^3$ cells/cm$^2$ to about $5.0\times10^5$ cells/cm$^2$, such as about $1.0\times10^4$ cells/cm$^2$, such as about $5.0\times10^4$ cells/cm$^2$, such as about $1.0\times10^5$ cells/cm$^2$, or such as about $3.0\times10^5$ cells/cm$^2$ of growth surface. In another aspect, the seeding density can range from about $6.0\times10^3$ cells/cm$^2$ to about $1.0\times10^4$ cells/cm$^2$ of growth surface, such as about $6.0\times10^3$ cells/cm$^2$ to about $9.0\times10^3$ cells/cm$^2$, such as about $7.0\times10^3$ cells/cm$^2$ to about $1.0\times10^4$ cells/cm$^2$, such as about $7.0\times10^3$ cells/cm$^2$ to about $9.0\times10^3$ cells/cm$^2$, or such as about $7.0\times10^3$ cells/cm$^2$ to about $8.0\times10^3$ cells/cm$^2$ of growth surface. In yet another aspect, the seeding density can range from about $1.0\times10^4$ cells/cm$^2$ to about $1.0\times10^5$ cells/cm$^2$ of growth surface, such as about $2.0\times10^4$ cells/cm$^2$ to about $9.0\times10^4$ cells/cm$^2$, such as about $3.0\times10^4$ cells/cm$^2$ to about $8.0\times10^4$ cells/cm$^2$, such as about $4.0\times10^4$ cells/cm$^2$ to about $7.0\times10^4$ cells/cm$^2$, or such as about $5.0\times10^4$ cells/cm$^2$ to about $6.0\times10^4$ cells/cm$^2$ of growth surface. In an aspect, the seeding density can range from about $1.0\times10^5$ cells/cm$^2$ to about $5.0\times10^5$ cells/cm$^2$ of growth surface, such as about $1.0\times10^5$ cells/cm$^2$ to about $4.5\times10^5$ cells/cm$^2$, such as about $1.5\times10^5$ cells/cm$^2$ to about $4.0\times10^5$ cells/cm$^2$, such as about $2.0\times10^5$ cells/cm$^2$ to about $3.5\times10^5$ cells/cm$^2$, or such as about $2.5\times10^5$ cells/cm$^2$ to about $3.0\times10^5$ cells/cm$^2$ of growth surface.

Pretreatment of Undifferentiated Pluripotent Stem Cells

In another aspect, a method is provided that involves pretreatment of undifferentiated stem cells, prior to differentiation. Without being held to any particular theory, the inventors have identified various pretreatment steps that can facilitate a further reduction of spontaneous differentiation of pluripotent stem cells, thereby further improving upon differentiation methods that do not involve pretreatment steps. In an aspect, a method that involves one or more pretreatment steps described herein can produce a population of cells comprising low levels of undesirable trophoblast lineage cells. In another aspect, a method that involves one or more pretreatment steps described herein can produce a population of cells comprising low levels of undesirable epithelial lineage cells. Furthermore, the inventors have identified various pretreatment steps that can facilitate production of a population of cells that forms less than or equal to one epithelial cyst per 100,000 cells in a cyst assay in accordance to the present disclosure. The pretreatment steps are described in detail herein.

In an aspect, a method comprises incubating expanded but undifferentiated stem cells for a period of time with one or more stem cell differentiation modulating molecules. In an aspect, a stem cell differentiation modulating molecule can be a molecule that drives subsequent cell differentiation away from the epithelial lineage. Without being held to theory, the inventors have identified that incubating stem cells with one or more stem cell differentiation modulating molecules can result in reduction of epithelial lineage cells. In an aspect, a method comprises incubating expanded but undifferentiated stem cells for a period of time with one or more of the following four types of stem cell differentiation modulating molecules: (1) an inhibitor of ALK5, which is a part of the SMAD/TGFβ-RII signaling pathway; (2) an inhibitor of ALK2, which is a part of the BMPRI signaling pathway; (3) a GSK3 inhibitor for activating the WNT signaling pathway; and (4) a Smoothened agonist for activating the SHH pathway.

Figure 1:
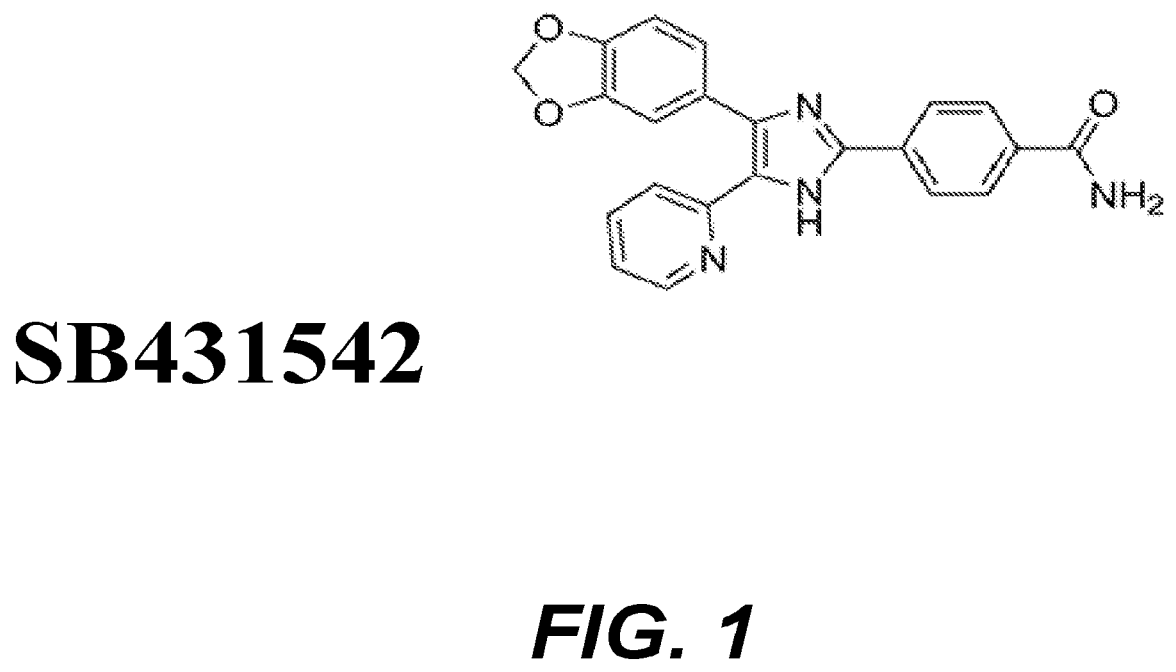

In an aspect, a method comprises incubating expanded but undifferentiated stem cells with one or more stem cell differentiation modulators. In an aspect, a stem cell differentiation modulator can be a small molecule. In an aspect, a small molecule stem cell differentiation modulator is an inhibitor of ALK5, ALK2, or GSK3, or is a Smoothened agonist. In an aspect, an inhibitor of ALK5 can be selected from the group consisting of SB431542, LY364947, RepSox, and derivatives thereof. In another aspect, an inhibitor of ALK2 can be selected from the group consisting of Dorsomorphin, LDN193189, Noggin protein, and derivatives thereof. In yet another aspect, an inhibitor of GSK3 can be selected from the group consisting of CHIR99021, 6-Bromoindirubin-3'-oxime (BIO), Kenpaullone, SB216762, Wnt protein, and derivatives thereof. In an aspect, a Smoothened agonist can be selected from the group consisting of Purmorphamine, SAG (CAS 364590-63-6), SSH protein, and derivatives thereof. In an aspect, a method comprises incubating expanded but undifferentiated stem cells for a period of time with four small molecules: SB431542, Dorsomorphin, CHIR99021, and Purmorphamine. The chemical structures of SB431542, Dorsomorphin, CHIR99021, and Purmorphamine are depicted in FIG. 1 through FIG. 4, respectively.

In an aspect, a method comprises incubating expanded but undifferentiated stem cells for a period of time with one or more stem cell differentiation modulators, as described herein. In an aspect, a method comprises incubating expanded but undifferentiated stem cells for a period of time with two or more stem cell differentiation modulators. In an aspect, a method comprises incubating expanded but undifferentiated stem cells for a period of time with three or more stem cell differentiation modulators. In an aspect, a method comprises incubating expanded but undifferentiated stem cells for a period of time with four or more stem cell differentiation modulators. In an aspect, an incubation period can range from about one to about ten days, such as about two days, such as about three days, such as about four days, such as about five days, such as about six days, such as about seven days, such as about eight days, or such as about nine days. In an aspect, an incubation period can range from about one to about five days, such as about one to about three days, or such as about two to about five days. In another aspect, an incubation period can range from about six to about ten days, such as about six to about eight days, or such as about seven to about ten days. In yet another aspect, an incubation period can range from about three to about eight days, such as about three to about five days, such as about four to about six days, such as about five to about seven days, or such as about six to about eight days.

In an aspect, a method comprises incubating a population of expanded but undifferentiated stem cells for a first incubation period with two or more first stem cell differentiation modulators, and incubating the population for a second incubation period with two or more second stem cell differentiation modulators. In an aspect, a first incubation period can range from about one to about seven days, such as about two days, such as about three days, such as about four days, such as bout five days, or such as about six days. In an aspect, a second incubation period can range from about one to about seven days, such as about two days, such as about three days, such as about four days, such as about five days, or such as about six days.

In an aspect, the two or more first stem cell differentiation modulators are different from the two or more second stem cell differentiation modulators. In an aspect, the two or more first stem cell modulators are the same as the two or more second stem cell modulators. In an aspect, the first and second stem cell modulators share at least one common modulator. In an aspect, the first and second stem cell modulators share two or more common modulators, such as three or more common modulators, such as four or more common modulators.

In an aspect, a method comprises incubating expanded but undifferentiated stem cells for about 1 to 10 days with one or more of the following differentiation modulators: SB431542, Dorsomorphin, CHIR99021, and Purmorphaminc. In an aspect, a method comprises incubating expanded but undifferentiated stem cells for about 1 to 5 days with SB431542, Dorsomorphin, CHIR99021, and Purmorphamine, followed by an incubation for about 1 to 5 days with CHIR99021 and Purmorphaminc.

In an aspect, a method comprises incubating expanded but undifferentiated stem cells for about four days with SB431542, Dorsomorphin, CHIR99021, and Purmorphaminc, followed by an incubation for 3 days with CHIR99021 and Purmorphaminc.

In an aspect, a method comprises incubating expanded but undifferentiated ESCs with SB431542 at a concentration that ranges from about 1 μM to about 100 μM, such as about 5 μM, about 10 μM, such as about 15 μM, such as about 20 μM, such as about 25 μM, such as about 30 μM, such as about 35 μM, such as about 40 μM, such as about 45 μM, such as about 50 μM, such as about 55 μM, such as about 60 μM, such as about 65 μM, such as about 70 μM, such as about 75 μM, such as about 80 μM, such as about 85 μM, such as about 90 μM, or such as about 95 μM. In another aspect, a method comprises incubating expanded but undifferentiated ESCs with SB431542 at a concentration that ranges from about 1 μM to about 20 μM, such as about 1 μM to about 13 μM, such as about 8 μM to about 20 μM, such as about 8 μM to about 13 μM, or such as about 9 μM to about 11 μM. In yet another aspect, a method comprises incubating expanded but undifferentiated ESCs with SB431542 at a concentration that ranges from about 20 μM to about 40 μM, such as about 20 μM to about 33 μM, such as about 28 μM to about 40 μM, such as about 28 μM to about 33 μM, or such as about 29 μM to about 31 μM. In an aspect, a method comprises incubating expanded but undifferentiated ESCs with SB431542 at a concentration that ranges from about 40 μM to about 60 μM, such as about 40 μM to about 53 μM, such as about 48 μM to about 55 μM, such as about 48 μM to about 53 μM, or such as about 49 μM to about 51 μM. In an aspect, a method comprises incubating expanded but undifferentiated ESCs with SB431542 at a concentration that ranges from about 60 μM to about 80 μM, such as about 60 μM to about 73 μM, such as about 68 μM to about 75 μM, such as about 68 μM to about 73 μM, or such as about 69 μM to about 71 μM. In an aspect, a method comprises incubating expanded but undifferentiated ESCs with SB431542 at a concentration that ranges from about 80 μM to about 100 μM, such as about 80 μM to about 93 μM, such as about 88 μM to about 95 μM, such as about 88 μM to about 93 μM, or such as about 89 μM to about 91 μM. In an aspect, a method comprises incubating expanded but undifferentiated ESCs with SB431542 at a concentration of about 10 μM.

In an aspect, a method comprises incubating expanded but undifferentiated ESCs with an ALK5 inhibitor at a concentration that ranges from about 250 nM to about 250 μM, such as about 1 μM, about 10 μM, about 50 μM, about 100 μM, about 150 μM, or about 200 μM. In an aspect, a method comprises incubating expanded but undifferentiated ESCs with LY364947 at a concentration that ranges from about 250 nM to about 25 μM, such as about 250 nM to about 1 μM, such as about 1 μM to about 10 μM, or such as about 10 μM to about 25 μM. In an aspect, a method comprises incubating expanded but undifferentiated ESCs with LY364947 at about 2.5 μM. In another aspect, a method comprises incubating expanded but undifferentiated ESCs with RepSox at a concentration that ranges from about 2.5 μM to about 250 μM, such as about 2.5 μM to about 10 μM, such as about 10 μM to about 100 μM, or such as about 100 μM to about 250 μM. In an aspect, a method comprises incubating expanded but undifferentiated ESCs with RepSox at about 25 μM.

In an aspect, a method comprises incubating expanded but undifferentiated ESCs with Dorsomorphin at a concentration that ranges from about 0.2 μM to about 20 μM, such as about 0.5 μM, such as about 0.8 μM, such as about 1 μM, such as about 1.5 μM, such as about 2 μM, such as about 2.5 μM, such as about 3 μM, such as about 3.5 μM, such as about 4 μM, such as about 4.5 M, such as about 5 μM, such as about 5.5 μM, such as about 6 μM, such as about 6.5 μM, such as about 7 μM, such as about 7.5 μM, such as about 8 μM, such as about 8.5 μM, such as about 9 μM, such as about 10 μM, such as about 11 μM, such as about 12 μM, such as about 13 μM, such as about 14 μM, such as about 15 μM, such as about 16 μM, such as about 17 μM, such as about 18 μM, or such as about 19 μM. In another aspect, a method comprises incubating expanded but undifferentiated ESCs with Dorsomorphin at a concentration that ranges from about 0.2 μM to about 1 μM, such as about 0.2 μM to about 0.9 μM, such as about 0.3 μM to about 0.8 μM, such as about 0.4 μM to about 0.7 μM, or such as about 0.5 μM to about 0.6 μM. In yet another aspect, a method comprises incubating expanded but undifferentiated ESCs with Dorsomorphin at a concentration that ranges from about 1 μM to about 10 μM, such as about 1 μM to about 9 μM, such as about 2 μM to about 8 μM, such as about 3 μM to about 7 μM, or such as about 4 μM to about 6 μM. In an aspect, a method comprises incubating expanded but undifferentiated ESCs with Dorsomorphin at a concentration that ranges from about 10 μM to about 20 μM, such as about 10 μM to about 19 μM, such as about 12 μM to about 18 μM, such as about 13 μM to about 17 μM, or such as about 14 μM to about 16 μM. In an aspect, a method comprises incubating expanded but undifferentiated ESCs with Dorsomorphin at a concentration of about 2 μM.

In an aspect, a method comprises incubating expanded but undifferentiated ESCs with an ALK2 inhibitor at a concentration that ranges from about 1 nM to about 20 μM, such as about 10 nM, about 50 nM, about 100 nM, about 150 nM, about 200 nM, about 500 nM, about 1 μM, about 5 μM, about 10 μM, or about 15 μM. In an aspect, a method comprises incubating expanded but undifferentiated ESCs with LDN193189 at a concentration that ranges from about 1 nM to about 100 nM, such as about 1 nM to about 10 nM, such as about 10 nM to about 50 nM, or such as about 50 nM to about 100 nM. In an aspect, a method comprises incubating expanded but undifferentiated ESCs with LDN193189 at about 10 nM. In an aspect, a method comprises incubating expanded but undifferentiated ESCs with a Noggin protein at a concentration that ranges from about 2 nM to about 200 nM, such as about 2 nM to about 10 nM, such as about 10 nM to about 100 nM, or such as about 100 nM to about 200 nM. In an aspect, a method comprises incubating expanded but undifferentiated ESCs with a Noggin protein at about 20 nM.

In an aspect, a method comprises incubating expanded but undifferentiated ESCs with CHIR99021 at a concentration that ranges from about 0.3 μM to about 30 μM, such as about 0.5 μM, such as about 0.8 μM, such as about 1 μM, such as about 1.5 μM, such as about 2 μM, such as about 2.5 μM, such as about 3 μM, such as about 3.5 μM, such as about 4 μM, such as about 4.5 μM, such as about 5 μM, such as about 5.5 μM, such as about 6 μM, such as about 6.5 μM, such as about 7 μM, such as about 7.5 μM, such as about 8 μM, such as about 8.5 μM, such as about 9 μM, such as about 10 μM, such as about 11 μM, such as about 12 μM, such as about 13 μM, such as about 14 μM, such as about 15 μM, such as about 20 μM, or such as about 25 μM. In another aspect, a method comprises incubating expanded but undifferentiated ESCs with CHIR99021 at a concentration that ranges from about 0.3 μM to about 1 μM, such as about 0.3 μM to about 0.9 μM, such as about 0.4 μM to about 0.8 μM, or such as about 0.5 μM to about 0.7 μM. In yet another aspect, a method comprises incubating expanded but undifferentiated ESCs with CHIR99021 at a concentration that ranges from about 1 μM to about 10 μM, such as about 1 μM to about 9 μM, such as about 2 μM to about 8 μM, such as about 3 μM to about 7 μM, or such as about 4 μM to about 6 μM. In an aspect, a method comprises incubating expanded but undifferentiated ESCs with CHIR99021 at a concentration that ranges from about 10 μM to about 20 μM, such as about 11 μM to about 19 μM, such as about 12 μM to about 18 μM, such as about 13 μM to about 17 μM, or such as about 14 μM to about 16 μM. In an aspect, a method comprises incubating expanded but undifferentiated ESCs with CHIR99021 at a concentration that ranges from about 20 μM to about 30 μM, such as about 21 μM to about 29 μM, such as about 22 μM to about 28 μM, such as about 23 μM to about 27 μM, or such as about 24 μM to about 26 μM. In an aspect, a method comprises incubating expanded but undifferentiated ESCs with CHIR99021 at a concentration of about 3 μM.

In an aspect, a method comprises incubating expanded but undifferentiated ESCs with a GSK3 inhibitor at a concentration that ranges from about 25 nM to about 100 μM, such as about 100 nM, about 250 nM, about 500 nM, about 750 nM, about 1 μM, about 10 μM, or about 50 μM. In an aspect, a method comprises incubating expanded but undifferentiated ESCs with BIO (6-Bromoindirubin-3'-oxime) at a concentration that ranges from about 500 nM to about 50 μM, such as about 500 nM to about 1 μM, such as about 1 μM to about 10 μM, or such as about 10 μM to about 50 μM. In an aspect, a method comprises incubating expanded but undifferentiated ESCs with BIO (6-Bromoindirubin-3'-oxime) at about 5 μM. In another aspect, a method comprises incubating expanded but undifferentiated ESCs with Kenpaullone at a concentration that ranges from about 1 μM to about 100 μM, such as about 1 μM to about 10 μM, such as about 10 μM to about 50 μM, or such as about 50 μM to about 100 μM. In an aspect, a method comprises incubating expanded but undifferentiated ESCs with Kenpaullone at about 10 μM. In another aspect, a method comprises incubating expanded but undifferentiated ESCs with SB216763 at a concentration that ranges from about 500 nM to about 50 μM, such as about 500 nM to about 1 μM, such as about 1 μM to about 10 μM, or such as about 10 μM to about 50 μM. In an aspect, a method comprises incubating expanded but undifferentiated ESCs with SB216763 at about 5 μM. In yet another aspect, a method comprises incubating expanded but undifferentiated ESCs with a Wnt protein at a concentration that ranges from about 25 nM to about 2.5 μM, such as about 25 nM to about 100 nM, such as about 100 nM to about 1 μM, or such as about 1 μM to about 2.5 μM. In an aspect, a method comprises incubating expanded but undifferentiated ESCs with a Wnt protein at about 250 nM.

In an aspect, a method comprises incubating expanded but undifferentiated ESCs with Purmorphamine at a concentration that ranges from about 0.05 μM to about 5 μM, such as about 0.08 μM, such as about 0.1 μM, such as about 0.2 μM, such as about 0.3 μM, such as about 0.4 μM, such as about 0.5 μM, such as about 0.6 μM, such as about 0.7 μM, such as about 0.8 μM, such as about 0.9 μM, such as about 1 μM, such as about 2 μM, such as about 3 μM, such as about 4 μM. In another aspect, a method comprises incubating expanded but undifferentiated ESCs with Purmorphamine at a concentration that ranges from about 0.05 μM to about 0.1 μM, such as about 0.06 μM to about 0.09 μM, or such as about 0.07 UM to about 0.08 μM. In another aspect, a method comprises incubating expanded but undifferentiated ESCs with Purmorphamine at a concentration that ranges from about 0.1 μM to about 1 μM, such as about 0.2 μM to about 0.9 μM, such as about 0.3 μM to about 0.8 μM, such as about 0.4 μM to about 0.7 μM, or such as about 0.5 μM to about 0.6 μM. In another aspect, a method comprises incubating expanded but undifferentiated ESCs with Purmorphamine at a concentration that ranges from about 1 μM to about 5 μM, such as about 1 μM to about 4 μM, such as about 2 μM to about 5 μM, or such as about 2 μM to about 4 μM. In an aspect, a method comprises incubating expanded but undifferentiated ESCs with Purmorphamine at a concentration of about 0.5 μM.

In an aspect, a method comprises incubating expanded but undifferentiated ESCs with a Smoothened agonist at a concentration that ranges from about 2.5 nM to about 5 μM, such as about 50 nM, about 100 nM, about 250 nM, about 500 nM, about 750 nM, about 1 μM, or about 2.5 μM. In an aspect, a method comprises incubating expanded but undifferentiated ESCs with SAG at a concentration that ranges from about 10 nM to about 1 μM, such as about 10 nM to about 100 nM, such as about 100 nM to about 500 nM, or such as about 500 nM to about 1000 nM. In an aspect, a method comprises incubating expanded but undifferentiated ESCs with SAG at about 100 nM. In an aspect, a method comprises incubating expanded but undifferentiated ESCs with an SHH protein at a concentration that ranges from about 2.5 nM to about 250 nM, such as about 2.5 nM to about 10 nM, such as about 10 nM to about 100 nM, or such as about 100 nM to about 250 nM. In an aspect, a method comprises incubating expanded but undifferentiated ESCs with an SHH protein at about 25 nM.

In an aspect, undifferentiated stem cells can be expanded on a growth substrate in preparation for pretreatment. Non-limiting examples of growth substrates include Matrigel® matrix, recombinant Laminin (e.g., recombinant Laminin 521), and Vitronectin. In an aspect, the medium can be completely exchanged daily initiating about 2 days after subculturing of the undifferentiated stem cells. In an aspect, undifferentiated stem cells can be subcultured using collagenase and manual scraping or other non-enzymatic means such as 0.5 mM EDTA in PBS or ReLeSR™. In an aspect, the undifferentiated stem cells are seeded or subcultured at a seeding density that allows the cells to reach confluence in about three to about ten days. In an aspect, the seeding density can range from about $6.0\times10^3$ cells/cm$^2$ to about $5.0\times10^5$ cells/cm$^2$, such as about $1.0\times10^4$ cells/cm$^2$, such as about $5.0\times10^4$ cells/cm$^2$, such as about $1.0\times10^5$ cells/cm$^2$, or such as about $3.0\times10^5$ cells/cm$^2$ of growth surface in the subculture passage prior to the initiation of differentiation. In another aspect, the seeding density can range from about $6.0\times10^3$ cells/cm$^2$ to about $1.0\times10^4$ cells/cm$^2$ of growth surface, such as about $6.0\times10^3$ cells/cm$^2$ to about $9.0\times10^3$ cells/cm$^2$, such as about $7.0\times10^3$ cells/cm$^2$ to about $1.0\times10^4$ cells/cm$^2$, such as about $7.0\times10^3$ cells/cm$^2$ to about $9.0\times10^3$ cells/cm$^2$, or such as about $7.0\times10^3$ cells/cm$^2$ to about $8.0\times10^3$ cells/cm$^2$ of growth surface. In yet another aspect, the seeding density can range from about $1.0\times10^4$ cells/cm$^2$ to about $1.0\times10^5$ cells/cm$^2$ of growth surface, such as about $2.0\times10^4$ cells/cm$^2$ to about $9.0\times10^4$ cells/cm$^2$, such as about $3.0\times10^4$ cells/cm$^2$ to about $8.0\times10^4$ cells/cm$^2$, such as about $4.0\times10^4$ cells/cm$^2$ to about $7.0\times10^4$ cells/cm$^2$, or such as about $5.0\times10^4$ cells/cm$^2$ to about $6.0\times10^4$ cells/cm$^2$ of growth surface. In an aspect, the seeding density can range from about $1.0\times10^5$ cells/cm$^2$ to about $5.0\times10^5$ cells/cm$^2$ of growth surface, such as about $1.0\times10^5$ cells/cm$^2$ to about $4.5\times10^5$ cells/cm$^2$, such as about $1.5\times10^5$ cells/cm$^2$ to about $4.0\times10^5$ cells/cm$^2$, such as about $2.0\times10^5$ cells/cm$^2$ to about $3.5\times10^5$ cells/cm$^2$, or such as about $2.5\times10^5$ cells/cm$^2$ to about $3.0\times10^5$ cells/cm$^2$ of growth surface in the subculture passage prior to the initiation of the differentiation. In an aspect, once the undifferentiated stem cells have reached 30-50% confluence, the medium is changed to a glial progenitor medium that contains one or more stem cell differentiation modulators as described herein. In an aspect, the glial progenitor medium with one or more stem cell differentiation modulators as described herein is exchanged daily for about 4 days. In an aspect, the medium with the one or more stem cell differentiation modulators as described herein is exchanged daily for the next three days prior to the initiation of the differentiation.

In an aspect, the differentiation of the undifferentiated stem cells with or without pretreatment can be initiated by enumerating the cells using a surrogate flask using collagenase IV and 0.05% Trypsin-EDTA in series to achieve a single cell suspension for quantification and harvesting the remaining undifferentiated stem cell cultures using collagenase IV and manual scraping. In an aspect, the undifferentiated stem cell cultures can be seeded into ultralow attachment (ULA) vessels to form embryoid bodies (EBs) at a density that ranges from about $1\times10^5$ cells/cm$^2$ to about $14\times10^5$ cells/cm$^2$, such as about $2\times10^5$ cells/cm$^2$ to about $13\times10^5$ cells/cm$^2$, such as about $3\times10^5$ cells/cm$^2$ to about $12\times10^5$ cells/cm$^2$, such as about $4\times10^5$ cells/cm$^2$ to about $11\times10^5$ cells/cm$^2$, such as about $5\times10^5$ cells/cm$^2$ to about $10\times10^5$ cells/cm$^2$, such as about $6\times10^5$ cells/cm$^2$ to about $9\times10^5$ cells/cm$^2$, such as about $7\times10^5$ cells/cm$^2$ to about $8\times10^5$ cells/cm$^2$. In one aspect, the undifferentiated stem cells are seeded at about $8\times10^5$ cells/cm$^2$.

In an aspect, on the following day of the differentiation, there can be a complete medium exchange using a 1:1 mixture of X-VIVO 10 and glial progenitor medium (GPM), which consists of DMEM/F12 (Gibco cat #10565-018), 2% B27 supplement (Gibco cat #17504-044), 0.04 μg tri-iodothyronin (Sigma cat #T5516-1MG) supplemented with 4 ng/ml hbFGF and 20 ng/mL EGF (Life Technologies cat #PHG0311). In an aspect, the GPM can be supplemented with hbFGF, EGF, and retinoic acid (RA). In an aspect, starting on the second day of the differentiation, the medium can be 100% GPM supplemented only with EGF and RA. In an aspect, this medium is replaced daily until Day 9. In an aspect, from Day 9 through Day 27, the GPM medium, supplemented with EGF, is exchanged about every other day. In an aspect, on Day 27 the EBs are plated onto coated vessels at a ratio of about 2 cm$^2$ for every 1 cm$^2$ of ULA seeded at the initiation of differentiation. In an aspect, a coated vessel may be coated with a Matrigel® matrix, recombinant Laminin, or Vitronectin. In an aspect, the culture medium used for the remainder of the entire differentiation is PM supplemented with 20 ng/mL EGF. In an aspect, from about Day 27 onward, the cell cultures receive a full medium replacement on alternating days. In an aspect, cells can be harvested on about Day 34 using Trypsin-EDTA or TrypLE Select supplemented with Benzonase and 0.01% Pluronic-F68, counted, and seeded onto Matrigel® matrix-coated vessels at about $5\times10^4$ viable cells/cm$^2$. In an aspect, the GPM medium is replaced on alternating days starting on about Day 34 until the final harvest, about 7 days later. In an aspect, OPCs are harvested on about Day 41 using 0.05% Trypsin-EDTA or TrypLE Select supplemented with Benzonase and 0.01% Pluronic-F68. In an aspect, the detached cells are pooled in a mixture of DMEM-F12 Medium and HypoThermosol FRS supplemented with Benzonase and 0.01% Pluronic-F68 prior to counting and reformulation in CryoStor 5 prior to cryopreservation.

OPC Compositions

As provided above, an aspect of the disclosure includes compositions comprising a plurality of oligodendrocyte progenitor cells (OPCs), as well as a method of making and using the same for improving one or more neurological functions in a subject in need of treatment. In certain aspects, the plurality of OPCs are the in vitro differentiated progeny of primate pluripotent stem (pPS) cells. In certain aspects, the plurality of OPCs are the in vitro differentiated progeny of human embryonic stem cells. In other aspects, the plurality of OPCs are the in vitro differentiated progeny of induced pluripotent stem (iPS) cells. In an aspect, a composition comprising a cell population that comprises a plurality of OPCs and low levels of undesirable cell types is provided.

In an aspect, a cell population can have a common genetic background. In an aspect, a cell population may be derived from one host. In an aspect, a cell population can be derived from a pluripotent stem cell line. In another aspect, a cell population can be derived from an embryonic stem cell line. In an aspect, a cell population can be derived from a hESC line. In an aspect, a hESC line can be an H1, H7, H9, H13, or H14 cell line. In another aspect, a cell population can be derived from an induced pluripotent stem cell (iPS) line. In an aspect, a cell population can be derived from a subject in need thereof (e.g., a cell population can be derived from a subject that is in need to treatment). In yet another aspect, a hESC line can be derived from parthenotes, which are embryos stimulated to produce hESCs without fertilization.

In an aspect, a cell population has not undergone cell enrichment. In an aspect, a cell population has not undergone a positive selection for OPCs. In an aspect, a positive selection for OPCs can be an antibody selection for Nestin, NG2, or PDGF-Rα, e.g., using flow cytometry or magnetic beads. In an aspect, a cell population may not have undergone a negative selection for an undesirable cell type. In an aspect, a negative selection for OPCs can be an antibody selection for EpCAM or CD49f, e.g., using flow cytometry or magnetic beads.

In an aspect, one or more characteristics of a cell population can be determined by quantifying various cell markers using flow cytometry, for example, to determine what percentage of the cell population is positive for a particular marker or set of markers. In an aspect, a cell population can comprise from about 30% to about 100% NG2 positive cells, such as at least about 35%, such as at least about 40%, such as at least about 45%, such as at least about 50%, such as at least about 55%, such as at least about 60%, such as at least about 65%, such as at least about 70%, such as at least about 75%, such as at least about 80%, such as at least about 85%, such as at least about 90%, such as at least about 95%, such as at least about 98%, such as at least about 99%, such as at least about 99.5%, such as at least about 99.8%, or such as at least about 99.9% NG2 positive cells. In another aspect, a cell population can comprise from about 30% to about 60% NG2 positive cells, such as about 30% to about 35%, such as about 35% to about 40%, such as about 40% to about 45%, such as about 45% to about 50%, such as about 35% to about 55%, such as about 40% to 50%, or such as about 43% to about 48% NG2 positive cells. In yet another aspect, a cell population can comprise from about 45% to about 75% NG2 positive cells, such as about 45% to about 50%, such as about 50% to about 55%, such as about 55% to about 60%, such as about 60% to about 65%, such as about 65% to about 70%, such as about 70% to about 75%, such as about 50% to about 70%, such as about 55% to about 65%, or such as about 58% to about 63% NG2 positive cells. In an aspect, a cell population can comprise from about 60% to about 90% NG2 positive cells, such as about 60% to about 65%, such as about 65% to about 70%, such as about 75% to about 80%, such as about 85% to about 90%, such as about 65% to about 85%, such as about 70% to about 80%, or such as about 73% to about 78% NG2 positive cells. In an aspect, a cell population can comprise from about 75% to about 100% NG2 positive cells, such as about 75% to about 80%, such as about 85% to about 90%, such as about 90% to about 95%, such as about 95% to about 100%, such as about 80% to about 95%, such as about 85% to about 90%, or such as about 73% to about 78% NG2 positive cells. In an aspect, a cell population can comprise at least about 30% NG2 positive cells. In another aspect, a cell population can comprise at least about 40% NG2 positive cells. In an aspect, a cell population can comprise at least about 50% NG2 positive cells.

In an aspect, a cell population can comprise from about 80% to about 100% Nestin positive cells, such as at least about 85%, such as at least about 90%, such as at least about 95%, such as about 99%, such as at least about 99.5%, such as at least about 99.8%, or such as at least about 99.9% Nestin positive cells. In another aspect, a cell population can comprise from about 80% to about 90% Nestin positive cells, such as about 80% to about 85%, or such as about 83% to about 88% Nestin positive cells. In yet another aspect, a cell population can comprise from about 90% to about 100% Nestin positive cells, such as about 90% to about 95%, such as about 95% to about 98%, such as about 98% to about 99%, such as about 99% to about 99.5%, such as about 99.5% to about 99.8%, such as about 99.8% to about 99.9%, such as about 99.9% to about 100%, such as about 90% to about 99.9%, such as about 95% to about 99.8%, or such as about 98% to about 99.5% Nestin positive cells. In an aspect, a cell population can comprise at least about 99% Nestin positive cells.

In an aspect, a cell population can comprise from about 80% to about 100% PDGF-Rα positive cells, such as at least about 85%, such as at least about 90%, such as at least about 95%, such as about 99%, such as about 99.5%, such as about 99.9%, or such as at least about 100% PDGF-Rα positive cells. In another aspect, a cell population can comprise from about 80% to about 90% PDGF-Rα positive cells, such as about 80% to about 85%, such as about 85% to about 90%, or such as about 83% to about 88% PDGF-Rα positive cells. In yet another aspect, a cell population can comprise from about 90% to 100% PDGF-Rα positive cells, such as about 90% to about 95%, such as about 95% to about 98%, such as about 98% to about 99%, such as about 99% to about 99.5%, such as about 99.5% to about 99.8%, such as about 99.8% to about 99.9%, such as about 99.9% to about 100%, such as about 90% to about 99.9%, such as about 95% to about 99.8%, or such as about 98% to about 99.5% PDGF-Rα positive cells. In an aspect, a cell population can comprise at least about 80% PDGF-Rα positive cells.

In an aspect, a cell population can comprise about 50% NG2 positive cells and about 81% PDGF-Rα positive cells. In another aspect, a cell population can comprise about 50% NG2 positive cells, about 81% PDGF-Rα positive cells, and about 99% Nestin positive cells.

In an aspect, at least about 90% of a cell population can express at least one of the markers selected from the group consisting of Nestin, PDGF-Rα, Nkx 2.2, Olig1, and IGF2. In another aspect, at least about 90% of a cell population can express at least two of the markers selected from the group consisting of Nestin, PDGF-Rα, Nkx 2.2, Olig1, and IGF2. In yet another aspect, at least about 90% of a cell population can express at least three of the markers selected from the group consisting of Nestin, PDGF-Rα, Nkx 2.2, Olig1, and IGF2. In another aspect, at least about 90% of a cell population can express at least four of the markers selected from the group consisting of Nestin, PDGF-Rα, Nkx 2.2, Olig1, and IGF2. In an aspect, at least about 90% of a cell population can express all of Nestin, PDGF-Rα, Nkx 2.2, Olig1, and IGF2. In an aspect, about 90% to about 100% of a cell population can express at least one of the markers selected from the group consisting of Nestin, PDGF-Rα, Nkx 2.2, Olig1, and IGF2. In an aspect, about 95% to about 100%, such as about 98% to about 100%, such as about 99% to about 100%, such as about 99.5% to about 100%, such as about 99.8% to about 100%, or such as about 99.9% to about 100% of a cell population can express at least one of the markers selected from the group consisting of Nestin, PDGF-Rα, Nkx 2.2, Olig1, and IGF2.

In an aspect, a cell population can be capable of producing one or more biological signaling factors. In an aspect, a cell population can be capable of producing one or more angiogenic signaling factors. In an aspect, an angiogenic signaling factor can be thrombospondin-1, serpine1, or serpine2. In an aspect, a cell population can be capable of producing one or more neurotrophic signaling factors. In an aspect, a neurotropic signaling factor can be NGF, Netrin 4, Tenascin C, Thrombospondin 1, Thrombospondin 3, SLIT1 or SLIT3. In an aspect, the neurotropic signaling factor can be detected by ELISA. In an aspect, a biological signaling factor can be Glial-Derived Nexin 1, Lumican, TIMP2, IGF2, MMP15, or VEGF. In an aspect, a biological signaling factor can be Decorin. In an aspect, a biological signaling factor can be Midkine.

In an aspect, a biological signaling factor can be secreted by a composition comprising a population of cells comprising OPCs at a concentration of more than about 50 pg/ml, such as more than about 100 pg/ml, such as more than about 200 pg/ml, such as more than about 300 pg/ml, such as more than about 400 pg/ml, such as more than about 500 pg/ml, such as more than about 1,000 pg/ml, such as more than about 2,000 pg/ml, such as more than about 3,000 pg/ml, such as more than about 4,000 pg/ml, such as more than about 5,000 pg/ml, such as more than about 6,000 pg/ml, or such as more than about 7,000 pg/ml. In an aspect, a biological signaling factor can be secreted by a composition comprising a population of cells comprising OPCs at a concentration ranging from about 50 pg/ml to about 100,000 pg/ml, such as about 100 pg/ml, such as about 150 pg/ml, such as about 200 pg/ml, such as about 250 pg/ml, such as about 300 pg/ml, such as about 350 pg/ml, such as about 400 pg/ml, such as about 450 pg/ml, such as about 500 pg/ml, such as about 550 pg/ml, such as about 600 pg/ml, such as about 650 pg/ml, such as about 700 pg/ml, such as about 750 pg/ml, such as about 800 pg/ml, such as about 850 pg/ml, such as about 900 pg/ml, such as about 1,000 pg/ml, such as about 1,500 pg/ml, such as about 2,000 pg/ml, such as about 2,500 pg/ml, such as about 3,000 pg/ml, such as about 3,500 pg/ml, such as about 4,000 pg/ml, such as about 4,500 pg/ml, such as about 5,000 pg/ml, such as about 5,500 pg/ml, such as about 6,000 pg/ml, such as about 6,500 pg/ml, such as about 7,000 pg/ml, such as about 7,500 pg/ml, such as about 8,000 pg/ml, such as about 8,500 pg/ml, such as about 9,000 pg/ml, such as about 10,000 pg/ml, such as about 15,000 pg/ml, such as about 20,000 pg/ml, such as about 25,000 pg/ml, such as about 30,000 pg/ml, such as about 35,000 pg/ml, such as about 40,000 pg/ml, such as about 45,000 pg/ml, such as about 50,000 pg/ml, such as about 55,000 pg/ml, such as about 60,000 pg/ml, such as about 65,000 pg/ml, such as about 70,000 pg/ml, such as about 75,000 pg/ml, such as about 80,000 pg/ml, such as about 85,000 pg/ml, such as about 90,000 pg/ml, such as about 95,000 pg/ml. In an aspect, a biological signaling factor can be secreted by a composition comprising a population of cells comprising OPCs at a concentration ranging from about 50 pg/ml to about 1,000 pg/ml, such as about 50 pg/ml to about 100 pg/ml, such as about 100 pg/ml to about 200 pg/ml, such as about 200 pg/ml to about 300 pg/ml, such as about 300 pg/ml to about 400 pg/ml, such as about 400 pg/ml to about 500 pg/ml, such as about 500 pg/ml to about 600 pg/ml, such as about 600 pg/ml to about 700 pg/ml, such as about 700 pg/ml to about 800 pg/ml, such as about 800 pg/ml to about 900 pg/ml, or such as about 900 pg/ml to about 1,000 pg/ml. In an aspect, a biological signaling factor can be secreted by a composition comprising a population of cells comprising OPCs at a concentration ranging from about 1,000 pg/ml to about 10,000 pg/ml, such as about 1,000 pg/ml to about 2,000 pg/ml, such as about 2,000 pg/ml to about 3,000 pg/ml, such as about 3,000 pg/ml to about 4,000 pg/ml, such as about 4,000 pg/ml to about 5,000 pg/ml, such as about 5,000 pg/ml to about 6,000 pg/ml, such as about 6,000 pg/ml to about 7,000 pg/ml, such as about 7,000 pg/ml to about 8,000 pg/ml, such as about 8,000 pg/ml to about 9,000 pg/ml, or such as about 9,000 pg/ml to about 10,000 pg/ml. In an aspect, a biological signaling factor can be secreted by a composition comprising a population of cells comprising OPCs at a concentration ranging from about 10,000 pg/ml to about 100,000 pg/ml, such as about 10,000 pg/ml to about 20,000 pg/ml, such as about 20,000 pg/ml to about 30,000 pg/ml, such as about 30,000 pg/ml to about 40,000 pg/ml, such as about 40,000 pg/ml to about 50,000 pg/ml, such as about 50,000 pg/ml to about 60,000 pg/ml, such as about 60,000 pg/ml to about 70,000 pg/ml, such as about 70,000 pg/ml to about 80,000 pg/ml, such as about 80,000 pg/ml to about 90,000 pg/ml, or such as about 90,000 pg/ml to about 100,000 pg/ml.

In an aspect, Midkine can be secreted by a composition comprising a population of cells comprising OPCs at a concentration ranging from about 100 pg/ml to about 10,000 pg/ml. In another aspect, Decorin can be secreted by a composition comprising a population of cells comprising OPCs at a concentration ranging from about 500 pg/ml to about 50,000 pg/ml. In yet another aspect, Netrin 4 can be secreted by a composition comprising a population of cells comprising OPCs at a concentration ranging from about 500 pg/ml to about 50,000 pg/ml. In an aspect, Glial-Derived Nexin 1 can be secreted by a composition comprising a population of cells comprising OPCs at a concentration ranging from about 500 pg/ml to about 50,000 pg/ml. In an aspect, Lumican can be secreted by a composition comprising a population of cells comprising OPCs at a concentration ranging from about 500 pg/ml to about 50,000 pg/ml. In an aspect, TIMP2 can be secreted by a composition comprising a population of cells comprising OPCs at a concentration ranging from about 500 pg/ml to about 50,000 pg/ml. In an aspect, IGF2 can be secreted by a composition comprising a population of cells comprising OPCs at a concentration ranging from about 100 pg/ml to about 10,000 pg/ml. In an aspect, MMP15 can be secreted by a composition comprising a population of cells comprising OPCs at a concentration ranging from about 50 pg/ml to about 5000 pg/ml. In an aspect, VEGF can be secreted by a composition comprising a population of cells comprising OPCs at a concentration ranging from about 50 pg/ml to about 5000 pg/ml. In an aspect, NGF can be secreted by a composition comprising a population of cells comprising OPCs at a concentration ranging from about 50 pg/ml to about 5000 pg/ml.

In an aspect, a cell population can be capable of forming less than or equal to one epithelial cyst per 100,000 cells in a cyst assay as described in Example 5 of the present disclosure. In an aspect, the cell population can be capable of forming less than or equal to one epithelial cyst per about 200,000 cells, per about 300,000 cells, per about 400,000, or per about 500,000 cells in a cyst assay as described in Example 5 of the present disclosure.

Undesirable Cell Types

In an aspect, a cell population can comprise less than about 20% undesirable cell types, such as less than about 19%, such as less than about 18%, such as less than about 17%, such as less than about 16%, such as less than about 15%, such as less than about 14%, such as less than about 13%, such as less than about 12%, such as less than about 11%, such as less than about 10%, such as less than about 9%, such as less than about 8%, such as less than about 7%, such as less than about 6%, such as less than about 5%, such as less than about 4%, such as less than about 3%, such as less than about 2%, such as less than about 1%, such as less than about 0.5%, such as less than about 0.1%, such as less than about 0.05%, or such as less than about 0.01% undesirable cell types. In another aspect, a cell population can comprise from about 15% to about 20% undesirable cell types, such as about 19% to about 20%, such as about 18% to about 20%, such as about 17% to about 20%, such as about 16% to about 20%, such as about 15% to about 19%, or such as about 16% to about 18% undesirable cell types. In yet another aspect, a cell population can comprise from about 10% to about 15% undesirable cell types, such as about 14% to about 15%, such as about 13% to about 15%, such as about 12% to about 15%, such as about 11% to about 15%, or such as about 12% to about 14% undesirable cell types. In an aspect, a cell population can comprise from about 1% to about 10% undesirable cell types, such as about 2% to about 10%, such as about 1% to about 9%, such as about 2% to about 8%, such as about 3% to about 7%, or such as about 4% to about 6% undesirable cell types. In an aspect, a cell population can comprise from about 0.1% to about 1% undesirable cell types, such as about 0.2% to about 1%, such as about 0.1% to about 0.9%, such as about 0.2% to about 0.8%, such as about 0.3% to about 0.7%, or such as about 0.4% to about 0.6% undesirable cell types. In an aspect, a cell population can comprise from about 0.01% to about 0.1% undesirable cell types, such as about 0.02% to about 0.1%, such as about 0.01% to about 0.09%, such as about 0.02% to about 0.08%, such as about 0.03% to about 0.07%, or such as about 0.04% to about 0.06% undesirable cell types. In an aspect, low levels of undesirable cell types can denote the presence of less than about 15% undesirable cell types.

In an aspect, an undesirable cell type can comprise epithelial lineage cells. In an aspect, epithelial lineage cells can be characterized by the presence of one of K7 or PCK. In an aspect, epithelial lineage cells can be characterized by the presence of both K7 and PCK.

In an aspect, an undesirable cell type can comprise K7 positive cells. In an aspect, a cell population can comprise less than about 5% K7 positive cells, such as less than about 4%, such as less than about 3%, such as less than about 2%, such as less than about 1.5%, such as less than about 1%, such as less than about 0.9%, such as less than about 0.8%, such as less than about 0.7%, such as less than about 0.6%, such as less than about 0.5%, such as less than about 0.4%, such as less than about 0.3%, such as less than about 0.2%, such as less than about 0.1%, such as less than about 0.09%, such as less than about 0.08%, such as less than about 0.07%, such as less than about 0.06%, such as less than about 0.05%, or such as less than about 0.01% K7 positive cells. In an aspect, a cell population can comprise from about 0.01% to about 5% K7 positive cells, such as about 0.05%, such as about 0.1%, such as about 0.2%, such as about 0.3%, such as about 0.4%, such as about 0.5%, such as about 0.6%, such as about 0.7%, such as about 0.8%, such as about 0.9%, such as about 1%, such as about 1.5%, such as about 2%, such as about 2.5%, such as about 3%, such as about 3.5%, such as about 4%, or such as about 4.5% K7 positive cells. In an aspect, a cell population can comprise from about 1% to about 5% K7 positive cells, such as about 2% to about 4%, such as about 1% to about 3%, or such as about 3% to about 5% K7 positive cells. In an aspect, a cell population can comprise from about 0.1% to about 1%, such as about 0.2% to about 0.9%, such as about 0.3% to about 0.8%, such as about 0.4% to about 0.7%, or such as about 0.5% to about 0.6% K7 positive cells. In an aspect, a cell population can comprise from about 0.01% to about 0.1% K7 positive cells, such as about 0.02% to about 0.09%, such as about 0.03% to about 0.08%, such as about 0.04% to about 0.07%, or such as about 0.05% to about 0.06% K7 positive cells. In an aspect, a cell population can comprise less than about 2% K7 positive cells. In another aspect, a cell population can comprise less than about 0.2% K7 positive cells.

In an aspect, an undesirable cell type can comprise PCK positive cells. In an aspect, a cell population can comprise less than about 10% PCK positive cells, such as less than about 9%, such as less than about 8%, such as less than about 7%, such as less than about 6%, such as less than about 5%, such as less than about 4.5%, such as less than about 4%, such as less than about 3.5%, such as less than about 3%, such as less than about 2.5%, such as less than about 2%, such as less than about 1.5%, such as less than about 1%, such as less than about 0.5%, such as less than about 0.1%, such as less than about 0.05%, or such as less than about 0.01% PCK positive cells. In an aspect, a cell population can comprise from about 0.01% to about 10% PCK positive cells, such as about 0.05%, such as about 0.1%, such as about 0.2%, such as about 0.3%, such as about 0.4%, such as about 0.5%, such as about 0.6%, such as about 0.7%, such as about 0.8%, such as about 0.9%, such as about 1%, such as about 2%, such as about 3%, such as about 4%, such as about 5%, such as about 6%, such as about 7%, such as about 8%, or such as about 9% PCK positive cells. In an aspect, a cell population can comprise from about 1% to about 10% PCK positive cells, such as about 2% to about 9%, such as about 3% to about 8%, such as about 4% to about 7%, or such as about 5% to about 6% PCK positive cells. In an aspect, a cell population can comprise from about 0.1% to about 1% PCK positive cells, such as about 0.2% to about 0.9%, such as about 0.3% to about 0.8%, such as about 0.4% to about 0.7%, or such as about 0.5% to about 0.6% PCK positive cells. In an aspect, a cell population can comprise from about 0.01% to about 0.1% PCK positive cells, such as about 0.02% to about 0.09%, such as about 0.03% to about 0.08%, such as about 0.04% to about 0.07%, or such as about 0.05% to about 0.06% PCK positive cells. In an aspect, the cell population can comprise less than about 5% PCK positive cells.

In an aspect, a population of OPCs can comprise about 2% K7 positive cells and about 4% PCK positive cells.

Formulation

In an aspect, a composition in accordance with the present disclosure can further comprise a pharmaceutically-acceptable carrier. In an aspect, a pharmaceutically-acceptable carrier can comprise dimethyl sulfoxide (DMSO). In an aspect, a pharmaceutically-acceptable carrier does not comprise dimethyl sulfoxide. In an aspect, a composition can be adapted for cryopreservation.

In an aspect, a composition in accordance with the present disclosure can be formulated for administration via a direct injection to the spinal cord of a subject. In an aspect, a composition in accordance with the present disclosure can be formulated for intracerebral, intraventricular, intrathecal, intranasal, or intracisternal administration to a subject. In an aspect, a composition in accordance with the present disclosure can be formulated for administration via an injection directly into or immediately adjacent to an infarct cavity in the brain of a subject. In an aspect, a composition in accordance with the present disclosure can be formulated for administration through implantation. In an aspect, a composition in accordance with the present disclosure can be formulated as a solution.

In an aspect, a composition in accordance with the present disclosure can comprise from about $1\times10^6$ to about $5\times10^8$ cells per milliliter, such as about $1\times10^6$ cells per milliliter, such as about $2\times10^6$ cells per milliliter, such as about $3\times10^6$ cells per milliliter, such as about $4\times10^6$ cells per milliliter, such as about $5\times10^6$ cells per milliliter, such as about $6\times10^6$ cells per milliliter, such as about $7\times10^6$ cells per milliliter, such as about $8\times10^6$ cells per milliliter, such as about $9\times10^6$ cells per milliliter, such as about $1\times10^7$ cells per milliliter, such as about $2\times10^7$ cells per milliliter, such as about $3\times10^7$ cells per milliliter, such as about $4\times10^7$ cells per milliliter, such as about $5\times10^7$ cells per milliliter, such as about $6\times10^7$ cells per milliliter, such as about $7\times10^7$ cells per milliliter, such as about $8\times10^7$ cells per milliliter, such as about $9\times10^7$ cells per milliliter, such as about $1\times10^8$ cells per milliliter, such as about $2\times10^8$ cells per milliliter, such as about $3\times10^8$ cells per milliliter, such as about $4\times10^8$ cells per milliliter, or such as about $5\times10^8$ cells per milliliter. In another aspect, a composition in accordance with the present disclosure can comprise from about $1\times10^8$ to about $5\times10^8$ cells per milliliter, such as about $1\times10^8$ to about $4\times10^8$ cells per milliliter, such as about $2\times10^8$ to about $5\times10^8$ cells per milliliter, such as about $1\times10^8$ to about $3\times10^8$ cells per milliliter, such as about $2\times10^8$ to about $4\times10^8$ cells per milliliter, or such as about $3\times10^8$ to about $5\times10^8$ cells per milliliter. In yet another aspect, a composition in accordance with the present disclosure can comprise from about $1\times10^7$ to about $1\times10^8$ cells per milliliter, such as about $2\times10^7$ to about $9\times10^7$ cells per milliliter, such as about $3\times10^7$ to about $8\times10^7$ cells per milliliter, such as about $4\times10^7$ to about $7\times10^7$ cells per milliliter, or such as about $5\times10^7$ to about $6\times10^7$ cells per milliliter. In an aspect, a composition in accordance with the present disclosure can comprise from about $1\times10^6$ to about $1\times10^7$ cells per milliliter, such as about $2\times10^6$ to about $9\times10^6$ cells per milliliter, such as about $3\times10^6$ to about $8\times10^6$ cells per milliliter, such as about $4\times10^6$ to about $7\times10^6$ cells per milliliter, or such as about $5\times10^6$ to about $6\times10^6$ cells per milliliter. In yet another aspect, a composition in accordance with the present disclosure can comprise at least about $1\times10^6$ cells per milliliter, such as at least about $2\times10^6$ cells per milliliter, such as at least about $3\times10^6$ cells per milliliter, such as at least about $4\times10^6$ cells per milliliter, such as at least about $5\times10^6$ cells per milliliter, such as at least about $6\times10^6$ cells per milliliter, such as at least about $7\times10^6$ cells per milliliter, such as at least about $8\times10^6$ cells per milliliter, such as at least about $9\times10^6$ cells per milliliter, such as at least about $1\times10^7$ cells per milliliter, such as at least about $2\times10^7$ cells per milliliter, such as at least about $3\times10^7$ cells per milliliter, such as at least about $4\times10^7$ cells per milliliter, or such as at least about $5\times10^7$ cells per milliliter. In an aspect, a composition in accordance with the present disclosure can comprise up to about $1\times10^8$ cells or more, such as up to about $2\times10^8$ cells per milliliter or more, such as up to about $3\times10^8$ cells per milliliter or more, such as up to about $4\times10^8$ cells per milliliter or more, such as up to about $5\times10^8$ cells per milliliter or more, or such as up to about $6\times10^8$ cells per milliliter.

In an aspect, a composition in accordance with the present disclosure can comprise from about $4\times10^7$ to about $2\times10^8$ cells per milliliter.

In yet another aspect, a composition in accordance with the present disclosure can have a volume ranging from about 10 microliters to about 5 milliliters, such as about 20 microliters, such as about 30 microliters, such as about 40 microliters, such as about 50 microliters, such as about 60 microliters, such as about 70 microliters, such as about 80 microliters, such as about 90 microliters, such as about 100 microliters, such as about 200 microliters, such as about 300 microliters, such as about 400 microliters, such as about 500 microliters, such as about 600 microliters, such as about 700 microliters, such as about 800 microliters, such as about 900 microliters, such as about 1 milliliter, such as about 1.5 milliliters, such as about 2 milliliters, such as about 2.5 milliliters, such as about 3 milliliters, such as about 3.5 milliliters, such as about 4 milliliters, or such as about 4.5 milliliters. In an aspect, a composition in accordance with the present disclosure can have a volume ranging from about 10 microliters to about 100 microliters, such as about 20 microliters to about 90 microliters, such as about 30 microliters to about 80 microliters, such as about 40 microliters to about 70 microliters, or such as about 50 microliters to about 60 microliters. In another aspect, a composition in accordance with the present disclosure can have a volume ranging from about 100 microliters to about 1 milliliter, such as about 200 microliters to about 900 microliters, such as about 300 microliters to about 800 microliters, such as about 400 microliters to about 700 microliters, or such as about 500 microliters to about 600 microliters. In yet another aspect, a composition in accordance with the present disclosure can have a volume ranging from about 1 milliliter to about 5 milliliters, such as about 2 milliliter to about 5 milliliters, such as about 1 milliliter to about 4 milliliters, such as about 1 milliliter to about 3 milliliters, such as about 2 milliliter to about 4 milliliters, or such as about 3 milliliter to about 5 milliliters. In an aspect, a composition in accordance with the present disclosure can have a volume of about 20 microliters to about 500 microliters. In another aspect, a composition in accordance with the present disclosure can have a volume of about 50 microliters to about 100 microliters. In yet another aspect, a composition in accordance with the present disclosure can have a volume of about 50 microliters to about 200 microliters. In another aspect, a composition in accordance with the present disclosure can have a volume of about 20 microliters to about 400 microliters.

Container

In an aspect, a container can comprise a composition comprising a cell population in accordance with the present disclosure. In an aspect, a container can be configured for cryopreservation. In an aspect, a container can be configured for administration to a subject in need thereof. In an aspect, a container can be a prefilled syringe.

Methods of Use

An aspect of the disclosure includes a method of using a cell population that comprises a plurality of OPCs, as described herein, for improving one or more neurological functions in a subject in need of treatment. In an aspect, a cell population in accordance with the present disclosure can be injected or implanted into a subject in need thereof. In an aspect, a subject may be in need of functional improvement of the central nervous system. In an aspect, a cell population in accordance with the present disclosure can be implanted into a subject in need thereof for treating spinal cord injury, stroke, or multiple sclerosis.

In an aspect, a cell population in accordance with the present disclosure can be capable of producing an ectopic tissue in less than about 2% of subjects upon implantation of up to about $1\times10^9$ cells into a central nervous system injury site, such as up to about $1\times10^6$ cells, such as up to about $25\times10^6$ cells, such as up to about $50\times10^6$ cells, such as up to about $75\times10^6$ cells, such as up to about $100\times10^6$ cells, such as up to about $200\times10^6$ cells, such as up to about $300\times10^6$ cells, such as up to about $400\times10^6$ cells, such as up to about $500\times10^6$ cells, such as up to about $600\times10^6$ cells, such as up to about $700\times10^6$ cells, such as up to about $800\times10^6$ cells, or such as up to about $900\times10^6$ cells. In an aspect, a cell population in accordance with the present disclosure can be capable of producing an ectopic tissue in less than about 2% of subjects upon implantation of from about $1\times10^6$ cells to about $1\times10^9$ cells into a central nervous system injury site, such as about $50\times10^6$ cells to about $900\times10^6$ cells, such as about $100\times10^6$ cells to about $800\times10^6$ cells, such as about $200\times10^6$ cells to about $700\times10^6$ cells, such as about $300\times10^6$ cells to about $600\times10^6$ cells, or such as about $400\times10^6$ cells to about $500\times10^6$ cells. In an aspect, a cell population in accordance with the present disclosure can be capable of producing an ectopic tissue in less than about 2% of subjects upon implantation of up to about $1\times10^9$ of the cells into a central nervous system injury site. In one aspect, a cell population in accordance with the present disclosure can be capable of producing an ectopic tissue in less than about 1% of subjects upon implantation of up to about $1\times10^9$ of the cells into a central nervous system injury site.

In an aspect, a cell population in accordance with the present disclosure can be capable of inducing myelination of denuded axons at an implantation site in a subject. In an aspect, a cell population generated with pretreatment in accordance with a method of the present disclosure can exhibit improved capacity for engraftment and migration compared to a cell population produced without pretreatment. In an aspect, a cell population generated with pretreatment in accordance with a method of the present disclosure can exhibit improved post-injury repair or regeneration of neural tissue compared to a cell population produced without pretreatment.

In an aspect, a cell population in accordance with the present disclosure can be capable of improving a sensory function in a subject in need of therapy following implantation of the population into the subject. In an aspect, improvements in a sensory function can be evaluated using the International Standards for Neurological Classification of Spinal Cord Injury (ISNCSCI) Exam, such as determining sensory levels for right and left sides for pin prick and light touch sensations. In an aspect, a cell population in accordance with the present disclosure can be capable of improving a motor function in a subject in need of therapy following implantation of the population into the subject. In an aspect, a cell population can be capable of sustainably improving the subject's motor function for at least two months. In an aspect, a cell population can be capable of sustainably improving the subject's motor function for at least six months, at least one year, at least two years, or at least three years. In an aspect, an improved motor function can be increased standing ability or weight support, increased limb function or limb strength, increased walking distance, increased walking speed, increased bowel or bladder function, increased arm or hand movement, or increasing gripping, grasping, or prehension. In an aspect, an improved motor function can be evaluated using the ISNCSCI Exam, such as determining motor levels for right and left sides for total paralysis, palpable or visible contraction, active movement, full range of motion against gravity, and sufficient resistance.

In an aspect, a cell population in accordance with the present disclosure can be capable of reducing a volume of an injury-induced central nervous system parenchymal cavitation in 12 months or less. In an aspect, a cell population in accordance with the present disclosure can be capable of reducing a volume of an injury-induced central nervous system parenchymal cavitation in 6 months or less, 5 months or less, 4 months or less, 3 months or less, 2 months or less, or less than 1 month.

In an aspect, one or more cells from a cell population in accordance with the present disclosure can be capable of migrating from a first location to one or more second locations within the central nervous system of a subject in need thereof. In an aspect, one or more cells from a cell population in accordance with the present disclosure can be capable of migrating from the spinal cord of a subject to an affected tissue within the brain of the subject. In one aspect, one or more cells from a cell population in accordance with the present disclosure can be capable of migrating from a first location within the spinal cord of a subject to a second location at an affected tissue within the spinal cord of the subject. In one aspect, one or more cells from a cell population in accordance with the present disclosure can be capable of migrating from a first location within the brain of a subject to a second location at an affected tissue within the brain of the subject. In one aspect, one or more cells from a cell population in accordance with the present disclosure can be capable of migrating from a first location within the brain of a subject to an affected tissue within the spinal cord of the subject. In one aspect, one or more cells from a cell population in accordance with the present disclosure can be capable of migrating from a first location within the spinal cord of a subject to a second location at an affected tissue within the spinal cord of the subject, as well as to one or more locations at one or more affected tissues within the brain of the subject. In one aspect, one or more cells from a cell population in accordance with the present disclosure can be capable of migrating from a first location within the brain of a subject to a second location at an affected tissue within the brain of the subject, as well as to one or more locations at one or more affected tissues within the spinal cord of the subject.

In an aspect, one or more cells from a cell population in accordance with the present disclosure can be capable of migrating from a first location to one or more second locations at one or more affected tissues within the central nervous system of a subject in less than about 150 days, such as less than about 100 days, such as less than about 50 days, or such as less than about 10 days. In an aspect, one or more cells from a cell population in accordance with the present disclosure can be capable of migrating from a first location to one or more second locations at one or more affected tissues within the central nervous system of a subject in about 180 days or less.

Additional Embodiments

An aspect of the present disclosure includes a container comprising a composition, wherein the composition comprises a population of cells comprising a plurality of oligodendrocyte progenitor cells (OPCs), and wherein the population of cells comprises less than 15% undesirable cell types. In an aspect, the undesirable cell types comprise epithelial lineage cells. In an aspect, the epithelial lineage cells are characterized by the presence of one or more markers selected from the group consisting of: K7 and PCK. In an aspect, the population of cells comprises less than 2% K7 positive cells. In an aspect, the population of cells comprises less than 0.2% K7 positive cells. In an aspect, the population of cells comprises less than 5% PCK positive cells. In an aspect, the population of cells has a common genetic background. In an aspect, the population of cells has not undergone cell enrichment. In an aspect, the container is configured for cryopreservation.

An aspect of the present disclosure also includes a container comprising a composition, wherein the composition comprises a population of cells comprising a plurality of oligodendrocyte progenitor cells (OPCs), and wherein the population of cells is capable of forming less than or equal to one epithelial cyst per 100,000 cells in a cyst assay. In an aspect, the population of cells is capable of reducing a volume of an injury-induced central nervous system parenchymal cavitation in 12 months or less. In an aspect, the population of cells is capable of migrating from a first location to one or more second locations at one or more affected tissues within a central nervous system tissue of a subject in 180 days or less. In an aspect, the central nervous system tissue is a spinal cord tissue. In an aspect, the central nervous system tissue is a brain tissue. In an aspect, the population of cells is capable of improving a motor function in a subject in need of therapy following implantation of the population into the subject. In an aspect, the population of cells is capable of sustainably improving the motor function for at least two months. In an aspect, the motor function is increased standing ability or weight support. In an aspect, the motor function is increased limb function or limb strength. In an aspect, the motor function is increased walking distance. In an aspect, the motor function is increased walking speed. In an aspect, the motor function is increased bowel or bladder function. In an aspect, the motor function is increased arm or hand movement. In an aspect, the motor function is increased gripping, grasping, or prehension.

An aspect of the present disclosure also includes a container comprising a composition, wherein the composition comprises a population of cells comprising a plurality of oligodendrocyte progenitor cells (OPCs), and wherein the population of cells is capable of forming less than or equal to one epithelial cyst per 100,000 cells in a cyst assay. In an aspect, the population of cells is capable of producing one or more biological signaling factors. In an aspect, the population of cells is capable of producing an angiogenic signaling factor. In an aspect, the angiogenic signaling factor is selected from the group consisting of Thrombospondin-1, Serpine1, Serpine2, and a combination thereof. In an aspect, the population of cells is capable of producing a neurotrophic signaling factor. In an aspect, the neurotrophic factors are selected from the group consisting of NGF, Netrin 4, Tenascin C, Thrombospondin 1, Thrombospondin 3, SLIT1, SLIT3, and a combination thereof. In an aspect, the one or more biological signaling factors comprises Decorin. In an aspect, the one or more biological signaling factors comprises Midkine. In an aspect, the population of cells is capable of inducing myelination of denuded axons at an implantation site in a subject.

An aspect of the present disclosure also includes a container comprising a composition, wherein the composition comprises a population of cells comprising a plurality of oligodendrocyte progenitor cells (OPCs), and wherein the population of cells is capable of producing an ectopic tissue in less than 2% of subjects upon implantation of up to $1\times10^9$ of the cells into a central nervous system injury site. In an aspect, the population of cells is capable of producing an ectopic tissue in less than 1% of subjects upon implantation of up to $1\times10^9$ of the cells into a central nervous system injury site.

The aforementioned aspects of the present disclosure can further include a composition comprising a population of cells, wherein at least 30% of the population of cells are NG2 positive cells. In an aspect, at least 40% of the population of cells are NG2 positive cells. In an aspect, at least 50% of the population of cells are NG2 positive cells.

An aspect of the present disclosure also includes a container comprising a composition, wherein the composition comprises a population of oligodendrocyte progenitor cells (OPCs), and wherein at least 95% of the OPCs express a marker selected from the group consisting of PDGF-Rα, IGF2, Nkx2.2, Olig1, and Nestin. In an aspect, at least 98% of the OPCs express a marker selected from the group consisting of PDGF-Rα, IGF2, Nkx2.2, Olig1, and Nestin. In an aspect, at least 99% of the OPCs express a marker selected from the group consisting of PDGF-Rα, IGF2, Nkx2.2, Olig1, and Nestin. In an aspect, at least 99.5% of the OPCs express a marker selected from the group consisting of PDGF-Rα, IGF2, Nkx2.2, Olig1, and Nestin. In an aspect, 100% of the OPCs express a marker selected from the group consisting of PDGF-Rα, IGF2, Nkx2.2, Olig1, and Nestin. In an aspect, at least 95% of the OPCs express a second marker selected from the group consisting of PDGF-Rα, IGF2, Nkx2.2, Olig1, and Nestin. In an aspect, at least 98% of the OPCs express a second marker selected from the group consisting of PDGF-Rα, IGF2, Nkx2.2, Olig1, and Nestin. In an aspect, at least 99% of the OPCs express a second marker selected from the group consisting of PDGF-Rα, IGF2, Nkx2.2, Olig1, and Nestin. In an aspect, at least 99.5% of the OPCs express a second marker selected from the group consisting of PDGF-Rα, IGF2, Nkx2.2, Olig1, and Nestin. In an aspect, 100% of the OPCs express a second marker selected from the group consisting of PDGF-Rα, IGF2, Nkx2.2, Olig1, and Nestin.

The aforementioned aspects of the present disclosure can further comprise a pharmaceutically-acceptable carrier. In an aspect, the pharmaceutically-acceptable carrier comprises dimethyl sulfoxide. In an aspect, the pharmaceutically-acceptable carrier does not comprise dimethyl sulfoxide.

The aforementioned aspects of the present disclosure can further include a composition comprising a population of cells, whereinthe composition comprises at least $1\times10^6$ cells per milliliter. In an aspect, the composition comprises $1\times10^6$ to $5\times10^8$ cells per milliliter. In an aspect, the composition comprises $4\times10^7$ to $2\times10^8$ cells per milliliter. In an aspect, the composition has a volume of 20 to 500 microliters. In an aspect, the composition has a volume of 50 to 200 microliters. In an aspect, the composition has a volume of about 100 microliters. In an aspect, the composition is an injectable solution. In an aspect, the composition is adapted for cryopreservation.

Furthermore, aspects of the present disclosure include a method of differentiating pluripotent stem cells, the method comprising one or more steps directed to pretreating a plurality of undifferentiated stem cells. In an aspect, the one or more steps directed to pretreating comprises incubating expanded but undifferentiated stem cells for a period of time, during which the undifferentiated stem cells are contacted with one or more stem cell differentiation modulating molecules. In an aspect, the one or more stem cell differentiation modulating molecules is selected from the group consisting of: (1) an inhibitor of ALK5, which is a part of the SMAD/TGFβ-RII signaling pathway; (2) an inhibitor of ALK2, which is a part of the BMPRI signaling pathway; (3) a GSK3 inhibitor for activating the WNT signaling pathway; and (4) a Smoothened agonist for activating the SHH pathway. In an aspect, a method comprises incubating expanded but undifferentiated stem cells for a period of time with four small molecules: SB431542, Dorsomorphin, CHIR99021, and Purmorphamine. In an aspect, a method comprises incubating a population of expanded but undifferentiated stem cells for a first period of time, during which the undifferentiated stem cells are contacted with two or more first stem cell differentiation modulators, and incubating the population for a second period of time, during which the cells are contacted with two or more second stem cell differentiation modulators. In an aspect, the two or more first stem cell differentiation modulators are different from the two or more second stem cell differentiation modulators. In an aspect, the two or more first stem cell modulators are the same as the two or more second stem cell modulators. In an aspect, the first and second stem cell modulators share at least one common modulator. In an aspect, the first and second stem cell modulators share two or more common modulators, such as three or more common modulators, such as four or more common modulators.

Having now generally described the invention, the same will be more readily understood through reference to the following examples that are provided by way of illustration, and are not intended to be limiting of the present disclosure, unless specified.

EXAMPLES

Example 1—Method of Producing an OPC Population Comprising Pretreatment

Undifferentiated human embryonic stem cells (uhESC) from the H1 line (WA01; Thomson J A, Itskovitz-Eldor J, Shapiro S S, Waknitz M A, Swiergiel J J, Marshall V S, Jones J M. Embryonic stem cell lines derived from human blastocysts. Science. 1998 Nov. 6; 282(5391): 1145-7) were cultured on 1:30 dilution of Matrigel® GFR in KO-DMEM with X-VIVO 10 medium supplemented with 80 ng/mL bFGF (ThermoFisher, PHG0263) and 0.5 ng/ml TGF-β1 (R&D System, cat #240-B). The medium was completely exchanged daily initiating 2 days after subculturing of the cells. Undifferentiated human embryonic stem cells were subcultured using collagenase and manual scraping.

The uhESC were exposed to a mixture of small molecules to prompt the cells prior to induction of differentiation. In the subculture passage prior to the initiation of the differentiation, the cells were seeded at approximately $0.8\text{-}1.0\times10^5$ cells/$cm^2$ and cultured as in previous passages. Once the uhESCs reached 30-50% confluence, the medium was changed to the glial progenitor medium with the small molecules added at a final concentration of 10 μM SB431542 (Sigma-Aldrich, cat #S4317), 2 μM Dorsomorphin (Sigma-Aldrich, cat #p5499), 3 μM CHIR99021 (Stemgent, cat #04-0004), and 0.5 μM Purmorphamine (Stemgent, cat #04-0009). The glial progenitor medium with the small molecule was exchanged daily for 4 days. On the fourth day, the glial progenitor medium was exchanged with an additional change in the added small molecules: 3 μM CHIR99021, 0.5 μM Purmorphamine, and 150 μM Ascorbic Acid (Sigma-Aldrich, cat #A4544). The medium with the added small molecules was exchanged daily for the next three days prior to the initiation of the differentiation.

The differentiation of the pretreated uhESC to OPCs was then initiated by enumerating the cells using a surrogate flask using collagenase IV (Life Technologies, cat #17104-019) and 0.05% Trypsin-EDTA (Life Technologies, 25300-054) in series to achieve a single cell suspension for quantification and harvesting the remaining pretreated cell cultures using 0.5 mM EDTA in PBS. The uhESC cultures were seeded into ultralow attachment (ULA) vessels to form embryoid bodies (EBs) at a density of $7.33\times10^5$ cells/$cm^2$ in a 1:1 mixture of X-VIVO 10 and glial progenitor medium (GPM). On the following day of the differentiation, there was a complete medium exchange using a 1:1 mixture of X-VIVO 10 and GPM. On this day the GPM was supplemented with 2 ng/mL hbFGF and 20 ng/ml EGF and 10 μM Retinoic acid in DMSO (RA, Sigma-Aldrich, cat #R-2625). Starting on the second day of the differentiation, the medium was 100% GPM supplemented only with 20 ng/ml EGF and 10 μM RA. This medium was replaced daily until Day 9. Starting on Day 9 through Day 27, the GPM medium, supplemented with 20 ng/mL EGF, was exchanged every other day. On Day 27 the EBs were plated onto vessels coated with Matrigel® GFR at a ratio of 2 $cm^2$ for every 1 $cm^2$ of ULA surface that was seeded at the initiation of differentiation. The culture medium used for the remainder of the entire differentiation was GPM supplemented with 20 ng/mL EGF. From Day 27 the cell cultures received a full medium replacement on alternating days. On Day 34 the cell cultures detached using 0.05% Trypsin-EDTA were counted and seeded onto Matrigel® GFR-coated vessels at $5\times10^4$ viable cells/$cm^2$. The GPM was replaced on alternating days starting on Day 34 until the final harvest on the seventh day.

The harvest of the OPCs on Day 41 involved a mixture of 0.05% Trypsin-EDTA supplemented with 20 U/mL Benzonasc (EMD Millipore, cat #P24-5513P3) and 0.01% Pluronic-F68 (Life Technologies, cat #24040-032). The detached cells were pooled in a 1:1 mixture of DMEM-F12 Medium and HypoThermosol FRS (BioLife Solutions, cat #101104) supplemented with 20 U/mL Benzonase and 0.01% Pluronic-F68 prior to counting and reformulation in CryoStor 5 prior to cryopreservation.

FIG. 5A shows a comparison of changes in NG2, K7, and PCK marker levels expressed in OPCs generated by the method in accordance to this example to OPCs generated without pretreatment with the small molecules described herein. OPCs generated with pretreatment steps express a higher level of NG2, and lower levels of K7 and PCK.

Example 2—Comparison of Alternative Methods of Producing an OPC Population Comprising Pretreatment Undifferentiated human embryonic stem cells (uhESCs) from the H1 line (WA01; Thomson J A, Itskovitz-Eldor J, Shapiro S S, Waknitz M A, Swiergiel J J, Marshall V S, Jones J M. Embryonic stem cell lines derived from human blastocysts. Science. 1998 Nov. 6; 282(5391): 1145-7) were cultured on one of the following matrices: 1:30 dilution of Matrigel® GFR in KO-DMEM, recombinant Laminin 521 (Corning self-coat Cat #354221 or PureCoat), or Vitronectin (StemCell Technologies cat #07180) in CellAdhere Dilution Buffer (StemCell Technologies cat #07183) with X-VIVO 10 medium supplemented with 80 ng/ml bFGF (ThermoFisher, PHG0263) and 0.5 ng/ml TGF-β1 (R&D System, cat #240-B). The medium was completely exchanged daily initiating 2 days after subculturing of the cells. Undifferentiated human embryonic stem cells were subcultured using collagenase and manual scraping or other non-enzymatic means such as 0.5 mM EDTA (Life Technologies cat #15575-020) in PBS or RcLeSR™ (Stemcell Technologies Cat #5872).

The uhESC were exposed to a mixture of small molecules to prompt the cells prior to induction of differentiation. In the subculture passage prior to the initiation of the differentiation, the cells were seeded at approximately $0.2\text{-}1.3\times10^5$ cells/$cm^2$ and cultured as in previous passages. Once the uhESCs reached 30-50% confluence, the medium was changed to the glial progenitor medium (GPM, as described herein) with the small molecules added at a final concentration of 10 μM SB431542 (Sigma-Aldrich, cat #S4317), 2 μM Dorsomorphin (Sigma-Aldrich, cat #p5499), 3 μM CHIR99021 (Stemgent, cat #04-0004), and 0.5 μM Purmorphamine (Stemgent, cat #04-0009). The glial progenitor medium with the small molecule was exchanged daily for 4 days. On the fourth day, the glial progenitor medium was exchanged with an additional change in the added small molecules: 3 μM CHIR99021, 0.5 μM Purmorphamine, and 150 μM Ascorbic Acid (Sigma-Aldrich, cat #A4544). The medium with the added small molecules was exchanged daily for the next three days prior to the initiation of the differentiation.

The differentiation of the pretreated uhESCs to OPCs was then initiated by enumerating the cells using a surrogate flask using collagenase IV (Life Technologies, cat #17104-019) and 0.05% Trypsin-EDTA (Life Technologies, 25300-054) in series to achieve a single cell suspension for quantification and harvesting the remaining pretreated cultures using 0.5 mM EDTA in PBS. The pretreated uhESC cultures were seeded into ultralow attachment (ULA) vessels to form embryoid bodies (EBs) at a density of $7.33\times10^5$ cells/$cm^2$ in a 1:1 mixture of X-VIVO 10 and glial progenitor medium (GPM) consisting of DMEM/F12 Gibco cat #10565-018, 2% B27 supplement Gibco cat #17504-044, 0.04 μg tri-iodo-thyronin Sigma cat #T5516-1MG supplemented with 4 ng/mL hbFGF and 20 ng/ml EGF (Life Technologies cat #PHG0311). Alternatively, rather than using the ULA tissue culture vessels, the pretreated cultures were cultured in agitated suspension systems to form EBs such as a 0.1 L disposable PBS spinners flasks at a concentration of $1.8\times10^6$ cells/mL and agitated at 25 rpm. On the following day of the differentiation, there was a complete medium exchange using a 1:1 mixture of X-VIVO 10 and glial progenitor medium or GPM. On this day the GPM was supplemented with 2 ng/mL hbFGF and 20 ng/mL EGF and 10 μM Retinoic acid in DMSO (RA, Sigma-Aldrich, cat #R-2625). Starting on the second day of the differentiation, the medium was 100% GPM supplemented only with 20 ng/mL EGF and 10 μM RA. This medium was replaced daily until Day 9. Starting on Day 9 through Day 27, the GPM medium, supplemented with 20 ng/mL EGF, was exchanged every other day. On Day 27 the EBs were plated onto vessels coated with Matrigel® GFR or recombinant Laminin or Vitronectin at a ratio of 2 $cm^2$ for every 1 $cm^2$ of ULA or 30 mL of suspension seeded at the initiation of differentiation. The culture medium used for the remainder of the entire differentiation was GPM supplemented with 20 ng/mL EGF. From Day 27 the cell cultures received a full medium replacement on alternating days. On Day 34 the cell cultures detached using 0.05% Trypsin-EDTA or TrypLE Select (Life Technologies, cat #A12859) were counted, and seeded onto Matrigel® GFR, recombinant Laminin or Vitronectin-coated vessels at $5\times10^4$ viable cells/$cm^2$. The GPM was replaced on alternating days starting on Day 34 until the final harvest on the seventh day.

The harvest of the OPCs on Day 41 involved a mixture of 0.05% Trypsin-EDTA or TrypLE Select supplemented with 20 U/mL Benzonase (EMD Millipore, cat #P24-5513P3) and 0.01% Pluronic-F68 (Life Technologies, cat #24040-032). The detached cells were pooled in a 1:1 mixture of DMEM-F12 Medium and HypoThermosol FRS (BioLife Solutions, cat #101104) supplemented with 20 U/mL Benzonase and 0.01% Pluronic-F68 prior to counting and reformulation in CryoStor 5 prior to cryopreservation.

Figure 2:
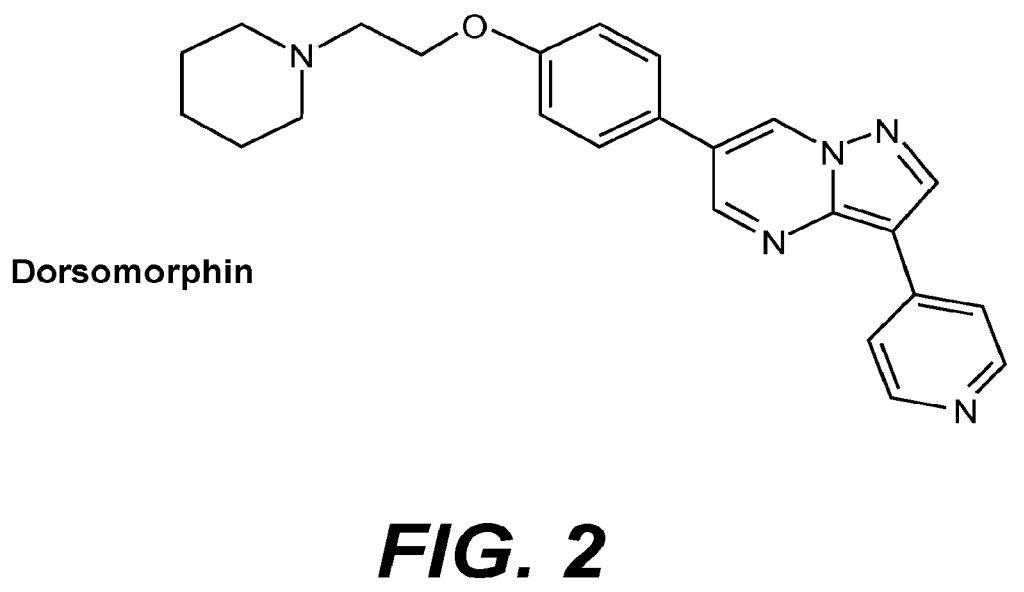

Referring to FIG. 5B through FIG. 5F, the effect of uhESC pretreatment with small molecule, in accordance with this example, on NG2, K7, and PCK marker level expression in OPCs was evaluated across different culturing conditions. OPCs generated with pretreatment steps express a higher level of NG2, and lower levels of K7 and PCK. Referring to FIG. 5B1-A, OPCs were produced under the following conditions during the expansion stage of uhESCs: XVIVO10 culture media and recombinant laminin matrix, using Collagenase IV for harvesting the expanded ES cells. Referring to FIG. 5B2-A, OPCs were produced under the following conditions during the expansion stage of uhESCs: XVIVO10 culture media and recombinant laminin matrix, using Collagenase IV for harvesting the expanded ES cells; the pretreated cultures are subsequently cultured in disposable PBS spinners flasks, while the controlled cultures are cultured in ULA vessels. Referring to FIG. 5C, OPCs were produced under the following conditions during the expansion stage of uhESCs: XVIVO10 culture media and Matrigel® GFR, using Collagenasc IV for harvesting the expanded ES cells; both the pretreated cultures and the control cultures are subsequently cultured in disposable PBS spinners flasks. Referring to FIG. 5D and FIG. 5E, OPCs were produced under the following conditions during the expansion stage of uhESCs: XVIVO10 culture media and Matrigel® GFR, using Collagenase IV for harvesting the expanded ES cells. Referring to FIG. 5F, OPCs were produced under the following conditions during the expansion stage of uhESCs: XVIVO10 culture media and Vitronectin matrix using ReLeSR™ for harvesting the expanded ES cells; the cultures are subsequently subjected to a short pretreatment while cultured on Vitronectin matrix and harvested prior to differentiation with EDTA.

Example 3—Characterization of Cell Population by Flow Cytometry

Flow cytometry were used to quantify the relative proportions of OPCs present in a differentiated population through identification of particular markers. Specifically, markers such as NG2, Nestin, and PDGF-Rα were quantified for each population.

To detect expression of cell surface markers, cells were washed with PBS and incubated in Stain Buffer (PBS with 2% FBS and 0.5% sodium azide) containing 10% goat serum to block non-specific binding sites. Then antibodies that specifically recognize the markers of interest (such as NG2, Nestin, PDGF-Rα, K7, pan-cytokeratin among others) and their isotype controls were incubated with cells. Unbound antibodies were removed by washing with Stain Buffer and, in the case of antibodies not conjugated with fluorophores, antibodies bound to cells were detected using an anti-antibody conjugated with fluorophores. Cells were washed and propidium iodide was then added to demark dead cells. Cells were acquired on a flow cytometer such as a FACSCalibur and only viable cells were analyzed. The percentage of cells expressing a given marker was calculated by subtracting the percent of cells with non-specific binding of the isotype control antibodies from the percent of cells binding the specific antibodies. The extent of marker expression per cell was calculated as a ratio of the fluorescence intensity of the marker position population to the fluorescence intensity of the isotype control-stained cells.

TABLE 2 is a comparison of representative marker expression between OPCs produced by a method in accordance with embodiments of the present disclosure, either with or without pretreatment of undifferentiated cells. A method comprising pretreatment as described herein produced OPCs that express significantly higher OPC markers NG2 and PDGF-Rα, and lower non-OPC markers such as Oct 4, Tra-1-60, K7, and PCK compared to a differentiation method without pretreatment.

TABLE 2

Representative marker expression by flow cytometry for OPCs produced by a method with and without pretreatment in accordance with the present disclosure

| | OPC Markers | | | Non-OPC Markers | | | |
|---|---|---|---|---|---|---|---|
| Method | Nestin | NG2 | PDGF-Rα | Oct4 | Tra-1-60 | K7 | PCK |
| No Pre-tx | 97 | 39 | 18 | 0.1 | 2 | 14 | 12 |
| Pre-tx | 99 | 50 | 81 | nd | nd | 0 | 5 |

TABLE 3 is a comparison of representative marker expression between OPCs produced by variations of methods in accordance with the embodiments of the present disclosure. The column headings "Stage I medium" and "Stage I process" refer to conditions that were applied during the expansion stage of uhESCs, whereas the column heading "Stage II process" refers to the type of pretreatment steps applied: (1) Control—where the cultures undergo no pretreatment in a flask or a spinner flask; (2) Pretreatment; (3) Pretreatment in a spinner flask, or (4) Short Pretreatment while being cultured on a Vitronectin matrix. In all test conditions, pretreatment increases NG2 expression in OPCs produced with pretreatment when compared to control, whereas epithelial markers K7 and PCK decreased in OPCs produced with pretreatment when compared to control.

TABLE 3

Representative marker expression by flow cytometry

| | Stage I Medium | Stage I Process | Stage II Process | NG2 | K7 | PCK |
|---|---|---|---|---|---|---|
| A | XVIVO10 | Matrigel(?) GFR/ Collagenase IV | Control | 38.8 | 20.4 | 30.2 |
| | XVIVO10 | Matrigel ® GFR/ Collagenase IV | Pretreatment | 50.3 | 0.2 | 4.8 |
| | XVIVO10 | recom. laminin/ Collagenase IV | Control | 21.1 | — | — |
| B1 | XVIVO10 | recom laminin/ Collagenase IV | Pretreatment | 61.6 | 3.3 | 3.2 |
| B2 | XVIVO10 | recom. laminin/ Collagenase IV | Pretreatment in spinner flask | 40.5 | 1.8 | 0.7 |

TABLE 3-continued

| Representative marker expression by flow cytometry | | | | | | |
|---|---|---|---|---|---|---|
| | Stage I Medium | Stage I Process | Stage II Process | NG2 | K7 | PCK |
| C | XVIVO10 | Matrigel GFR/ Collagenase IV | Control in spinner flask | 31.1 | 16.7 | 15.1 |
| | XVIVO10 | Matrigel ® GFR/ Collagenase IV | Pretreatment in spinner flask | 37.7 | 0.3 | 2.0 |
| D | XVIVO10 | Matrigel GFR/ Collagenase IV | Control | 65.3 | 53.5 | 21.7 |
| | XVIVO10 | Matrigel GFR/ Collagenase IV | Pretreatment | 78.3 | 5.2 | 1.9 |
| E | XVIVO10 | Matrigel ® GFR/ Collagenase IV | Control | 18.8 | 8.3 | 17.9 |
| | XVIVO10 | Matrigel GFR/ Collagenase IV | Pretreatment | 33.5 | 0.8 | 2.2 |
| F | XVIVO10 | XVIV010/ Vitronectin | POR | 21.9 | 6.0 | 22.9 |
| | XVIVO10 | XVIV010/ Vitronectin | Short Pretreatment | 70.9 | 4.1 | 6.7 |

Example 4—Characterization of Cell Population by Gene Expression Profiling

Gene expression profiling can be used to further characterize the cell types present both in the final OPC population and during its derivation from the starting hESC population. Gene expression profiling includes both global transcriptome profiling, using such methods as microarray and RNA-seq, and targeted gene profiling using methods of increased sensitivity such as quantitative real-time PCR (qPCR).

To perform gene expression profiling, cells were lysed in a nucleic acid-stabilizing solution such as Qiagen's RLT Lysis Buffer (Qiagen #79216), and RNA was purified using a standard extraction kit such as Qiagen's RNeasy Mini Kit (Qiagen #74106) according to the manufacturer's guidelines. For qPCR-based analysis, purified RNA was then converted to cDNA by standard methods, such as Qiagen's RT2 Easy First Strand Kit (Qiagen #330421) according to the manufacturer's guidelines. The relative expression level of target genes and reference housekeeping genes was then quantified using pre-made qPCR arrays, such as Qiagen's RT2 Profiler PCR arrays (Qiagen #330231) or individual probes, such as Qiagen's RT2 qPCR Primer Assays (Qiagen #330001) according to the manufacturer's guidelines. To determine relative expression levels of a given set of target genes, PCR reactions were performed on a standard real-time PCR machine, such as the ABI 7900HT Real-Time Sequence Detection System (Applied Biosystems), or equivalent. Each target gene was normalized to one or multiple reference genes, such as GAPDH, to determine its relative expression level.

For microarray analysis, purified RNA can be used to generate a cDNA library using standard methods such as the Affymetrix GeneChip WT PLUS Reagent Kit (Affymetrix #902281), hybridized to a whole transcriptome array, such as the Affymetrix HUGENE 2.0 ST array (Affymetrix #902113), and analyzed using standard instrumentation, such as the Affymetrix GeneChip Scanner 3000 7G System (Affyemetrix #00-0213) according to the manufacturer's guidelines. Resulting microarray data can then be normalized and subsequent analyses of relative gene expression can be performed using the Affymetrix Expression Console software package (Affymetrix) or equivalent.

TABLE 4 shows a representative qPCR analysis of neural/glial progenitor genes, ectoderm/neuroectoderm lineage genes, and non-neuroectoderm lineage genes in OPCs generated by a method in accordance with embodiments of the present disclosure, with or without pretreating undifferentiated cells. Here, RNA samples were collected on differentiation day 9 and processed for qPCR using methods described above. Four neural/glial progenitor genes are quantified: FABP7, NEUROG2, NKX2.2, and OLIG2. Four early ectoderm/neuroectoderm lineage genes were quantified: FGF5, FOXA1, GAD1, and GAD2. Five early non-neuroectoderm lineage genes were quantified: HAND1, HAND2, MYL3, NPPA, and OTX2. Fold expression relative to H1 hESC 6 OPC d9 was calculated using the ΔΔCT method with GAPDH as the housekeeping gene.

Referring to TABLE 4, OPCs generated by a method involving pretreatment, in accordance with an aspect of the present disclosure, show significantly increased expression of neural/glial progenitor genes compared to OPCs generated by a method without pretreatment. Namely, neural/glial progenitor genes FABP7, NEUROG2, NKX2.2, and OLIG2 were increasingly expressed in the OPCs produced by a method involving pretreatment. Early ectoderm/neuroectoderm lineage gene GAD2 was also significantly reduced in the OPCs generated by a method involving pretreatment compared to OPCs generated by without pretreatment. Further, when comparing to the method without pretreatment, a method comprising pretreatment in accordance with the present disclosure resulted in lower expression of non-neuroectoderm lineage genes during the differentiation process, including reduced expression of the trophoblast lineage gene, Hand1.

TABLE 4 qPCR analysis of neural/glial progenitor genes, ectoderm/neuroectoderm lineage genes, and non-neuroectoderm lineage genes in H1 hESCs differentiated into OPCs using a method in accordance with the present disclosure.

| | H1 hESC 1 OPC d9 without pre-tx | H1 hESC 2 OPC d9 without pre-tx | H1 hESC 3 OPC d9 without pre-tx | H1 hESC 4 OPC d9 without pre-tx | H1 hESC 5 OPC d9 without pre-tx | H1 hESC 6 OPC d9 without pre-tx | H1 hESC 7 OPC d9 without pre-tx | H1 hESC 8 OPC d9 without pre-tx |
|---|---|---|---|---|---|---|---|---|
| Neural/glial progenitor genes | | | | | | | | |
| FABP7 | 1.7 | −2.7 | 1.3 | 1.1 | −2.8 | 1.0 | 1.4 | 5.4 |
| NEUROG2 | 1.1 | −1.1 | −1.3 | −1.1 | −1.8 | 1.0 | −3.4 | 2.8 |
| NKX2.2 | −21.0 | −113.6 | 1.2 | −2.1 | −12.9 | 1.0 | −8.8 | 9.9 |
| OLIG2 | 1.3 | 1.3 | 1.1 | 1.7 | −1.8 | 1.0 | −2.5 | 104.7 |
| Early ectoderm/neuroectoderm lineage genes | | | | | | | | |
| FGF5 | −3.6 | −7.6 | −1.7 | −1.3 | −1.0 | 1.0 | −1.1 | −1.4 |
| FOXA1 | −3.9 | −4.5 | −1.1 | 1.1 | −1.3 | 1.0 | −1.3 | −3.3 |
| GAD1 | −7.3 | −16.3 | −1.0 | −1.2 | −2.6 | 1.0 | −1.7 | −6.2 |
| GAD2 | −3.1 | −6.0 | −1.4 | −1.1 | −1.7 | 1.0 | −1.6 | −17.3 |
| Early non-neuroectoderm lineage genes | | | | | | | | |
| HAND1 | 26.3 | 46.9 | 9.6 | 1.7 | 1.7 | 1.0 | 4.9 | −5.4 |
| HAND2 | 14.9 | 32.3 | 3.6 | 4.9 | 1.3 | 1.0 | 1.5 | −21.5 |
| MYL3 | 6.1 | 2.1 | 2.3 | 3.9 | 1.4 | 1.0 | −6.4 | −5.0 |
| NPPA | 4.3 | 7.0 | 2.1 | 1.5 | 2.0 | 1.0 | 1.3 | 2.2 |
| OTX2 | 7.0 | 13.2 | 2.4 | −1.1 | −1.4 | 1.0 | −11.8 | −5.4 |

When gene expression profiling was used to compare OPCs produced by a method without pretreatment and OPCs produced using a method with pretreatment in accordance with the present disclosure, both similarities and differences were observed. Both types of methods produced a population of NG2-positive OPCs that also expressed markers such as PDGF-Rα, DCN, and IGF2. However, when OPCs were generated using a method comprising pretreatment in accordance with the present disclosure, the expression of genes associated with other cell types was reduced, including such epithelial-associated genes as K7 and CDH1/E-cadherin.

Example 5—Assessing Undesirable Epithelial Lineage Cells Using an in Vitro Cyst Assay Presence of undesirable epithelial lineage cells in an OPC population generated from hESCs was tested using an in vitro cyst assay. The cyst assay was performed as described in Debnath et al. with the following modifications: (1) cells were cultured in 24 well plates with 40,000 cells input into each well; (2) cells were cultured for up to 35 days to allow more time for epithelial cell proliferation and enlargement of epithelial structures; (3) Cystic structures were detected by immunofluorescent staining and whole-well image acquisition using an IN Cell Analyzer 2000 (GE Healthcare Life Sciences) or similar automated imaging system; and (4) Cyst frequency and size was quantified using analytical software such as IN Cell Developer Software (GE Healthcare Life Sciences). (Debnath J, Muthuswamy S K, Brugge J S, Morphogenesis and oncogenesis of MCF-10A mammary epithelial acini grown in three-dimensional basement membrane cultures. Methods. 2003 July; 30(3):256-68.)

Specifically, to test cyst forming capacity, cells were grown in a 3D culture system in the presence of factors known to stimulate epithelial cyst formation for a period of 20 to 35 days. In addition to visual detection of cysts, the presence of cystic structures containing basolateral protein expression of the epithelial marker, CD49f, was also assessed using immunocytochemistry. Moreover, flow cytometry was utilized to detect epithelial markers and cyst formation in injured rodents to confirm the correlation between activity level measured by the cyst assay with the in vivo cyst activity.

Figure 6A:
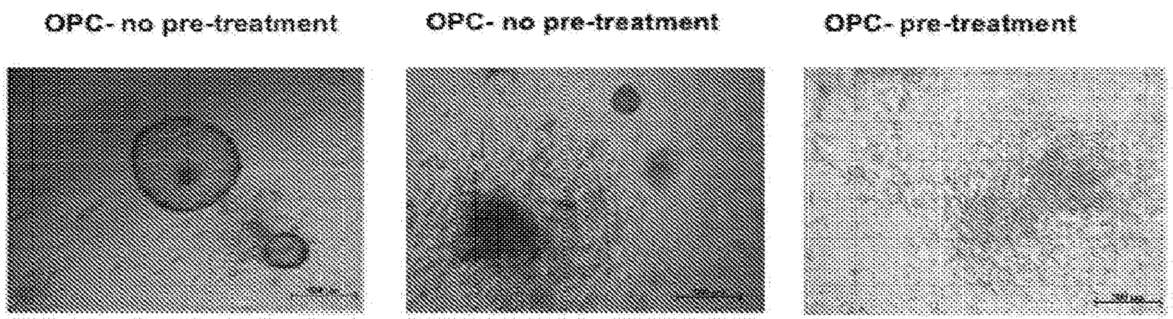
FIG. 6A, left and center panels are representative pictographs of H1 hESC-derived OPCs generated by a method without pretreating undifferentiated cells in accordance with the present disclosure showing various levels of cyst formation in an in vitro cyst assay according to the present disclosure.

When OPCs generated by a method without pretreatment were tested in the in vitro cyst assay, varying levels of epithelial cyst formation was observed. Referring to FIG. 6A, the left and center panels are representative pictographs of H1 hESC-derived OPCs generated by the method without pretreatment, exhibiting large and small cystic structures, respectively. On the other hand, different results were observed when OPCs generated by a method with pretreatment in accordance with the present disclosure were tested in the in vitro cyst assay. The right panel of FIG. 6A is a representative pictograph of H1 hESC-derived OPCs generated by a method comprising pretreatment in accordance with the current disclosure, which exhibits no cystic structures.

Figure 6B:
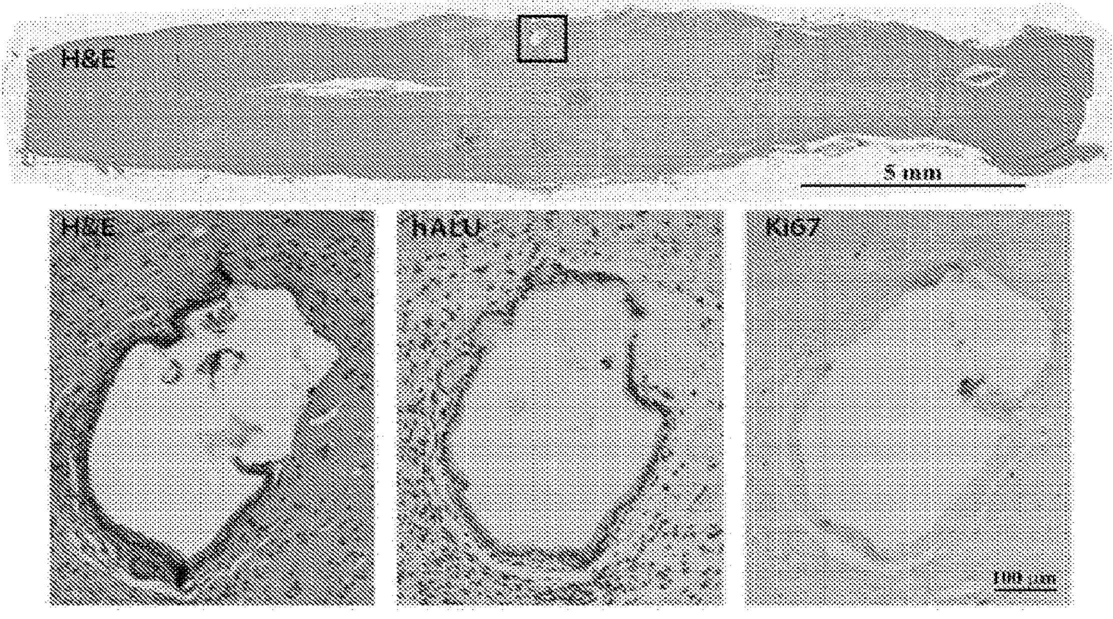
FIG. 6B shows a set of representative histology of an adult female rat 9 months after cervical spinal cord injury and administration of H1 hESC-derived OPCs generated by a method without pretreating undifferentiated cells in accordance with the present disclosure.
Figure 6C:
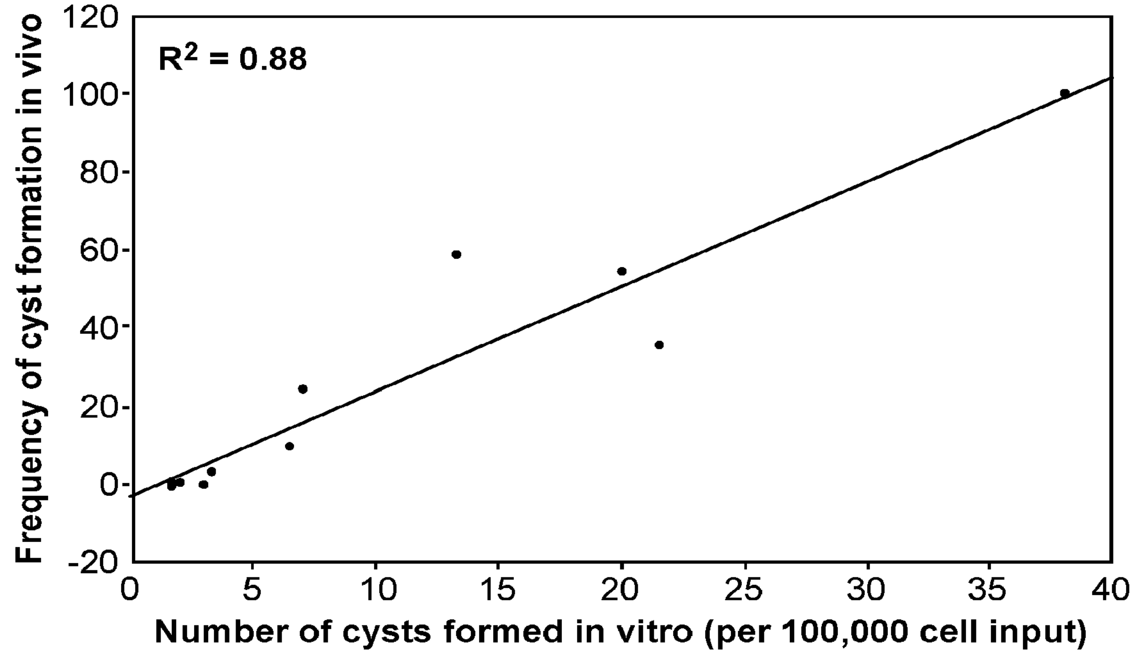
FIG. 6C is a linear regression plot of in vivo cyst formation frequency versus in vitro cysts count for several populations of OPCs generated by a method without pretreating undifferentiated cells.

OPC lots that formed cysts in the cyst assay were administered into the injured spinal cord of adult rodents, and gave rise to epithelial-like cystic structures in vivo. Referring to FIG. 6B, representative histology of an adult female rat 9 months after cervical spinal cord injury and administration of H1 hESC-derived OPCs generated by the method without pretreatment are shown at different magnifications and with different histological stains. The top panel of FIG. 6B is a low magnification image of a hematoxylin/eosin (H&E) stained spinal cord tissue containing the injury/OPC graft site. The black box indicates the location of an epithelial cystic structure. The bottom panels of FIG. 6B show high magnification images of the epithelial cystic structure stained with various histological stains. The bottom left panel shows an H&E staining. The central bottom panel shows a staining with the human-specific probe, hALU with eosin, confirming the presence of human cells within the structure. The bottom right panel shows a staining with the cell proliferation marker, Ki67 with eosin, showing minimal proliferative activity of cells within the cyst. Finally, FIG. 6C is a linear regression plot of in vivo cyst formation frequency versus in vitro cyst count for several populations of OPCs generated by the method without pretreatment, confirming that the number of cysts formed in vitro correlates with the frequency of cyst formation in this animal model.

In contrast, OPCs generated using a method with pretreatment and in accordance with the present disclosure expressed lower levels of epithelial markers by flow cytometry, and did not form epithelial cysts in the cyst assay (FIG. 6A, right panel). Referring to TABLE 5, OPCs generated by the method without pretreatment produced significantly more number of cysts in vitro compared to OPCs produced using a method with pretreatment in accordance with the present disclosure.

TABLE 5

Representative result from the cyst assay as described herein, comparing OPCs produced by a method described herein.

| | OPC-A without pre-tx | OPC-B without pre-tx | OPC-C without pre-tx | OPC-D without pre-tx | OPC-E without pre-tx | OPC-F without pre-tx | OPC-G with pre-tx |
|---|---|---|---|---|---|---|---|
| Cysts/100,000 cell input | 27 | 21 | 14 | 14 | 4 | 2 | 0 |
| Maximum cyst diameter (μm) | 1230 | 437 | 190 | 218 | 329 | 130 | NA |

microscopy were then used to measure cavitation area using standard imaging software such as ImageJ (NIH). To assess the relative presence of myelinated fibers within the injury site, fixed spinal cord tissue sections was stained with eriochrome cyanin using standard histological methods and imaged by bright field microscopy.

When OPCs are generated by the method without pretreatment and assessed in the manners described above, several observations were made. First, the transplanted cells exhibited robust engraftment up to 12 months post-transplant and migrate to the injury site as early as two weeks post-transplant. Relative to rats subjected to spinal cord injury and transplanted with vehicle, rats transplanted with these OPCs exhibited a reduction in injury-induced cavitation as early as two weeks post-transplantation, and this effect persisted up to 12 months post-transplant. Furthermore, myelinated axons were visible within the injury site beginning at approximately 3 months post-transplant and increasing up to 12 months post-transplant, whereas myelinated axons were unable to traverse a site of cavitation typically observed in injured, vehicle-treated rats (see Priest C A, Manley N C, Denham J, Wirth E D 3rd, Lebkowski J S, Preclinical safety of human embryonic stem cell-derived oligodendrocyte progenitors supporting clinical trials in spinal cord injury, Regen Med. 2015 November; 10(8):939-58, for examples of these observations).

Because the frequency of cyst formation and size of the cysts formed in the cyst assays are positively correlated with the population's relative capacity to form ectopic cystic structures in the injured spinal cord of rodents, the OPCs generated using a method with pretreatment in accordance with the present disclosure are expected not to form epithelial cysts in vivo.

Example 6—Engraftment of OPCS

The capacity of an OPC population to engraft in the mammalian central nervous system and migrate towards an injury site is an important measure of its biological activity and a potential measure of its potency. In addition, injury-induced cavitation and the presence of myelinated axons within the injury site can be measured as potential surrogates of post-injury repair/regeneration.

Figure 7:
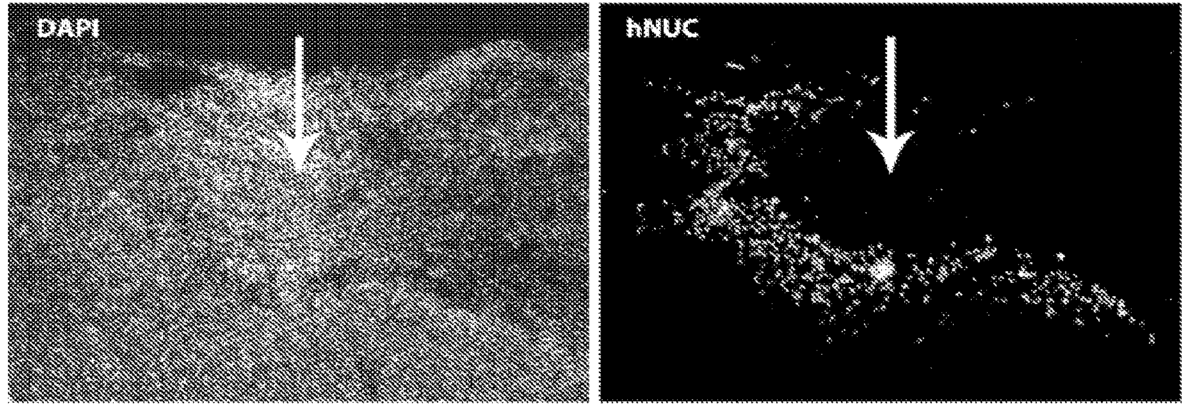
FIG. 7 shows representative photomicrographs of a rat cervical spinal cord engrafted with OPCs generated using a method comprising pretreating undifferentiated cells in accordance with the present disclosure.

To assess engraftment/migration and post-injury repair/regeneration in a rodent model of spinal cord injury, adult female athymic nude rats were used. Prior to OPC implantation, rats were subjected to a laminectomy surgery at the desired injury location (e.g. C5-C6 for a cervical injury), and a hemi-contusion/crush injury was performed using the Infinite Horizons Impactor (Precision Systems and Instrumentation #IH-0400 or equivalent) according to the manufacturer's guidelines. Approximately one week to one month post-injury, OPCs were transplanted directly into the spinal cord adjacent to the injury site at doses of $2.4\times10^5$-$2.4\times10^6$. From 2 weeks to 12 months post-transplantation, animals were then sacrificed and tissue is processed using standard histological methods. To assess engraftment and migration, fixed spinal cord tissue sections were stained with human-specific probes, such as an anti-human nuclei antibody (Millipore #MAB1281) following by the appropriate colorimetric or fluorescent-conjugated secondary antibodies according to the manufacturer's guidelines. To assess injury-induced cavitation, fixed spinal cord tissue sections were stained with hematoxylin and cosin solutions using standard histological methods. The collected images by bright field Referring to FIG. 7, an adult female rat was subjected to a C5 cervical spinal cord contusion injury, and OPCs generated using a method involving pretreatment in accordance with the present disclosure was transplanted. Two weeks post-transplant, longitudinal spinal cord sections were immunoflourescently stained with an anti-human nuclei antibody (hNUC) to label engrafted cells and DAPI to label all cell nuclei. FIG. 7 shows the injury site (white arrow) labeled with DAPI (left panel) and hNUC (right panel) and imaged on a Zeiss Axioskop 2. OPCs generated by a method involving pretreatment in accordance with the present disclosure exhibited robust engraftment and migration towards the injury site at two weeks post-transplant.

Example 7—Using the OPC Population for Treating Stroke

OPCs generated using a method in accordance with the present disclosure can be used for treating stroke. To show functional improvement, a previously established mouse model of subcortical white matter stroke (Sozmen et al., (2009) *J. Neurosci Methods* 180(2):261; Hinman et al., (2013) *Stroke* 44(1): 182) can be adapted to the immunodeficient NSG mouse (Shultz et al., (2007) *Nat Rev Immunol.* 7(20:118; jaxmice.jax.org/nod-scid-gamma).

Figure 8:
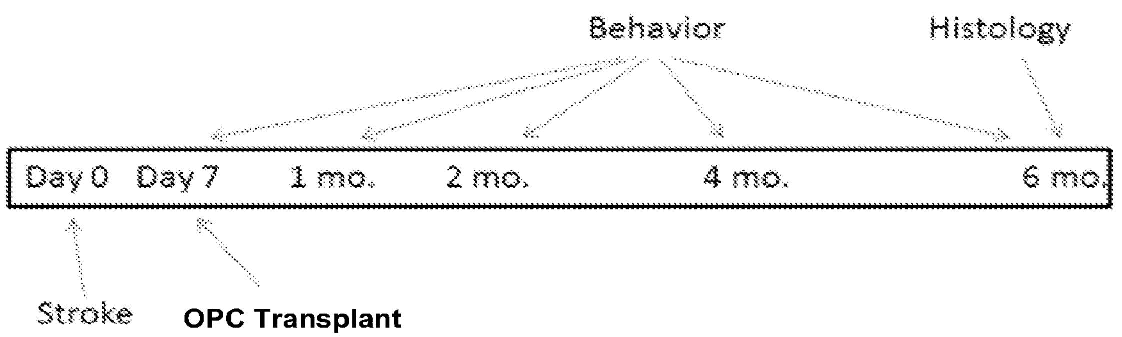
FIG. 8 shows a non-limiting example of an experimental timeline for testing the effects of transplanted OPCs in a mouse model of white matter stroke in accordance with the present disclosure.

Specifically, to induce focal ischemic lesions, N5-(1-iminoethyl)-L-ornithine, dihydrochloride (L-Nio, Calbiochem), is injected directly into the corpus callosum of each mouse brain. Subsequently, 100,000 OPCs/mouse (high dose), or 10,000 OPCs/mouse (low dose) are injected as a single 1 μL dose adjacent to the stroke lesion core 7 days post-stroke. An example of an experimental timeline is illustrated in FIG. 8. Neurological recovery is assessed by monthly behavioral testing.

Two types of behavior testing can be conducted in this study: the grid walking test and the cylinder test.

In a grid walking test, an animal is placed on an elevated, leveled grid with openings. Animals without brain damage will typically place their paws precisely on the wire frame-to hold themselves while moving along the grid. Each time a paw slips through an open grid, a "foot fault" is recorded. The number of both contralateral and ipsilateral faults for each limb is compared to the total number of steps taken and then scored using a foot fault index.

In a cylinder test, an animal is placed in a transparent Plexiglas cylinder and observed. Mice will actively explore vertical surfaces by rearing up on their hind limbs and exploring the surface with their forclimbs and vibrissac. When assessing behavior in the cylinder, the number of independent wall placements observed for the right forelimb, left forelimb and both forclimbs simultaneously are recorded.

A test group can be set up using 72 mice in total, with 12 mice in each of the following sub-groups: (1) control (sham surgery), (2) stroke alone, (3) OPC transplantation into non-stroke animals (half transplanted with low dose OPCs, the other half transplanted with high dose OPCs), (4) low dose OPC transplantation into stroke animals adjacent to the stroke lesion, (5) high dose OPC transplantation into stroke animals adjacent to the stroke lesion, and (6) high dose OPC transplantation into stroke animals into the stroke lesion.

Figure 9:
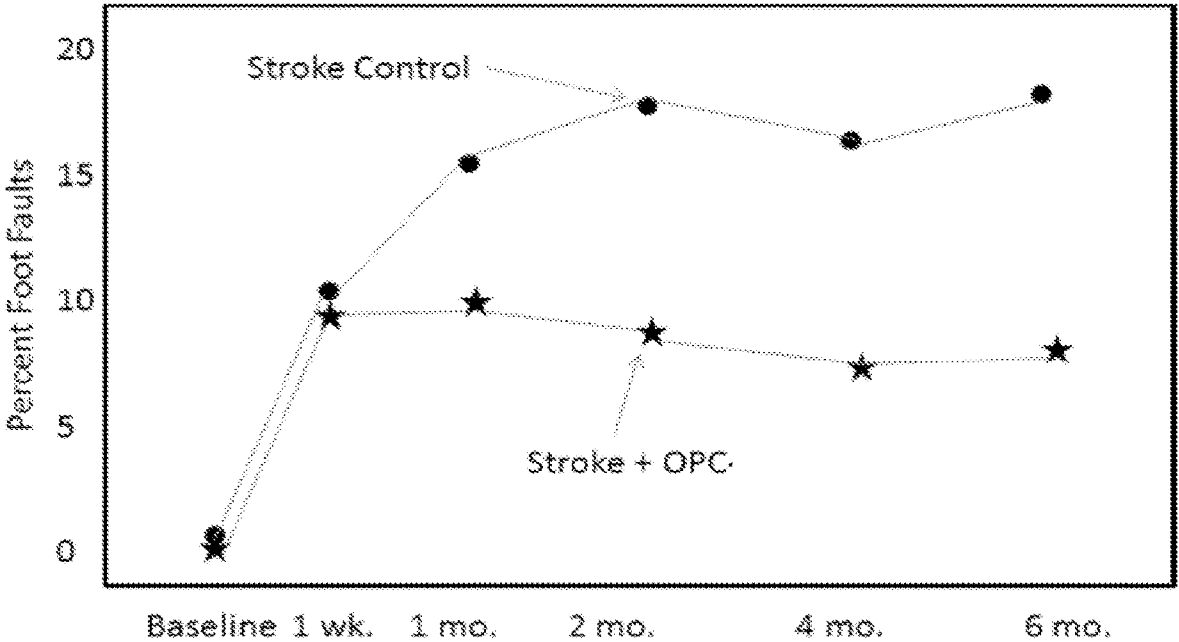
FIG. 9 shows non-limiting examples of anticipated results to be generated from a grid walking test, demonstrating improved performance in stroke-injured mice transplanted with OPCs generated by a method in accordance with embodiments of the present disclosure.
Figure 10:
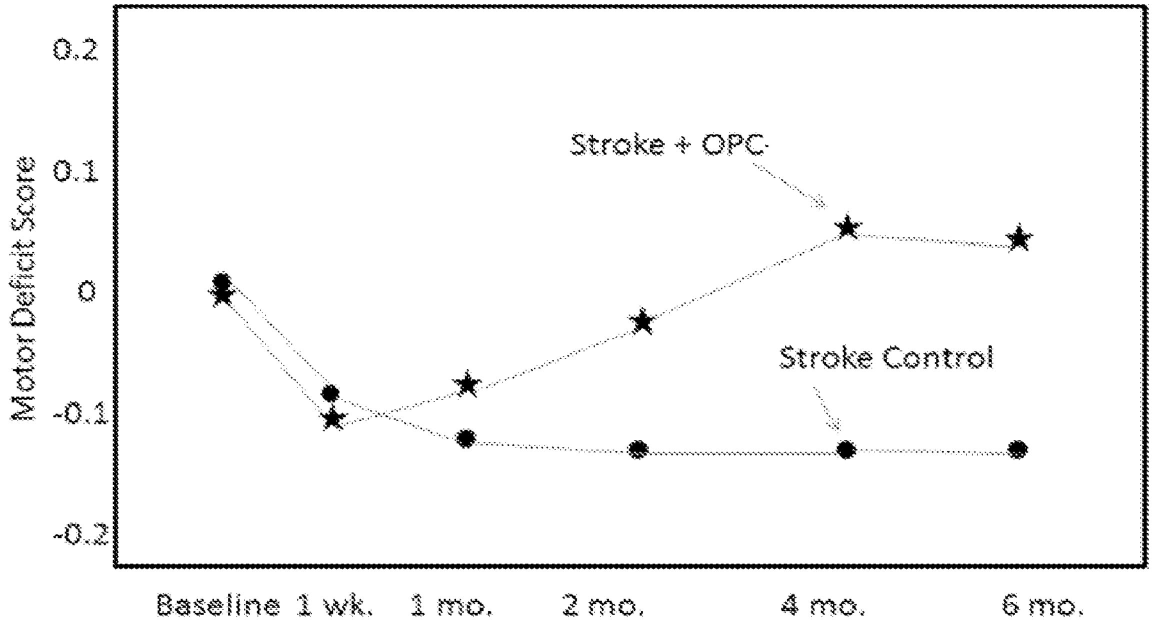
FIG. 10 shows non-limiting examples of anticipated results to be generated from a cylinder test, demonstrating improved performance in stroke-injured mice transplanted with OPCs generated by a method in accordance with embodiments of the present disclosure.

Anticipated data that could be generated from an experiment performed in accordance with this example are depicted in FIG. 9 and FIG. 10.

Referring to FIG. 9, performance in the grid walking test is expected to show improved fine motor control and gait at four months post-stroke and transplantation of OPCs generated in accordance with an aspect of the present disclosure.

Referring to FIG. 10, performance in the cylinder test is expected to show improvement at 4 months post transplantation of OPCs generated in accordance with one or more aspects of the present disclosure.

Example 8—Using the OPC Population for Treating Spinal Cord Injury

OPCs generated using a method in accordance with the present disclosure can be used for treating spinal cord injury. An efficacy study was conducted to test OPCs in a rat model of cervical spinal cord injury using both behavioral and histological assessments. This study modeled the most common human spinal cord injury, cervical contusion, and was restricted to a hemi-contusion to preserve robust animal survival and maintain reasonable animal husbandry requirements. An initial study was performed with OPCs generated by a method without pretreatment in accordance with the present disclosure.

Female athymic RNU rats received a cervical level C-6 unilateral (right) spinal cord contusion using the Infinite Horizons Impactor set to deliver a 250 kdyne contusion force. One week later, contused animals received $2.4\times10^5$ OPCs, or vehicle (HBSS), or a sham surgery. All animals received immunosuppression with anti-asialo GM1 antibody. Behavioral and kinematic testing was conducted at four time points during the study (baseline and 1 month, 2 months or 4 months post-transplantation) after which spinal cords are collected for histological assessment.

To administer OPCs or vehicle, a syringe was lowered into the spinal cord using a stereotaxic manipulator arm. Vehicle or OPC was administered into the dorsal spinal parenchyma caudal to the injury site via a single injection of 2.4 μL.

To assess behavioral recovery post-injury and treatment, this study incorporated the TreadScan gait analysis system (Clever Sys Inc., Reston, VA) that allows for quantitative measurements of 90 different locomotion attributes and gait mechanics.

For the TreadScan analysis, animals were placed on a motorized, clear treadmill and imaged from the ventral plane using a high speed camera during unrestrained locomotion for 20 seconds. The TreadScan Analyzing System software was then used to calculate attributes of gait from each of the four paws.

Figure 11:
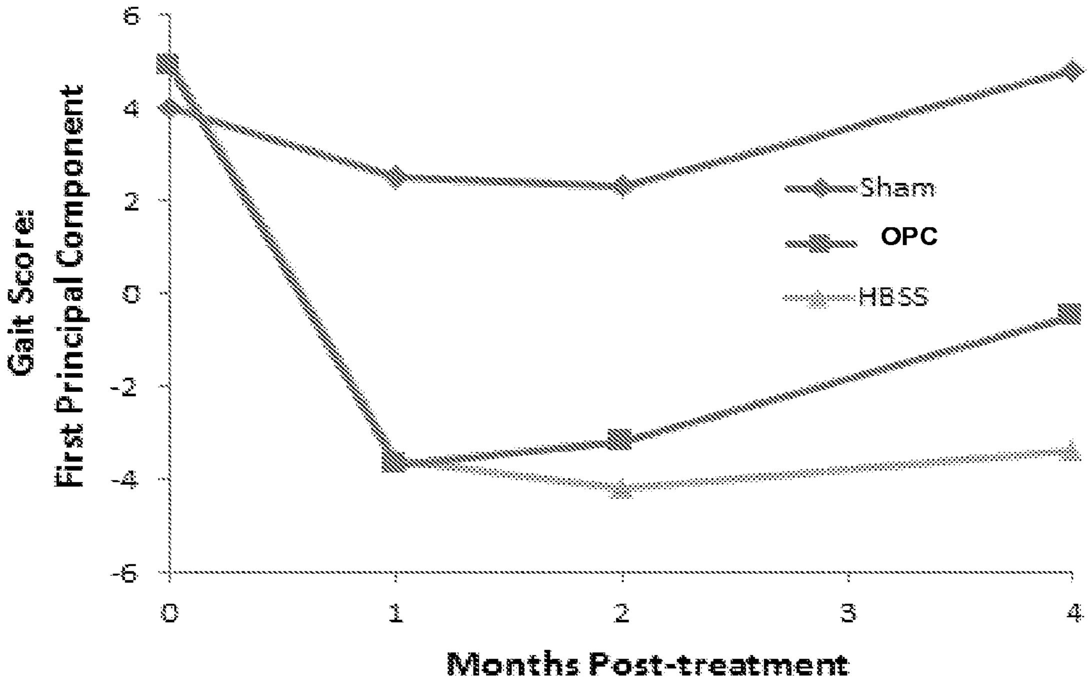
FIG. 11 is a representative first principal component analysis of gait parameters showing improved motor activity in injured rats transplanted with OPCs generated by a method without pretreating undifferentiated cells in accordance with the present disclosure.

Using these gait parameters, multifactorial methods were used to statistically analyze the entire data set. A first principal component (PC) analysis was performed to condense the 90 individual TreadScan measurements into one value for each of the 43 animals at each of the four time points. Plotted from baseline, the first PC (FIG. 11) shows the divergence of injured animals from the uninjured sham group during the first month post-injury. After the first month, animals that received OPCs recovered some locomotor activity, while the animals that receive HBSS vehicle showed little recovery ($p\leq0.05$). Functional improvements began to appear at 2 months post-transplantation and continued to increase at 4 months.

Multivariate analysis used to generate the First Principal Component also identified the individual parameters most responsible for the overall scores. The top three parameters were running speed, right rear stride frequency, and front right maximum longitudinal deviation. These three parameters are plotted in FIG. 12, FIG. 13, and FIG. 14, respectively for injured rats receiving OPCs generated by a method without pretreatment.

Figure 12:
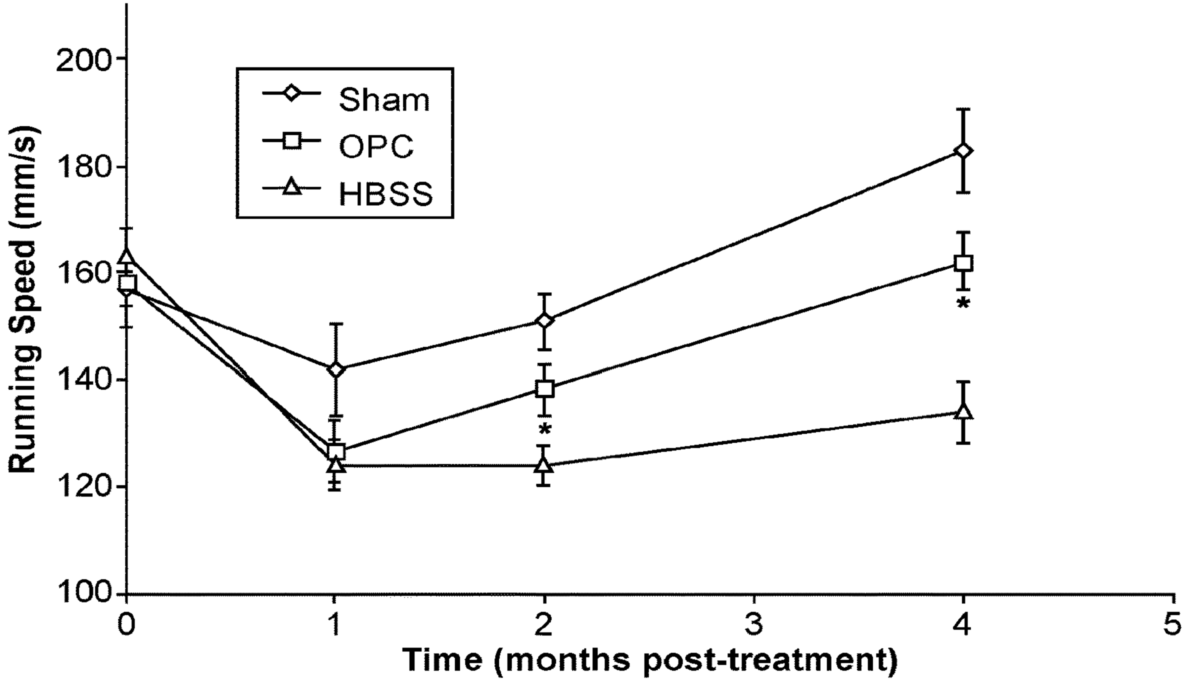
FIG. 12 is a representative plot of average running speed showing increased running speed in spinal cord injured rats transplanted with OPCs generated by a method without pretreating undifferentiated cells in accordance with the present disclosure.

Referring to FIG. 12, the average running speed for the uninjured sham rats, injured rats receiving a vehicle, and injured rats receiving OPCs were plotted at 4 designated time points. At baseline, animals across all groups ran at a similar speed. One month after injury, animals treated with OPCs or vehicle (HBSS) ran slower than the Sham animals, indicative of the effects of injury. At two and four months, both the Sham and OPCs treatment groups increased their running speed with a similar rate of improvement. By contrast, HBSS vehicle group showed little increase in running speed throughout the study. The animals transplanted with OPCs had a statistically significant faster running speed than animals in the vehicle control group at both 2 and 4 months after treatment ($p\leq0.05$).

Figure 13:
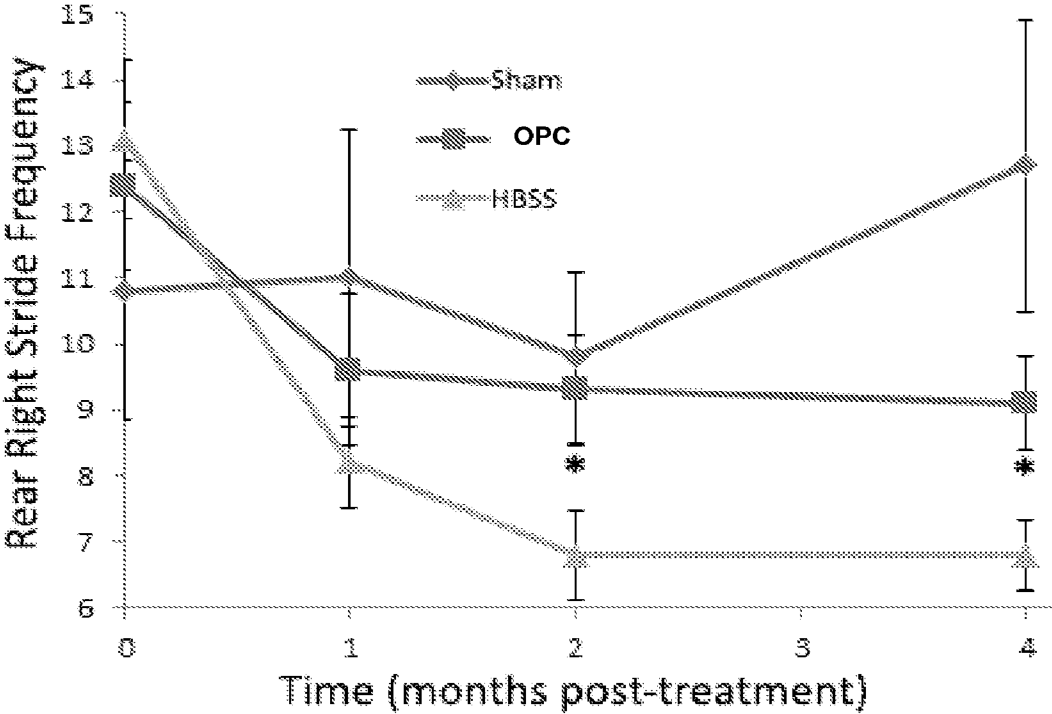
FIG. 13 is a representative plot of rear right stride frequency showing decreased motor impairment in spinal cord injured rats transplanted with OPCs generated by a method without pretreating undifferentiated cells in accordance with the present disclosure.

Referring to FIG. 13, the right rear stride frequency for the uninjured sham rats, injured rats receiving a vehicle, and injured rats receiving OPCs were plotted at 4 designated time points. Animals that received OPCs generated by a method without pretreatment were less severely impaired after transplantation. Specifically, animals treated with OPCs had a right rear stride frequency closer to that of Sham animals than that of the HBSS vehicle-treated injured rats (FIG. 13) and were significantly different ($p\leq0.05$) from that of the vehicle group.

Figure 14:
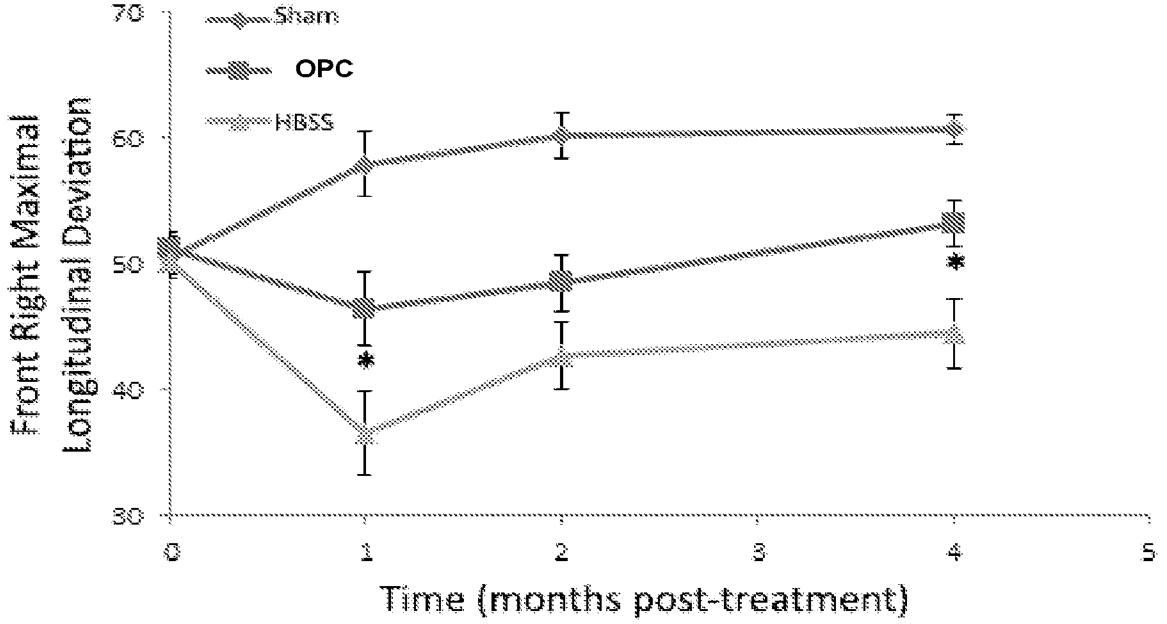
FIG. 14 is a representative plot of mean front right maximal longitudinal deviation, showing recovery of longitudinal displacements of the affected limb in spinal cord injured rats transplanted with OPCs generated by a method without pretreating undifferentiated cells in accordance with the present disclosure.

Referring to FIG. 14, front right maximal longitudinal deviation for the uninjured sham rats, injured rats receiving a vehicle, and injured rats receiving OPCs generated by a method without pretreatment were plotted at 4 designated time points. This measures the greatest distance of the front right foot (the injured side) relative to the short body axis (waist axis). Here, animals receiving OPCs displayed longitudinal displacements of the affected front right limb that were closer to that of Sham animals and statistically different from animals receiving HBSS vehicle (FIG. 14).

Figure 15:
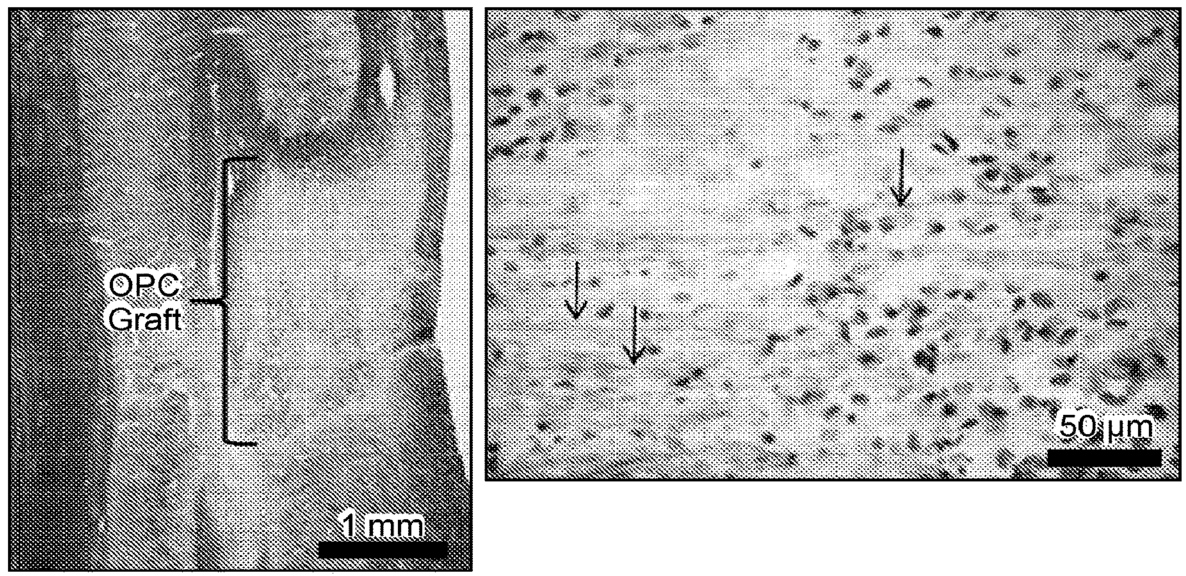
FIG. 15 is a representative section of an OPC graft 4 months post-injection of OPCs generated by a method without pretreating undifferentiated cells in accordance with the present disclosure.

Postmortem histological analyses from the efficacy studies showed that OPC-treated rats have surviving OPCs, reductions of parenchymal cavity formation and the presence of myelinated fibers traversing the injury site (FIG. 15). Cell nucleus was stained with human nuclear antigen, and myelin is stained with eriochrome cyaninc. Tract tracing identified axonal fibers from the rubrospinal and reticulospinal tracts within the OPC grafts and caudal to injury sites. Referring to the left panel of FIG. 15, complete filling of the lesion cavity by the transplanted OPCs was observed. The right panel of FIG. 15 shows the presence of myelinated axons (arrows) within the OPC graft.

Together, the TreadScan analysis showed that OPCs generated by a method without pretreatment were able to reverse motor deficits caused by a contusion injury to the rat cervical spinal cord. Hence, improvements in both kinematic measurements and spinal cord tissue histology were observed in injured animals that were transplanted with OPCs generated by a method without pretreatment.

It is expected that transplantation of OPCs generated by a method with pretreatment will provide at least the same level of functional improvement provided by transplantation of OPCs generated by a method without pretreatment.

Example 9—Using the OPC Population for Treating Multiple Sclerosis

Figure 16:
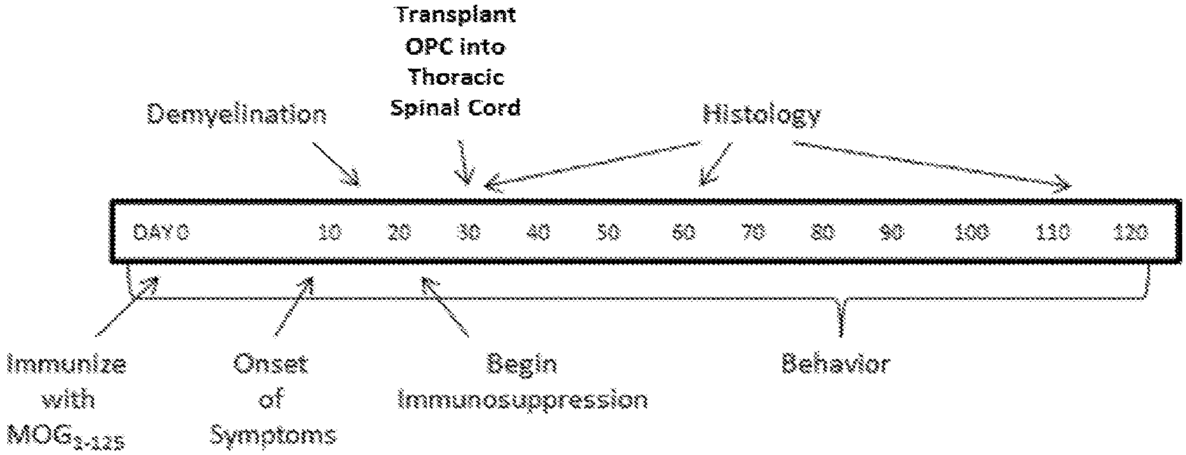
FIG. 16 shows a non-limiting example of an experimental timeline for testing the effects of transplanted OPCs in a rat model of multiple sclerosis in accordance with the present disclosure.

OPCs generated using a method in accordance with the present disclosure can be used for treating multiple sclerosis (MS), which is an autoimmune disease resulting in the demyelination of axon in the central nervous system. To test the ability of OPCs to remyelinate damaged axons and restore motor function, a rodent model of MS essentially as described by Stosic-Grujicic et al. is employed (Stosic-Grujicic S, Ramic Z, Bumbasirevic V, Harhaji L, Mostarica-Stojkovic M. Induction of experimental autoimmune encephalonmyelitis in Dark Agouti rats without adjuvant. Clin. Exp. Immunol. 2004. 136:49-55). The model uses Dark Agouti rats given experimental autoimmune encephalomyelitis (EAE) via immunization with the Myelin Oligodendrocyte Glycoprotein $MOG_{1-125}$. A non-limiting example of an experimental outline is illustrated in FIG. 16, with OPC transplantation on day 30 after immunization.

Figure 17:
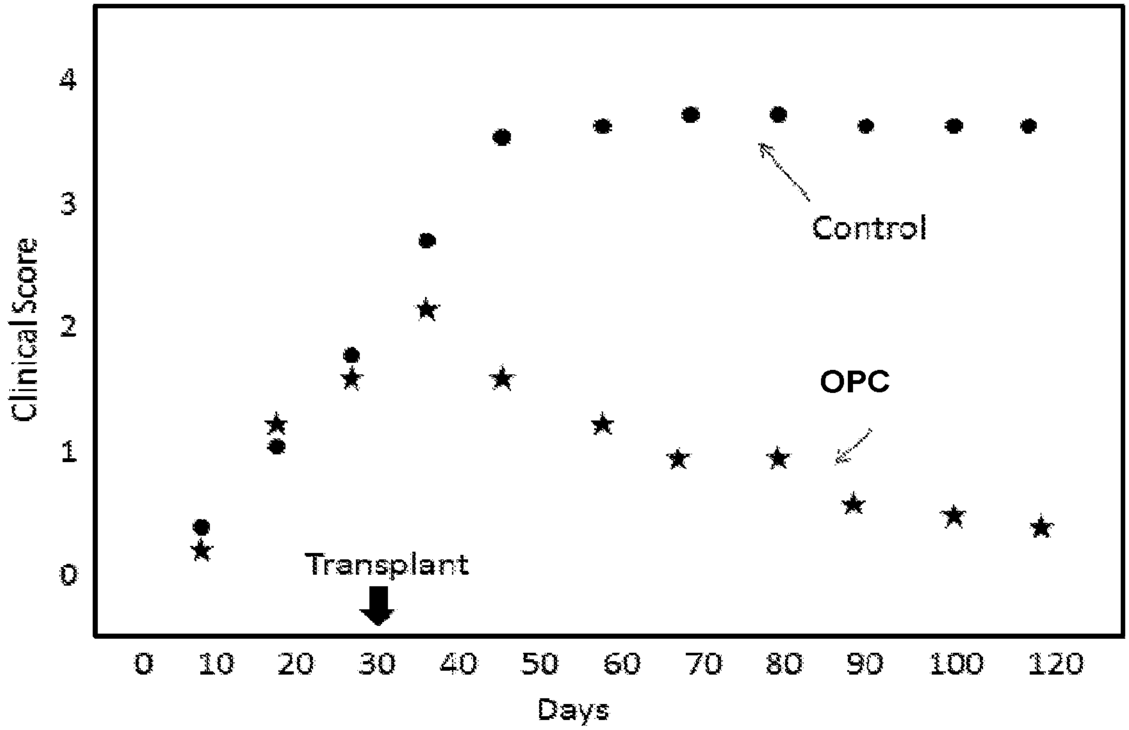
FIG. 17 is a non-limiting example of a plot of anticipated encephalomyelitis (EAE) scores to be generated upon transplantation of OPCs generated by a method in accordance with embodiments of the present disclosure.

To examine the effect of OPC transplantation on the behavior of test animals, clinical score for each animal is determined using the scoring system described in Stosic-Grujicic et al., 2004. Anticipated data that could be generated from experiments performed in accordance with this example and obtained from comparing a control group with animals transplanted with OPCs produced in accordance with an aspect of the present disclosure are shown in FIG. 17. Histological analysis and electron microscopy of transplantation of OPCs generated without pretreatment in demyelinated animal models indicate that the implanted OPCs engraft and produce myelin.

Together, these results demonstrate that transplantation of OPCs produced by a method without pretreatment have potential to reverse motor dysfunction and dysmyelination in EAE models.

It is expected that transplantation of OPCs generated by a method with pretreatment will provide at least similar levels of remyelination and functional improvement in an EAE model of MS.

While the present disclosure has been described with reference to particular aspects, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the scope of the present disclosure.

Therefore, it is intended that the present disclosure not be limited to the particular aspects disclosed as the best mode contemplated for carrying out the present disclosure, but that the present disclosure will include all aspects falling within the scope and spirit of the appended claims.

The invention claimed is:

1. A container comprising a pharmaceutical composition comprising a population of cells comprising a plurality of oligodendrocyte progenitor cells (OPCs), wherein:

(i) the population of cells comprises less than 5% epithelial lineage cells expressing Cytokeratin 7 (K7) or Pan-cytokeratin (PCK), (ii) at least 98% of cells in the population express Nestin, (iii) at least about 50% of cells in the population express NG2, and (iv) at least 80% of cells in the population express PDGF-Rα, and wherein the population of cells are obtained from pluripotent stem cells having a common genetic background.

2. The container according to claim 1, wherein the population of cells has not undergone cell enrichment.

3. The container according to claim 1, wherein the container is configured for cryopreservation.

4. The container according to claim 1, wherein the population of cells comprises less than 2% K7 positive cells.

5. The container according to claim 1, wherein at least 90% of the cells in the population of cells express at least one of Nkx 2.2, Olig1 or IGF2.

6. The container according to claim 1, wherein the population of cells produces one or more biological signaling factors.

7. The container according to claim 6, wherein the one or more biological signaling factors comprises Thrombospondin 1, Serpine1, Serpine2, Glial-Derived Nexin 1, Lumican, TIMP2, IGF2, MMP15, VEGF, Midkine or Decorin.

8. The container according to claim 1, wherein the population of cells produces one or more neurotrophic signaling factors.

9. The container according to claim 8, wherein the one or more neurotrophic signaling factors comprises NGF, Netrin 4, Tenascin C, Thrombospondin 1, Thrombospondin 3, SLIT1 or SLIT3.

10. The container according to claim 1, wherein the pharmaceutical composition comprises dimethyl sulfoxide.

* * * * *